US010261090B2

(12) United States Patent
Urano et al.

(10) Patent No.: US 10,261,090 B2
(45) Date of Patent: Apr. 16, 2019

(54) GLUTATHIONE-DETECTING FLUORESCENT PROBE

(71) Applicant: THE UNIVERSITY OF TOKYO, Tokyo (JP)

(72) Inventors: Yasuteru Urano, Tokyo (JP); Mako Kamiya, Tokyo (JP); Keitaro Umezawa, Tokyo (JP); Masafumi Yoshida, Tokyo (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 73 days.

(21) Appl. No.: 15/116,661

(22) PCT Filed: Feb. 24, 2015

(86) PCT No.: PCT/JP2015/055276
§ 371 (c)(1),
(2) Date: Oct. 24, 2016

(87) PCT Pub. No.: WO2015/129705
PCT Pub. Date: Sep. 3, 2015

(65) Prior Publication Data
US 2017/0045525 A1 Feb. 16, 2017

(30) Foreign Application Priority Data
Feb. 28, 2014 (JP) ................. 2014-037640

(51) Int. Cl.
*G01N 33/68* (2006.01)
*C09B 11/08* (2006.01)
*C09B 11/24* (2006.01)
*C09B 11/28* (2006.01)
*C09B 19/00* (2006.01)
*C09K 11/07* (2006.01)
*G01N 21/64* (2006.01)
*C07F 7/08* (2006.01)
*G01N 33/58* (2006.01)
*C09K 11/06* (2006.01)

(52) U.S. Cl.
CPC ............ *G01N 33/68* (2013.01); *C07F 7/081* (2013.01); *C07F 7/0812* (2013.01); *C09B 11/08* (2013.01); *C09B 11/24* (2013.01); *C09B 11/28* (2013.01); *C09B 19/00* (2013.01); *C09K 11/06* (2013.01); *C09K 11/07* (2013.01); *G01N 21/6428* (2013.01); *G01N 21/6458* (2013.01);
(Continued)

(58) Field of Classification Search
CPC ....... C07F 7/0812; C09K 11/06; C09K 11/07; C09K 2211/1033; C09K 2211/1055; G01N 21/6428; G01N 33/6815; G01N 33/582
USPC ........................................................ 435/183
See application file for complete search history.

(56) References Cited

U.S. PATENT DOCUMENTS

2008/0249321 A1  10/2008  Nagano et al.
2011/0111446 A1   5/2011  Abe et al.
2014/0342384 A1  11/2014  Nagano et al.

FOREIGN PATENT DOCUMENTS

CN     101093222 A   12/2007
JP     2014-50396 A   3/2014
(Continued)

OTHER PUBLICATIONS

Jung et al. 2012. A cysteine-selective fluorescent probe for the cellular detection of cysteine. Biomaterials, vol. 33, pp. 945 to 953. (Year: 2012).*
Pires et al. 2008. Fluorescence Imaging of Cellular Glutathione Using a Latent Rhodamine. Organic Letters, vol. 10, pp. 837-840. (Year: 2008).*
Anderson, "determination of Glutathione and Glutathione Disulfide in Biological Samples", Methods in Enzymology, vol. 113, pp. 548-555, 1985.
International Search Report issued with respect to application No. PCT/JP2015/055276, dated May 19, 2015.
International Preliminary Report on Patentability issued with respect to application No. PCT/JP2015/055276, dated Sep. 6, 2016.

*Primary Examiner* — Yevgeny Valenrod
(74) *Attorney, Agent, or Firm* — Greenblum & Bernstein, P.L.C.

(57) ABSTRACT

[Problem] To provide the following: a novel fluorescent probe for detecting a compound, such as glutathione, that contains a —SH group; a detection method using said fluorescent probe; and a detection kit containing said probe. [Solution] A fluorescent probe for detecting a compound containing an —SH group, wherein the fluorescent probe comprises a compound represented by formula (I) or a salt thereof (In the formula, X represents $Si(R^a)(R^b)$, $Ge(R^a)(R^b)$, $Sn(R^a)(R^b)$, $C(R^a)(R^b)$, or O (wherein $R^a$ and $R^b$ each independently represent a hydrogen atom or alkyl group); $R^1$ represents a hydrogen atom, or 1-4 identical or different substituents independently selected from the group consisting of a cyano group, alkyl group, carboxyl group, ester group, alkoxy group, amide group, and azide group, each of which may be optionally substituted; $R^2$ represents a hydrogen atom, halogen atom, hydroxyl group, cyano group, or an alkyl group, alkynyl group, alkoxy group, aryl, or heteroaryl, each of which may be optionally substituted; $R^3$ and $R^4$ each independently represent a hydrogen atom or 1-3 identical or different substituents independently selected from the group consisting of a hydroxyl group, halogen atom, or an alkyl group, sulfo group, carboxyl group, ester group, amide group and azide group, each of which may be optionally substituted; $R^5$, $R^6$, $R^7$ and $R^8$ each independently represent a hydrogen atom or alkyl group, wherein $R^5$ or $R^6$, respectively together with $R^3$, may form a ring structure including the nitrogen atoms bonded thereto, or $R^7$ or $R^8$, respectively together with $R^4$, may form a ring structure including the nitrogen atoms bonded thereto).

17 Claims, 5 Drawing Sheets

(52) U.S. Cl.
CPC ....... *G01N 33/582* (2013.01); *G01N 33/6815* (2013.01); *C09K 2211/1007* (2013.01); *C09K 2211/1033* (2013.01); *C09K 2211/1055* (2013.01); *C09K 2211/1088* (2013.01); *C09K 2211/1096* (2013.01); *G01N 2021/6439* (2013.01); *G01N 2021/6441* (2013.01)

(56) References Cited

FOREIGN PATENT DOCUMENTS

| | | |
|---|---|---|
| WO | 2005/085811 A1 | 9/2005 |
| WO | 2009/107448 A1 | 9/2009 |
| WO | 2012/111818 A1 | 8/2012 |
| WO | 2013/180181 A1 | 12/2013 |
| WO | 2014/106957 A1 | 7/2014 |

* cited by examiner

OSC-19                OSC-19 10 min after addition
                      of 200 µM NEM

GLUTATHIONE-DETECTING FLUORESCENT PROBE

This application is a National Stage of International Patent Application No. PCTJP2015/055276, filed Feb. 24, 2015 and claims priority under 35 U.S.C. § 119 to Japanese Application No. 2014-037640, filed Feb. 28, 2014. The disclosures of each of International Patent Application No. PCTJP2015/055276 and Japanese Application No. 2014-037640 are expressly incorporated by reference herein in their entireties.

TECHNICAL FIELD

The present invention relates to a novel fluorescent probe for detecting compounds having an —SH group, such as glutathione. More specifically, the present invention relates to a fluorescent probe for detecting the glutathione concentration in cells reversibly, a detection method using this fluorescent probe, and a detection kit including this probe.

BACKGROUND ART

Glutathione (GSH) functions as a major antioxidant within cells and plays an important role in various pathophysiologies associated with oxidative stress. The glutathione concentration in cancer cells is also said to be maintained higher than in normal cells, and it is thought to be one cause of treatment resistance to radiation and anti-cancer drugs.

Therefore, measuring the intracellular glutathione concentration is important for clarifying the participation of oxidative stress in various pathologies. Furthermore, estimating the glutathione concentration of cancer cells can serve as a highly useful tool in actual practice to make it possible to predict treatment resistance and the like.

Methods for measuring the glutathione concentration using a reagent that changes fluorescence intensity and emission intensity before and after reaction with glutathione are consequently being researched. However, existing glutathione measurement reagents and methods reported in the literature (such as Non-patent Reference 1) do not permit measurement in live cells since the cells must be disrupted for reaction with the intracellular glutathione. There are also reports of glutathione-sensitive probes that can be applied to living cells, but all have poor quantitativeness and problems remain in that measurement over time is not possible because an irreversible reaction with glutathione is utilized.

PRIOR ART REFERENCES

Non-Patent References

Non-patent Reference 1: Anderson, Methods in Enzymol., 1985, 113, 548.

DISCLOSURE OF THE INVENTION

Problems to be Solved by the Invention

The purpose of the present invention is to develop a method for measuring the intracellular glutathione concentration reversibly in living cells, and the problem is to develop a fluorescence control mechanism utilizing a reversible reaction with glutathione and to develop a novel fluorescent probe that can be applied in living cells.

As a result of in-depth research conducted to solve the above problems, the present inventors noted a phenomenon whereby compounds containing an —SH group such as glutathione concentration-dependently cause nucleophilic attack of position 9 of the xanthene ring of rhodamine and rhodamine-like skeletons (collectively referred to hereinafter as "rhodamine-like skeleton") and eliminate the visible light region absorption and fluorescence of compounds having a rhodamine-like skeleton, discovered a fluorophore that changes fluorescence intensity reversibly and concentration-dependently at physiological glutathione concentrations, and accomplished the present invention. They also developed a fluorescence resonance energy transfer (FRET)-type fluorescent probe having this fluorophore as an acceptor, and discovered that reversible detection of the glutathione concentration in living cells can be achieved. The present invention can also be applied to the detection of compounds other than glutathione as long as they are compounds containing an —SH group.

Specifically, the present invention, in one embodiment, provides (1) a fluorescent probe for detecting a compound containing an —SH group, wherein the fluorescent probe comprises a compound represented by formula (I) or a salt thereof.

[Chemical formula 1]

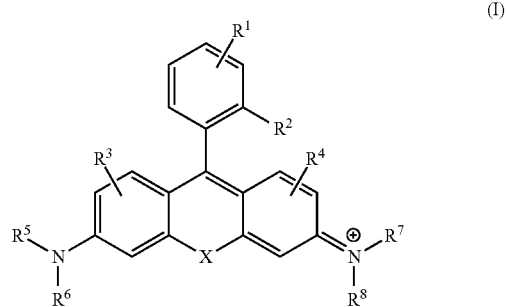

(I)

[In the formula,

X represents $Si(R^a)(R^b)$, $Ge(R^a)(R^b)$, $Sn(R^a)(R^b)$, $C(R^a)(R^b)$, or O (wherein, $R^a$ and $R^b$ each independently represent a hydrogen atom or alkyl group);

$R^1$ represents a hydrogen atom, or 1-4 identical or different substituents independently selected from the group consisting of a cyano group, alkyl group, carboxyl group, ester group, alkoxy group, amide group, and azide group, each of which may be optionally substituted;

$R^2$ represents a hydrogen atom, halogen atom, hydroxyl group, cyano group, or an alkyl group, alkynyl group, alkoxy group, aryl, or heteroaryl, each of which may be optionally substituted;

$R^3$ and $R^4$ each independently represent a hydrogen atom or 1-3 identical or different substituents independently selected from the group consisting of a hydroxyl group, halogen atom, or an alkyl group, sulfo group, carboxyl group, ester group, amide group and azide group, each of which may be optionally substituted;

$R^5$, $R^6$, $R^7$ and $R^8$ each independently represent a hydrogen atom or alkyl group; wherein, $R^5$ or $R^6$, respectively together with $R^3$, may form a ring structure including the nitrogen atoms bonded thereto, or $R^7$ or $R^8$, respectively together with $R^4$, may form a ring structure including the nitrogen atoms bonded thereto.]

The present invention, in preferred embodiments, provides (2) the fluorescent probe according to (1) above wherein the compound containing an —SH group is a compound having a cysteine residue;

(3) the fluorescent probe according to (1) above wherein the compound containing an —SH group is glutathione;

(4) the fluorescent probe according to any of (1)-(3) above wherein X is Si($R^a$) ($R^b$);

(5) the fluorescent probe according to any of (1)-(4) above wherein $R^2$ is a hydrogen atom, hydroxyl group, cyano group, or $C_1$-$C_4$ alkyl group, $C_1$-$C_4$ alkoxy group, or phenyl group, each of which may be optionally substituted; $R^5$, $R^6$, $R^7$, and $R_8$ are each independently a hydrogen atom or methyl group;

(6) the fluorescent probe according to any of (1)-(5) above wherein $R^1$ has a fluorophore that serves as a fluorescence resonance energy transfer (FRET) donor;

(7) the fluorescent probe according to any of (1)-(5) above wherein $R^5$, $R^6$, $R^7$, and $R^8$ have a fluorophore that serves as a fluorescence resonance energy transfer (FRET) donor; and (8) the fluorescent probe according to (6) or (7) above wherein the fluorophore is a compound having a xanthene skeleton.

In another aspect, the present invention provides (9) a method for detecting a compound containing an —SH group using the fluorescent probe according to any of (1)-(8) above;

(10) the detection method according to (9) above wherein the presence of a compound containing an —SH group is detected by observing the fluorescence response or change in absorbance due to a reaction between the compound containing an —SH group and the fluorescent probe;

(11) the detection method according to (10) above wherein the fluorescence response is a change in fluorescence due to fluorescence resonance energy transfer (FRET);

(12) the detection method according to (10) above wherein the fluorescence response is visualized using a fluorescence imaging means;

(13) the detection method according to any of (9)-(12) above wherein the compound containing an —SH group is a compound having a cysteine residue; and

(14) the detection method according to any of (9)-(12) above wherein the compound containing an —SH group is glutathione.

In another aspect, the present invention provides

(15) a kit for detecting a compound containing an —SH group including the fluorescent probe according to any of (1)-(8) above;

(16) the kit according to (15) above wherein the compound containing an —SH group is a compound having a cysteine residue; and

(17) the kit according to (15) above wherein the compound containing an —SH group is glutathione.

Advantages of the Invention

The present invention makes it possible to measure the glutathione concentration in living cells accurately, reversibly, and over time because it makes it possible to detect glutathione by a reversible, concentration-dependent fluorescence response. The detection method of the present invention can be implemented by a microscope capable of performing ordinary cell imaging, and does not require special equipment. In addition, since assay over time is possible, decreases in glutathione and recovery from oxidative stress exposure can be grasped by applying and repeating various types of stimulation in the same cell. The present invention can also be applied to the detection of peptides and compounds having cysteine residues other than glutathione as long as the compound contains an —SH group. The probe developed can be said to have great utility value and economic effect in basic research and in industry.

BEST MODE FOR CARRYING OUT THE INVENTION

Figure 1:
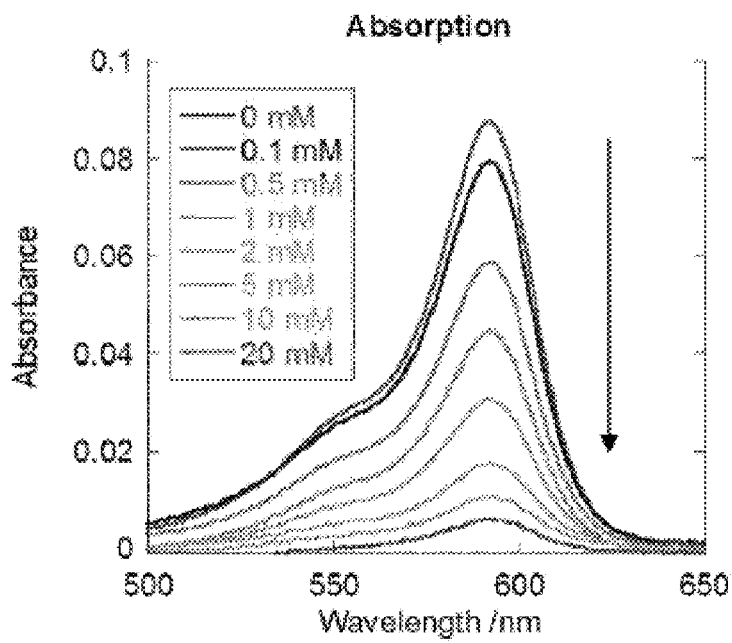
FIG. 1 is a graph showing the changes in the absorption spectrum of "2Me SiR600," which is a fluorescent probe of the present invention, associated with glutathione addition.

Embodiments of the present invention are explained below. The scope of the present invention is not restricted to these explanations; the present invention can be implemented with suitable variations even outside the following examples as long the spirit of the invention is not impaired.

1. Definitions

In this specification, "halogen atom" means a fluorine atom, chlorine atom, bromine atom, or iodine atom.

In this specification, "alkyl" may be any straight-chained, branched, cyclic, or combination thereof aliphatic hydrocarbon group. The number of carbon atoms in the alkyl group is not particularly restricted, but is, for example, 1-20 ($C_{1-23}$), 3-15 ($C_{3-15}$), or 5-10 ($C_{5-10}$). When a number of carbon atoms is specified, it means an "alkyl" having a number of carbon atoms within that numerical range. For example, $C_{1-8}$ alkyls include methyl, ethyl, n-propyl, isopropyl, n-butyl, isobutyl, sec-butyl, tert-butyl, n-pentyl, isopentyl, neo-pentyl, n-hexyl, isohexyl, n-heptyl, n-octyl, and the like. In this specification, an alkyl group may have one or more optional substituents. Examples of substituents include, but are not limited to, an alkoxy group, halogen atom, amino group, mono- or di-substituted amino group, substituted silyl group, or acyl, or the like. When an alkyl group has two or more substituents, they may be the same or different. The same is also true for the alkyl moiety of other substituents (for example, an alkoxy group, arylalkyl group, or the like) including an alkyl moiety.

In this specification, when certain functional groups are defined as "optionally substituted," the type of substituent, substitution position, and number of substituents are not particularly restricted. When there are two or more substituents, they may be the same or different. Examples of substituents include, but are not limited to, an alkyl group, alkoxy group, hydroxyl group, carboxyl group, halogen atom, sulfo group, amino group, alkoxycarbonyl group, oxo group, or the like. Other substituents may be present in these substituents. Examples of such cases include, but are not limited to, an alkyl halide group, dialkylamino group, or the like.

In this specification, "alkenyl" means a straight-chain or branched hydrocarbon group having at least one carbon-carbon double bond. Non-limiting examples include vinyl, allyl, 1-propenyl, isopropenyl, 1-butenyl, 2-butenyl, 3-butenyl, 1,3-butanedienyl, 1-pentenyl, 2-pentenyl, 3-pentenyl, 4-pentenyl, 1,3-pentanedienyl, 1-hexenyl, 2-hexenyl, 3-hexenyl, 4-hexenyl, 5-hexenyl, and 1,4-hexanedienyl. The double bond may have either a cis conformation or trans conformation.

In this specification, "alkynyl" means a straight-chain or branched hydrocarbon group having at least one carbon-carbon triple bond. Non-limiting examples include ethynyl, propynyl, 2-butynyl, and 3-methylbutynyl.

In this specification, "cycloalkyl" means a monocyclic or polycyclic non-aromatic ring system composed of the above alkyls. This cycloalkyl can be unsubstituted or substituted by one or more substituents which may be the same or different. Non-limiting examples of monocyclic cycloalkyls include cyclopropyl, cyclopentyl, cyclohexyl, and cyclopentyl. Non-limiting examples of polycyclic cycloalkyls include 1-decalinyl, 2-decalinyl, norbornyl, adamantyl, and the like. This cycloalkyl may also be a heterocycloalkyl including one or more hetero atoms (for example, an oxygen atom, nitrogen atom, or sulfur atom) as ring constituent atoms. Any —NH in the heterocycloalkyl ring may be protected, for example, as an —N(Boc) group, —N(CBz) group, or —N(Tos) group, and nitrogen atoms or sulfur atoms in the ring may be oxidized to the corresponding N-oxide, S-oxide, or S,S-dioxide. Non-limiting examples of monocyclic heterocycloalkyls include diazapanyl, piperidinyl, pyrrolidinyl, piperazinyl, morpholinyl, thiomorpholinyl, thiazolidinyl, 1,4-dioxanyl, tetrahydrofuranyl, tetrahydropyranyl, tetrahydrothiophenyl, lactam, and lactone.

In this specification, "cycloalkenyl" means a monocyclic or polycyclic non-aromatic ring system including at least one carbon-carbon double bond. This cycloalkenyl can be unsubstituted or substituted by one or more substituents which may be the same or different. Non-limiting examples of monocyclic cycloalkenyls include cyclopentenyl, cyclohexenyl, and cyclohepta-1,3-dienyl. Non-limiting examples of polycyclic cycloalkenyls include norbornylenyl. This cycloalkenyl may also be a heterocycloalkenyl including one or more hetero atoms (for example, an oxygen atom, nitrogen atom, or sulfur atom) as ring constituent atoms, and nitrogen atoms or sulfur atoms in the heterocycloalkenyl ring may be oxidized to the corresponding N-oxide, S-oxide, or S,S-dioxide.

In this specification, "aryl" may be either a monocyclic or fused polycyclic aromatic hydrocarbon group, or an aromatic heterocyclic group including one or more hetero atoms (for example, an oxygen atom, nitrogen atom, or sulfur atom) as ring constituent atoms. In this case, it is also sometimes called "heteroaryl" or "heteroaromatic." When an aryl is monocyclic or a fused ring, it can bond at all possible positions. Non-limiting examples of monocyclic aryls include a phenyl group (Ph), thienyl group (2- or 3-thienyl group), pyridyl group, furyl group, thiazolyl group, oxazolyl group, pyrazolyl group, 2-pyrazinyl group, pyrimidinyl group, pyrrolyl group, imidazolyl group, pyridazinyl group, 3-isothiazolyl group, 3-isooxazolyl group, 1,2,4-oxadiazol-5-yl group, or 1,2,4-oxadiazol-3-yl group. Non-limiting examples of fused polycyclic aryls include a 1-naphthyl group, 2-naphthyl group, 1-indenyl group, 2-indenyl group, 2,3-dihydroinden-1-yl group, 2,3-dihydroinden-2-yl group, 2-anthryl group, indazolyl group, quinolyl group, isoquinolyl group, 1,2-dihydroisoquinolyl group, 1,2,3,4-tetrahydroisoquinolyl group, indolyl group, isoindolyl group, phthalazinyl group, quinoxalinyl group, benzofuranyl group, 2,3-dihydrobenzofuran-1-yl group, 2,3-dihydrobenzofuran-2-yl group, 2,3-dihydrobenzothiophen-1-yl group, 2,3-dihydrobenzothiophen-2-yl group, benzothiazolyl group, benzimidazolyl group, fluorenyl group, or thioxanthenyl group. In this specification, an aryl group may have one or more optional substituents on the ring. Examples of these substituents include, but are not limited to, an alkoxy group, halogen atom, amino group, mono- or di-substituted amino group, substituted silyl group, or acyl group. When an aryl group has two or more substituents, they may be the same or different. The same is also true for the aryl moiety of other substituents (for example, an aryloxy group, arylalkyl group, or the like) including an aryl moiety.

In this specification, "arylalkyl" represents an alkyl substituted by the above aryl. An arylalkyl may have one or more optional substituents. Examples of these substituents include, but are not limited to, an alkoxy group, halogen atom, amino group, mono- or di-substituted amino group, substituted silyl group, or acyl group. When an acyl group has two or more substituents, they may be the same or different. Non-limiting examples of arylalkyls include a benzyl group, 2-thienylmethyl group, 3-thienylmethyl group, 2-pyridylmethyl group, 3-pyridylmethyl group, 4-pyridylmethyl group, 2-furylmethyl group, 3-furylmethyl group, 2-thiazolylmethyl group, 4-thiazolylmethyl group, 5-thiazolylmethyl group, 2-oxazolylmethyl group, 4-oxazolylmethyl group, 5-oxazolylmethyl group, 1-pyrazolylmethyl group, 3-pyrazolylmethyl group, 4-pyrazolylmethyl group, 2-pyrazinylmethyl group, 2-pyrimidinylmethyl group, 4-pyrimidinylmethyl group, 5-pyrimidinylmethyl group, 1-pyrrolylmethyl group, 2-pyrrolylmethyl group, 3-pyrrolylmethyl group, 1-imidazolylmethyl group, 2-imidazolylmethyl group, 4-imidazolylmethyl group, 3-pyridazinylmethyl group, 4-pyridazinylmethyl group, 3-isothiazolylmethyl group, 3-isoxazolylmethyl group, 1,2,4-oxadiazol-5-ylmethyl group, or 1,2,4-oxadiazol-3-ylmethyl group.

Similarly, in this specification, "arylalkenyl" represents an alkenyl substituted by the above aryl.

In this specification, "alkoxy group" is a structure in which the above alkyl group is bonded to an oxygen atom.

Examples include saturated alkoxy groups having a straight-chain, branched, or cyclic configuration or a combination of such configurations. For example, a methoxy group, ethoxy group, n-propoxy group, isopropoxy group, cyclopropoxy group, n-butoxy group, isobutoxy group, s-butoxy group, t-butoxy group, cyclobutoxy group, cyclopropylmethoxy group, n-pentyloxy group, cyclopentyloxy group, cyclopropylethyloxy group, cyclobutylmethyloxy group, n-hexyloxy group, cyclohexyloxy group, cyclopropylpropyloxy group, cyclobutylethyloxy group, or cyclopentylmethyloxy group can be given as suitable examples.

In this specification, "aryloxy group" is a group in which the above aryl groups are bonded via oxygen atoms. Examples of aryloxy groups include a phenoxy group, 2-thienyloxy group, 3-thienyloxy group, 2-pyridyloxy group, 3-pyridyloxy group, 4-pyridyloxy group, 2-furyloxy group, 3-furyloxy group, 2-thiazolyloxy group, 4-thiazolyloxy group, 5-thiazolyloxy group, 2-oxazolyloxy group, 4-oxazolyloxy group, 5-oxazolyloxy group, 1-pyrazolyloxy group, 3-pyrazolyloxy group, 4-pyrazolyloxy group, 2-pyrazinyloxy group, 2-pyrimidinyloxy group, 4-pyrimidinyloxy group, 5-pyrimidinyloxy group, 1-pyrrolyloxy group, 2-pyrrolyloxy group, 3-pyrrolyloxy group, 1-imidazolyloxy group, 2-imidazolyloxy group, 4-imidazolyloxy group, 3-pyridazinyloxy group, 4-pyridazinyloxy group, 3-isothiazolyloxy group, 3-isoxazolyloxy group, 1,2,4-oxadiazol-5-yloxy group, or 1,2,4-oxadiazol-3-yl group.

In this specification, "alkylene" is a divalent group composed of a straight-chain or branched saturated hydrocarbon. Examples include methylene, 1-methylmethylene, 1,1-dimethylmethylene, ethylene, 1-methylethylene, 1-ethylethylene, 1,1-dimethylethylene, 1,2-dimethylethylene, 1,1-diethylethylene, 1,2-diethylethylene, 1-ethyl-2-methylethylene, trimethylene, 1-methyltrimethylene, 2-methyltrimethylene, 1,1-dimethyltrimethylene, 1,2-dimethyltrimethylene, 2,2-dimethyltrimethylene, 1-ethyltrimethylene, 2-ethyltrimethylene, 1,1-diethyltrimethylene, 1,2-diethyltrimethylene, 2,2-diethyltrimethylene, 2-ethyl-2-methyltrimethylene, tetramethylene, 1-methyltetramethylene, 2-methyltetramethylene, 1,1-dimethyltetramethylene, 1,2-dimethyltetramethylene, 2,2-dimethyltetramethylene, 2,2-di-n-propyltrimethylene, and the like.

In this specification, "alkenylene" is a divalent group composed of a straight-chain or branched unsaturated hydrocarbon having at least one carbon-carbon double bond. Examples include ethenylene, 1-methylethenylene, 1-ethylethenylene, 1,2-dimethylethenylene, 1,2-diethylethenylene, 1-ethyl-2-methylethenylene, propenylene, 1-methyl-2-propenylene, 2-methyl-2-propenylene, 1,1-dimethyl-2-propenylene, 1,2-dimethyl-2-propenylene, 1-ethyl-2-propenylene, 2-ethyl-2-propenylene, 1,1-diethyl-2-propenylene, 1,2-diethyl-2-propenylene, 1-butenylene, 2-butenylene, 1-methyl-2-butenylene, 2-methyl-2-butenylene, 1,1-dimethyl-2-butenylene, 1,2-dimethyl-2-butenylene, and the like.

In this specification, "arylene" and "arylalkylene" mean divalent groups based on the above "aryl" and "arylalkyl," respectively. Similarly, "oxyalkylene" and "aryleneoxy" mean divalent groups based on the above "alkoxy" and "aryloxy," respectively.

In this specification, "alkylamino" and "arylamino" mean amino groups in which hydrogen atoms of the —NH$_2$ group have been substituted by one or two of the above alkyls or aryls. Examples include methylamino, dimethylamino, ethylamino, diethylamino, ethylmethylamino, benzylamino, and the like. Similarly, "alkylthio" and "arylthio" mean groups in which hydrogen atoms of the —SH group have been substituted by the above alkyls or aryls. Examples include methylthio, ethylthio, benzylthio, and the like.

The term "amide" used in this specification includes both RNR'CO— (when R=alkyl, alkaminocarbonyl-) and RCONR'— (when R=alkyl, alkylcarbonylamino-).

The term "ester" used in this specification includes both ROCO— (when R=alkyl, alkoxycarbonyl-) and RCOO— (when R=alkyl, alkylcarbonyloxy-).

In this specification, the phrase "ring structure" means a heterocyclic or carbocyclic group when formed by a combination of two substituents. Such groups may be saturated, unsaturated, or aromatic. Therefore, it includes the cycloalkyls, cycloalkenyls, aryls, and heteroaryls defined above. Examples include cycloalkyl, phenyl, naphthyl, morpholinyl, piperidinyl, imidazolyl, pyrrolidinyl, and pyridyl. In this specification, substituents can form ring structures with other substituents, and those skilled in the art can understand that a specific substitution, for example, bonding to hydrogen, is formed when such substituents bond to each other. Therefore, when it is stated that specific substituents together form a ring structure, those skilled in the art can understand that this ring structure can be formed by an ordinary chemical reaction or is generated easily. Any such ring structures and their formation processes are within the purview of those skilled in the art.

2. Fluorescent Probe for Detecting an —SH Group-Containing Compound of the Present Invention The fluorescent probe of the present invention, in one embodiment, includes a compound having a structure represented by formula (I).

[Chemical formula 2]

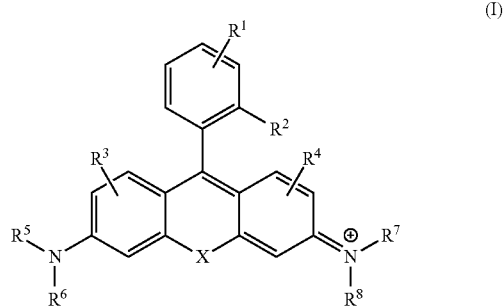

In formula (I), X represents Si(R$^a$)(R$^b$), Ge(R$^a$)(R$^b$), Sn(R$^a$)(R$^b$), or C(R$^a$)(R$^b$). Here, R$^a$ and R$^b$ each independently represent a hydrogen atom or alkyl group. When R$^a$ and R$^b$ are alkyl groups, they can have one or more substituents. They may have, for example, one or more alkyl groups, alkoxy groups, halogen atoms, hydroxyl groups, carboxyl groups, amino groups, sulfo groups, or the like as substituents. R$^a$ and R$^b$ are preferably both methyl groups.

Alternatively, in some cases, $R^a$ and $R^b$ may bond together and form a ring structure. For example, when $R^a$ and $R^b$ are both alkyl groups, $R^a$ and $R^b$ can bond together to form a spiro carbon ring. The ring formed is preferably, for example, an about 5- to 8-membered ring. X is preferably $Si(R^a)(RD)$, more preferably $Si(CH_3)_2$.

$R^1$ represents a hydrogen atom, or 1-4 identical or different substituents selected independently from the group consisting of a cyano group, alkyl group, carboxyl group, ester group, alkoxy group, amide group, or azide group, each of which may be optionally substituted (for example, a haloalkyl such as fluoroalkyl can be included in "optionally substituted alkyl groups"). When $R^1$ is other than a hydrogen atom, its position on the benzene ring is not particularly restricted, but $R^1$ is preferably in a meta position to the substituent having $R^2$. In addition, when there are two or more substituents on the benzene ring, they may be the same or different. $R^1$ is preferably, for example, an iminodiacetic acid ester from the viewpoint of suppressing localization of the probe molecule within the cell.

In addition, as will be described below, $R^1$ can also have a fluorophore that serves as a fluorescence resonance energy transfer (FRET) donor. In this case, an amide group is typically suitable as $R^1$. A fluorophore known in technical fields related to FRET can be used as long as it is a fluorophore having the rhodamine-like skeleton site in formula (I) as an acceptor and can serve as a donor thereto. Non-limiting examples include pyrene, perylene, coumarin, fluorescein, rhodamine, cyanine, boron dipyromethene (BO-DIPY), oxazine, and the like. Such fluorophores are preferably compounds having a xanthene skeleton.

$R^2$ represents a hydrogen atom, halogen atom, hydroxyl group, cyano group, or an alkyl group, alkynyl group, alkoxy group, aryl, or heteroaryl, each of which may be optionally substituted. Preferred are a hydroxyl group, cyano group, or a $C_1$-$C_4$ alkyl group, $C_1$-$C_4$ alkoxy group, or phenyl group, each of which may be optionally substituted. More preferred are a hydroxyl group, cyano group, methyl group, and methoxy group.

$R^3$ and $R^4$ each independently represent a hydrogen atom, or 1-3 identical or different substituents independently selected from the group consisting of a hydroxyl group, halogen atom, or an alkyl group, sulfo group, carboxyl group, ester group, amide group, and azide group, each of which may be optionally substituted. $R^3$ and $R^4$ preferably are both hydrogen atoms. In addition, as with $R^1$, $R^3$ and $R^4$ can also have a fluorophore that serves as a fluorescence resonance energy transfer (FRET) donor.

$R^5$, $R^6$, $R^7$, and $R^8$ each independently show a hydrogen atom or alkyl group. As with $R^1$, $R^5$, $R^6$, $R^7$, and $R^8$ can also have a fluorophore that serves as a fluorescence resonance energy transfer (FRET) donor. Here, when either $R^5$ or $R^6$ is an alkyl group, it may, together with $R^3$, form a ring structure including the nitrogen atoms bonded thereto. In this case, only one or the other combination of $R^5$ and $R^3$ or $R^6$ and $R^3$ may form a ring structure, or both may form a ring structure. This ring structure can also include hetero atoms other than the abovementioned nitrogen atoms.

Similarly, when either $R^7$ or $R^8$ is an alkyl group, it may, together with $R^4$, form a ring structure including the nitrogen atoms bonded thereto. In this case, only one or the other combination of $R^7$ and $R^4$ or $R^8$ and $R^4$ may form a ring structure, or both may form a ring structure. This ring structure can also include hetero atoms other than the abovementioned nitrogen atoms.

Concrete examples of compounds of formula (I) especially suitable as a probe for fluorescence imaging of an —SH group-containing compound of the present invention include

[Chemical formula 3]

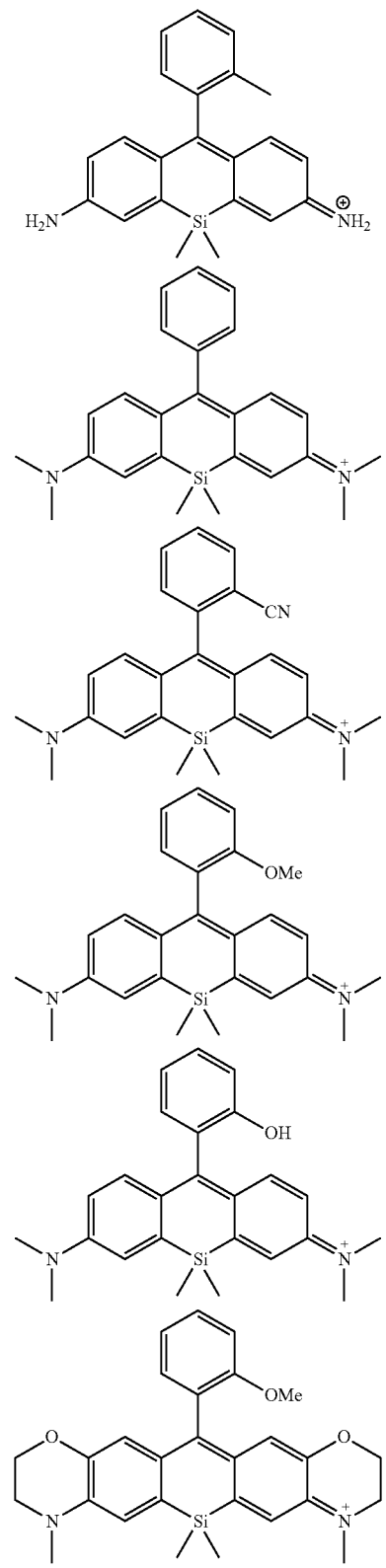

-continued

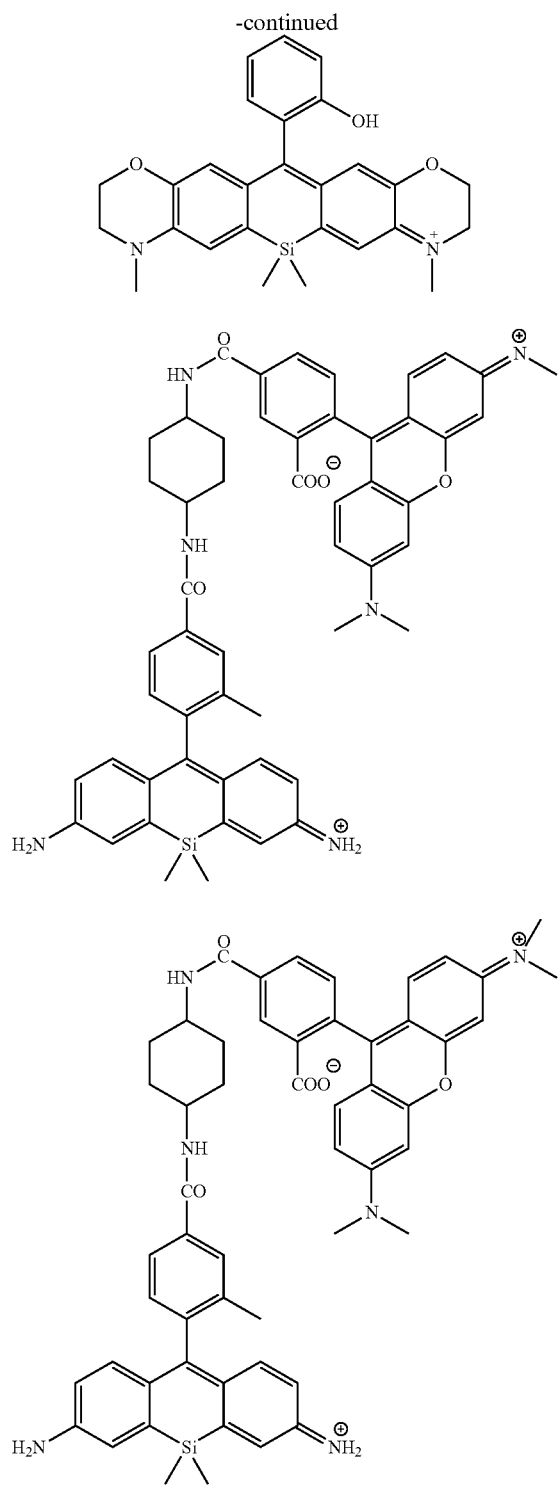

However, they are not limited to these.

Compounds represented by formula (I) usually exist as salts because they have a monovalent positive charge in the N atom linking $R^7$ and $R^8$. Examples of such salts include base addition salts, acid addition salts, and amino acid salts. Examples of base addition salts include sodium salts, potassium salts, calcium salts, magnesium salts, and other such metal salts, ammonium salts, and triethylamine salts, piperidine salts, morpholine salts, and other such organic amine salts. Examples of acid addition salts include hydrochlorides, sulfates, nitrates, and other such mineral acid salts, trifluoroacetates and other such carboxylates, methanesulfonates, p-toluenesulfonates, citrates, succinates, and other such organic acid salts. Glycine salts and the like can be given as an example of amino acid salts. However, salts are not limited to these.

Compounds represented by formula (I) sometimes have one or more asymmetric carbons depending on the types of substituents, and sometimes exist as optical isomers, diastereomers, or other such stereoisomers. Stereoisomers of a pure form, any mixtures of stereoisomers, racemates, and the like are all encompassed within the scope of the present invention.

Compounds represented by formula (I) or salts thereof can also exist as hydrates or solvates. These substances are all encompassed within the scope of the present invention. The type of solvent for forming a solvate is not particularly restricted; examples include ethanol, acetone, isopropanol, and other such solvents.

The above fluorescent probe may be used as a composition by compounding with additives commonly used in the preparation of reagents as needed. For example, dissolution auxiliaries, pH adjusters, buffers, isotonifying agents, and other such additives can be used as additives for use in a physiological environment, and the amounts compounded can be selected as is appropriate by one skilled in the art. These compositions can be provided as a composition of a suitable form such as a mixture in powdered form, freeze-dried product, granules, tablets, liquid, or the like.

Since methods of producing typical compounds encompassed among compounds of the present invention represented by formula (I) are illustrated concretely in examples in this specification, any compounds encompassed by formula (I) can be produced easily by one skilled in the art by selecting the starting raw materials as needed and reagents, reaction conditions, and the like as appropriate using the disclosure of this specification as a reference.

3. Method for Detecting—SH Group-Containing Compounds Using a Fluorescent Probe of the Present Invention The fluorescent probe of the present invention is one that uses a mechanism whereby both the visible light region absorption and fluorescence are eliminated when position 9 of a xanthene-like fused ring shown by formula (I) undergoes nucleophilic attack by the thiol (SH) groups in glutathione or the like, as shown below (here, a compound containing an —SH group such as glutathione is shown as "R-SH"). This reaction is reversible. This makes it possible to detect compounds having an —SH group such as glutathione reversibly, over time, and quantitatively. Furthermore, examples of this "compound including an —SH group" are not limited to the glutathione given here as an example, but can include a wide range of compounds and peptides having cysteine residues, and the fluorescent probe of the present invention can be applied to these compounds as well as long as the following reaction advances.

[Chemical formula 4]

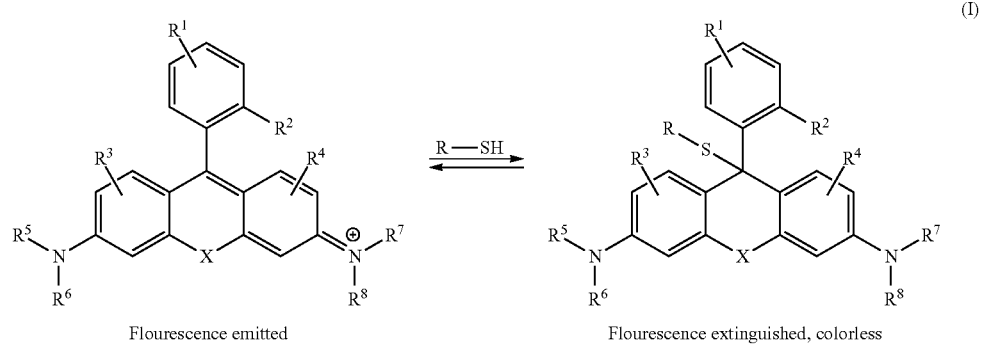

Flourescence emitted             Flourescence extinguished, colorless

In addition, by providing a fluorophore capable of serving as a donor of fluorescence resonance energy transfer (FRET), the reaction with an —SH group-containing compound can also be detected as a change in emission wavelength by fluorescence resonance energy transfer (FRET) in which the rhodamine-like skeleton of formula (I) serves as the acceptor. Specifically, emission is seen at a fluorescence wavelength unique to the rhodamine-like skeleton in an environment where no —SH group-containing compound is present, but the —SH group-containing compound can be detected as a fluorescence emission because the fluorescence from the rhodamine-like skeleton is extinguished and emission increases at a fluorescence wavelength unique to the donor fluorophore due to reaction of a compound of formula (I) and an —SH group-containing compound. It is therefore preferable that the fluorescence spectrum of the donor fluorophore overlap the absorption spectrum of the rhodamine-like skeleton, or that the fluorescence wavelength of the donor fluorophore is in a wavelength range different from the fluorescence wavelength of the rhodamine-like skeleton. As described above, such a donor fluorophore can be present in any of $R^1$, $R^3$-$R^8$ in formula (I), preferably in $R^1$, $R^5$, $R^6$, $R^7$, or $R^8$.

In accordance with the above emission mechanism, the method for detecting an —SH group-containing compound of the present invention is characterized by detecting the presence of a compound containing an —SH group by observing a fluorescence response or change in absorbance due to the reaction of a compound containing an SH group and the above fluorescent probe. The term "detection" in this specification can be interpreted in the broadest sense to include measurement for various purposes such as quantitative and qualitative. As mentioned above, this fluorescence response is preferably a change in fluorescence due to the fluorescence resonance energy transfer (FRET).

A fluorometer having a wide measurement wavelength can be used as the means for observing the fluorescence response, but the fluorescence response can also be visualized using a fluorescence imaging means that permits display as a two-dimensional image. Since the fluorescence response can be visualized two-dimensionally by using a fluorescence imaging means, it becomes possible to view glutathione or the like instantaneously. Devices known in the art can be used as the fluorescence imaging device.

Typical examples of the means of bringing the —SH group-containing compound sample that is the object of measurement and the fluorescent probe into contact include adding, applying, or spraying a solution including the fluorescent probe on a sample. Nonetheless, a suitable means can be selected in accordance with the form of the sample, the measurement environment, or the like.

The use concentration of the fluorescent probe of the present invention is not particularly restricted, but a solution having a concentration of about 0.1-1.0 μM, for example, can be used.

A compound represented by formula (I) or a salt thereof can be used without further modification as a fluorescent probe of the present invention, but may be used in the form of a composition compounded with additives commonly used in the preparation of reagents as needed. For example, dissolution auxiliaries, pH adjusters, buffers, isotonifying agents, and other such additives can be used as additives for use in a physiological environment, and the amounts compounded can be selected as is appropriate by one skilled in the art. These compositions can be provided as a composition of a suitable form such as a mixture in powdered form, freeze-dried product, granules, tablets, liquid, or the like, but should be used dissolved in distilled water for injection or a suitable buffer at the time of use.

4. Kit for Detecting an —SH Group-Containing Compound Using a Fluorescent Probe of the Present Invention It is preferable to use a kit for detecting an —SH group-containing compound including the fluorescent probe in the detection method of the present invention. The fluorescent probe of the present invention is usually prepared as a solution in this kit, but it can also be provided as a composition of a suitable form such as a mixture in powdered form, freeze-dried product, granules, tablets, liquid, or the like, and can be used dissolved in distilled water for injection or a suitable buffer at the time of use.

This kit may also include other reagents and the like as needed. For example, dissolution auxiliaries, pH adjusters, buffers, isotonifying agents, and other such additives can be used as additives, and the amounts compounded can be selected as appropriate by one skilled in the art.

EXAMPLES

The present invention is explained in greater detail below through examples, but the invention is not limited to these examples.

[Reagents, Instruments, Etc.]

All of the organic solvents used in the reactions shown below were of dehydration grade. Commercial raw materials were purchased from the reagent manufacturers (Wako Pure Chemical Industries, Ltd., Tokyo Chemical Industry Co., Ltd., Kanto Chemical Co., Inc., Sigma-Aldrich Co., Ltd., Acros Co., Ltd.).

The following devices and columns were used in purification by high-performance liquid chromatography.

Pump: PU-2080 and PU-2087 (JASCO Co., Ltd.)

Detector: MD-2010 (JASCO Co., Ltd.)

Column: Inertsil ODS-3 (10×250 mm or 20×250 mm, GL Science Inc.)

Unless stated otherwise, the following solvents A and B were used during separation and purification by HPLC, and purification was carried out by mixing them in any composition.

A: Purified water (containing 1% acetonitrile, 0.1% trifluoroacetic acid)

B: Acetonitrile (containing 1% purified water)

C: Purified water (containing 0.2 M acetic acid-triethylamine)

Solution feed in HPLC separation was conducted respectively at 25 mL/min (pump: PU-2087, column: 20×250 mm), 5 mL/min (pump: PU-2080, column: 10×250 mm), and 1 mL/min (pump: PU-2080, column: 4.6×200 mm). Purification by medium-pressure column chromatography was conducted using a YFLC-A1580 (Yamazen Co., Ltd.).

NMR measurement was conducted using an AVANCE III 400 Nanobay (Bruker Co., Ltd.) (400 MHz for 1H NMR, 101 MHz for 13C NMR). Mass spectrometry measurement was conducted using a MicrOTOF (ESI-TOF, Bruker Co., Ltd.). Sodium formate was used as an external standard during high-resolution MS (HRMS) measurement.

Example 1

1. Synthesis of Fluorescent Probes

Synthesis of Compound 1 (2Me SiR600)

Compound 1 (2Me SiR600), which is a fluorescent probe of the present invention, was synthesized according to scheme 1 below. Furthermore, the synthesis of compound A2 is disclosed in Kushida K., et al., Bioorg. Med. Chem. Lett. 22(2012) 3908-3911, and synthesis was conducted based on that publication.

Scheme 1

[Chemical formula 15]

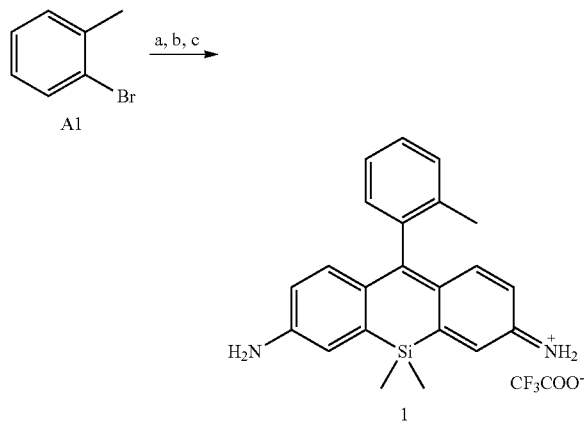

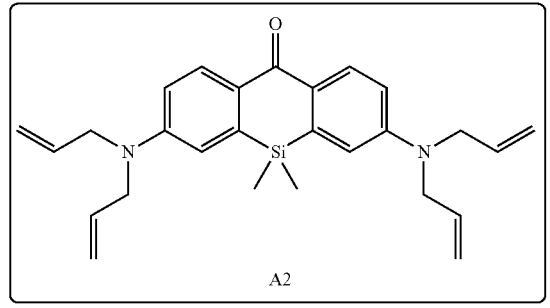

a) i) -78° C., THF, ii) compound A2 in THF, -78° C. to rt., iii) 1N HClaq.
b) NaBH$_4$, MeOH, rt.,
c) 1,3-dimethylbarbituric acid, Pd(PPh$_3$)$_4$, CH$_2$Cl$_2$, 35° C.,
d) p-chloranil, CH$_2$Cl$_2$, rt.

2-Bromotoluene (compound A1, 34.2 mg, 0.2 mmol, 6 Eq) was dissolved in THF (5 mL), and stirred for 10 minutes at −78° C. in an argon atmosphere. 1 M sec-butyllithium cyclohexane/n-hexane solution (0.2 mL, 0.2 mmol, 6 Eq) was added slowly, and stirred for 10 minutes. Compound A2 (14.5 mg, 0.034 mmol, 1 Eq) was added upon being dissolved in THF (3 mL), and stirred for one hour at −78° C. and for two hours at room temperature. The solution was acidified by adding 1N hydrochloric acid, and saturated sodium hydrogen carbonate aqueous solution was then added. The reaction system was extracted twice by dichloromethane, and the organic phase obtained was washed by saturated saline, dried by anhydrous sodium sulfate, and the solvent was removed under reduced pressure. The residue obtained was purified by HPLC (A/B=90/10 to 10/90, 45 min), and compound A3 (13.3 mg, 73.0%) was obtained as a blue solid. Compound A3 (7.7 mg, 0.014 mmol) was then dissolved in methanol (5 mL) and placed on an ice bath. Next, sodium borohydride was added gradually, and the reaction was completed by adding water when the dark blue solution became colorless. The reaction system was then extracted by adding dichloromethane, and the organic phase was washed by water and saturated saline, dried by anhydrous sodium sulfate, the solvent was distilled off under reduced pressure, and the residue was vacuum dried. The residue obtained was dissolved in deoxygenated dichloromethane (5 mL), and added to a test tube containing 1,3-dimethylbarbituric acid (54.3 mg, 0.35 mmol, 24 Eq) and tetrakis(triphenylphosphine)palladium (3.2 mg, 0.0028 mmol, 0.2 Eq), and stirred for 60 minutes at 35° C. in an argon atmosphere. Chloranil (5.0 mg, 0.02 mmol, 1.5 Eq) was also added, and stirred for 60 minutes at room temperature. After distilling off the solvent under reduced pressure, the residue was purified by HPLC (A/B=90/10 to 10/90, 45 min), and the target compound 1 (1.2 mg, 18.4%) was obtained as a bluish-violet solid.

Synthesis of Compound 2 (pH SiR650)

Compound 2 (Ph SiR650), which is a fluorescent probe of the present invention, was synthesized according to scheme 2 below. Furthermore, the synthesis of compound B1 is disclosed in Y. Koide et al., J. Am. Chem. Soc. 2012, 134, 5029-5031, and synthesis was conducted based on that publication.

Scheme 2

[Chemical formula 16]

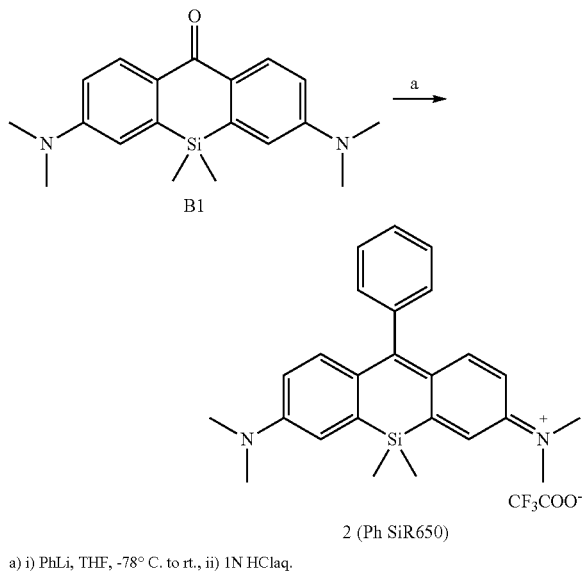

a) i) PhLi, THF, -78° C. to rt., ii) 1N HClaq.

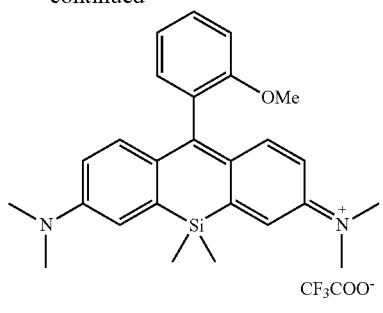

a) i) -78° C., THF, ii) compound B1 in THF, -78° C. to rt., iii) 1N HClaq.

Compound B1 (12.5 mg, 0.039 mmol, 1.0 Eq) was dissolved in THF (2 mL), and stirred at -78° C. in an argon atmosphere. 1.9 M phenyllithium dibutyl ether solution (100 µL, 0.193 mmol, 5.0 Eq) was added slowly, and stirred for 10 minutes at -78° C. and for two hours at room temperature. The solution was acidified by adding 1N hydrochloric acid, and saturated sodium hydrogen carbonate aqueous solution was then added. The reaction system was extracted twice by dichloromethane, and the organic phase obtained was washed by saturated saline, dried by anhydrous sodium sulfate, and the solvent was removed under reduced pressure. The residue obtained was purified by HPLC (A/B=90/10 to 10/90, 25 min), and the target compound 2 (15.8 mg, 82%) was obtained as a blue solid.

$^1$H NMR (CD$_3$OD): δ 7.58-7.56 (m, 3H), 7.36 (d, J=2.8 Hz, 2H), 7.29-7.26 (m, 2H), 7.15 (d, J=9.6 Hz, 2H), 6.77 (dd, J=9.6 Hz, 2.8 Hz, 2H), 3.34 (s, 12H), 0.60 (s, 3H); $^{13}$C NMR (CD$_3$OD): δ 171.1 (C), 155.7 (C), 149.6 (C), 143.3 (CH), 140.6 (C), 130.4 (CH), 129.8 (CH), 129.3 (CH), 129.0 (C), 122.1 (CH), 114.8 (CH), 40.8 (CH$_3$), -1.1 (CH$_3$); HRMS-ESI (m/z): [M]$^+$ calcd for C$_{25}$H$_{29}$N$_2$Si: 385.20945; found: 385.20719 (2.3 mDa, 5.9 ppm).

Synthesis of Compound 3 (2OMe SiR650)

Compound 3 (2OMe SiR650), which is a fluorescent probe of the present invention, was synthesized according to scheme 3 below.

Scheme 3

[Chemical formula 17]

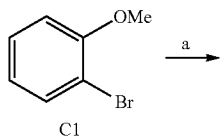

2-Bromoanisole (compound C1, 50 mg, 0.293 mmol, 8.4 Eq) was dissolved in THF (2 mL), and stirred for 10 minutes at -78° C. in an argon atmosphere. 1 M sec-butyllithium cyclohexane/n-hexane solution (250 µL, 0.250 mmol, 7.1 Eq) was added slowing, and stirred for 10 minutes. Compound B1 (10 mg, 0.035 mmol, 1 Eq) was added upon being dissolved in THF (2 mL), and stirred for one hour at -78° C. and for six hours at room temperature. The solution was acidified by adding 1N hydrochloric acid, and saturated sodium hydrogen carbonate was then added. The reaction system was extracted twice by dichloromethane, and the organic phase obtained was washed by saturated saline, dried by anhydrous sodium sulfate, and the solvent was removed under reduced pressure. The residue obtained was purified by HPLC (A/B=90/10 to 10/90, 25 min), and the target compound 3 (15.3 mg, 94%) was obtained as a blue solid.

$^1$H NMR (CD$_3$OD): δ 7.56 (dt, J=7.4 Hz, 1.8 Hz, 1H), 7.32 (d, J=2.8 Hz, 2H), 7.22-7.16 (m, 3H) 7.15 (d, J=7.4 Hz, 1H), 7.08 (dd, J=7.4 Hz, 1.8 Hz, 1H), 6.75 (dd, J=9.6 Hz, 2.8 Hz, 2H), 3.71 (s, 3H), 3.34 (s, 12H), 0.61 (s, 3H), 0.58 (s, 3H); $^{13}$C NMR (CD$_3$OD) δ 169.5, 158.1, 155.7, 149.4, 142.7, 131.8, 131.4, 129.2, 129.1, 121.8, 121.4, 114.9, 112.3, 56.2, 40.8, -1.0, -1.4 ppm.

Synthesis of Compound 4 (2OH SiR650)

Compound 4 (2OH SiR650), which is a fluorescent probe of the present invention, was synthesized according to scheme 4 below.

Scheme 4

[Chemical formula 18]

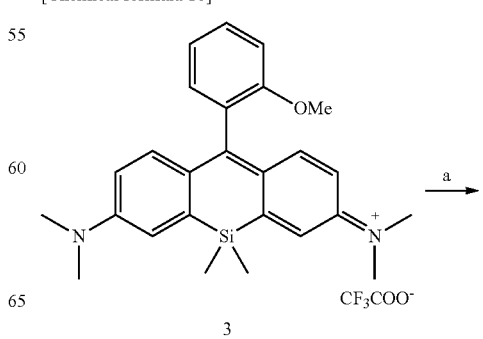

-continued

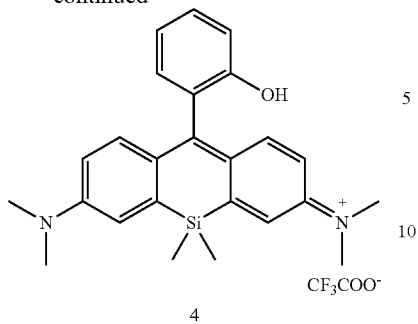

4 a) BBr₃, CH₂Cl₂, −78° C. to rt.

Compound 3 (8.8 mg, 16.7 μmol, 1 Eq) was dissolved in dichloromethane (500 μL), and stirred at −78° C. in an argon atmosphere. Boron tribromide (8 μL, 84.6 μmol, 5.1 Eq) was added slowly, and stirred at −78° C. The reaction system was gradually returned to room temperature, and stirred overnight. Saturated sodium hydrogen carbonate aqueous solution was added. The reaction system was extracted twice by dichloromethane, and the organic phase obtained was washed by saturated saline, dried by anhydrous sodium sulfate, and the solvent was removed under reduced pressure. The residue obtained was purified by HPLC (A/B=90/10- to 10/90, 25 min), and the target compound 4 (8.2 mg, 95%) was obtained as a blue solid.

$^1$H NMR (CD$_3$OD): δ 7.42-7.38 (m, 1H), 7.32 (d, J=2.9 Hz, 2H), 7.28 (d, J=9.6 Hz, 2H), 7.03-7.01 (m, 2H), 6.98 (d, J=8.2 Hz, 1H), 6.77 (dd, J=9.6 Hz, 2.8 Hz, 2H), 3.34 (s, 12H), 0.62 (s, 3H), 0.58 (s, 3H); $^{13}$C NMR (CD$_3$OD) δ 170.2, 155.8, 155.7, 149.6, 143.0, 131.6, 131.5, 129.3, 127.5, 121.8, 120.3, 116.6, 114.9, 40.8, −0.9, −1.4 ppm.

Synthesis of Compound 5 (2CN SiR650)

Compound 5 (2CN SiR650), which is a fluorescent probe of the present invention, was synthesized according to scheme 5 below.

Scheme 5

[Chemical formula 19]

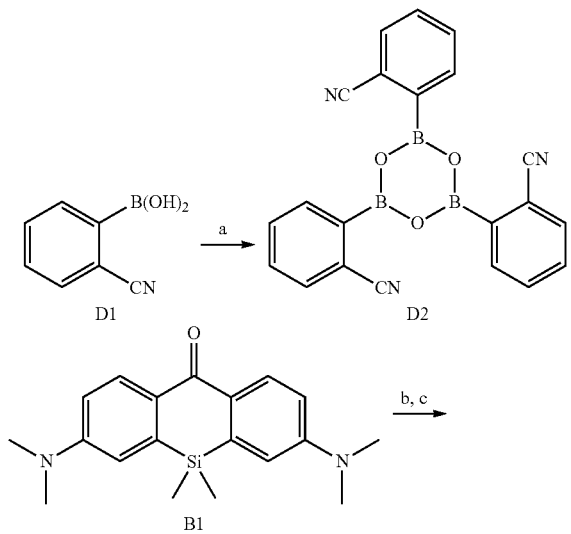

-continued

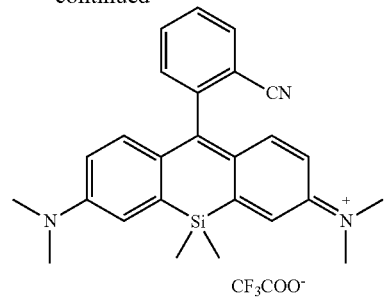

5 (2CN SiR650)

a) 110° C., b) Tf₂O, MeCN, rt, c) compound E2, PdCl₂(PPh₃)₂, Na₂CO₃, MeCN

[Synthesis of Compound D2]

2-Cyanophenylboronic acid (compound D1, 162 mg, 1.10 mmol) was dried under reduced pressure for six hours at 110° C., and compound D2 (140 mg, 0.367 mmol, 100%) was obtained as a white solid. Compound D2 was used in the following reaction without separation or purification.

[Synthesis of Compound 5 (2CN SiR650)]

Compound B1 (55.6 mg, 0.171 mmol, 1 Eq) was dissolved in deoxygenated acetonitrile (10 mL), and stirred at room temperature in an argon atmosphere. Trifluoromethanesulfonic anhydride (40 μL, 0.238 mmol, 1.4 Eq) was added slowly. After stirring for another 15 minutes at room temperature, compound D2 (82.3 mg, 0.210 mmol, 1.2 Eq), bis(triphenylphosphine)palladium(II) dichloride (23.7 mg, 0.034 mmol, 0.2 Eq), and sodium carbonate (53.2 mg, 0.503 mmol, 3.0 Eq) were added and stirred overnight at 60° C. The reaction system was returned to room temperature, the insoluble matter was filtered out by Celite, and the filtrate was distilled off under reduced pressure. The residue obtained was purified by HPLC (A/B=90/10 to 10/90, 25 min), and the target compound 5 (12.4 mg, 13%) was obtained as a blue solid.

$^1$H NMR (CD$_3$OD): δ7.97 (d, J=7.8 Hz, 1H), 7.90 (dt, J=1.2 Hz, 7.7 Hz, 1H), 7.77 (dt, J=1.2 Hz, 7.8 Hz, 1H), 7.53 (d, J=7.7 Hz, 1H), 7.40 (d, J=2.8 Hz, 2H), 6.95 (d, J=9.7 Hz, 2H), 6.81 (dd, J=9.7 Hz, 2.8 Hz, 2H), 3.37 (s, 12H), 0.64 (s, 3H), 0.60 (s, 3H); $^{13}$C NMR (CD$_3$OD): δ 164.8 (C), 155.8 (C), 149.6 (C), 14.4 (C), 141.8 (CH), 134.10 (CH), 134.06 (CH), 131.7 (CH), 130.7 (CH), 128.5 (C), 122.7 (CH), 117.8 (C), 115.5 (CH), 114.4 (C), 41.0 (CH$_3$), −0.8 (CH$_3$), −1.8 (CH$_3$).

Synthesis of Compound 6 (2OMe OxaSiR diMe)

Compound 6 (2OMe OxaSiR diMe), which is a fluorescent probe of the present invention, was synthesized according to scheme 6 below.

Scheme 6

[Chemical formula 20]

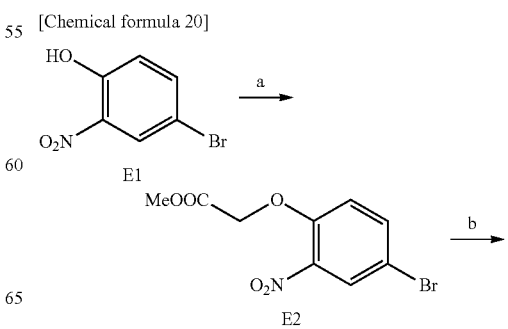

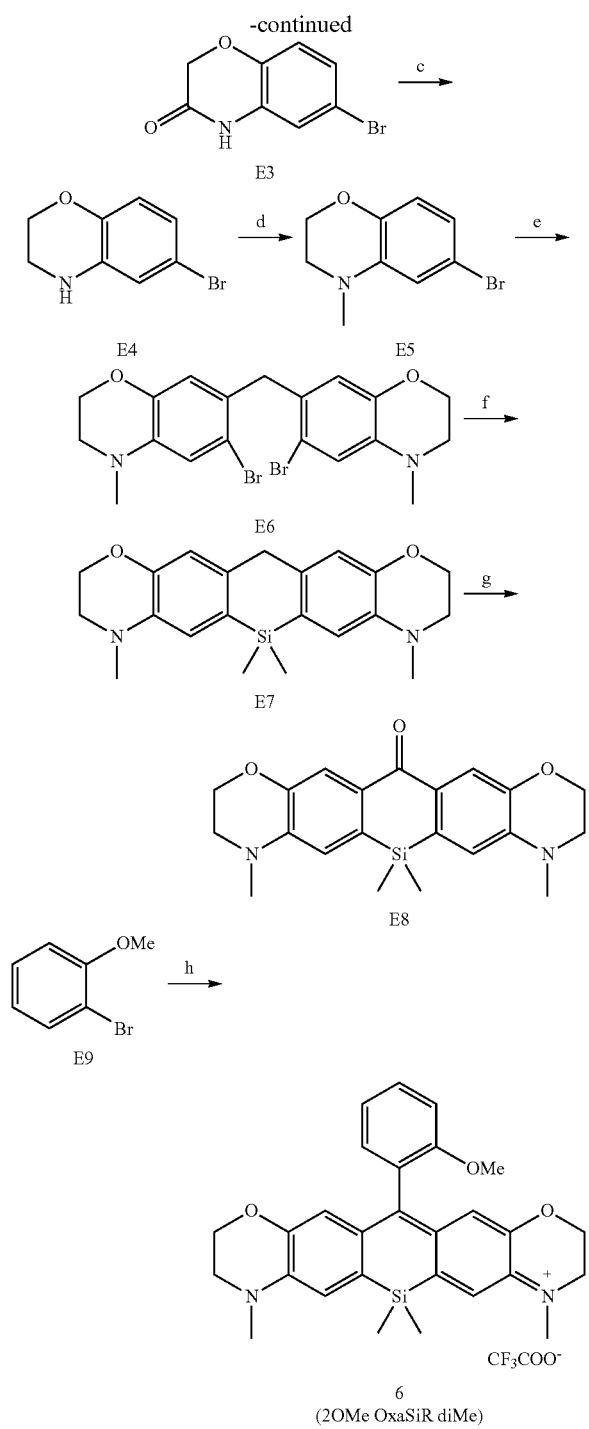

(2OMe OxaSiR diMe)

a) BrCH$_2$COOMe, K$_2$CO$_3$, DMF, 70° C.; b) Fe powder, AcOH, reflux; c) BH$_3$•THF complex, THF, reflux; d) MeI, K$_2$CO$_3$, MeCN, 80° C.; e) 37% HCHOaq., AcOH, 90° C.; f) i) sec-BuLi, THF, -78° C., ii) SiCl$_2$Me$_2$, -78° C. to rt iii) 0.1N HClaq.; g) KMnO$_4$, acetone, -15° C.; h) i) sec-BuLi, THF, -78° C., ii) compound E8, THF, -78° C. to rt., iii) 1N HClaq.

[Synthesis of Compound E2]

4-Bromo-2-nitrophenol (compound E1, 15.0 g, 68.8 mmol, 1 Eq), methyl bromoacetate (6.7 mL, 72.2 mmol, 1.05 Eq), and potassium carbonate (11.4 g, 82.6 mmol, 1.2 Eq) were dissolved in DMF (70 mL) in an argon atmosphere, and stirred overnight at 70° C. After returning the reaction system to room temperature and distilling off the solvent under reduced pressure, ethyl acetate was added. The solution was washed by water and saturated saline, dried by anhydrous sodium sulfate, and the solvent was removed under reduced pressure. The residue obtained was purified by medium-pressure silica gel chromatography (eluent: n-hexane/ethyl acetate=95/5 to 90/10), and the target compound E2 (19.6 g, 98%) was obtained as a pale yellow solid.

$^1$H NMR (CHCl$_3$): δ 8.01 (d, J=2.5 HZ, 1H), 6.52 (dd, J=2.5 Hz, 8.9 Hz, 1H), 6.89 (d, J=8.9 Hz, 1H), 4.79 (s, 2H), 3.81 (s, 3H); $^{13}$C NMR (CDCl$_3$): δ 168.0 (C), 150.5 (C), 140.8 (C), 136.9 (CH), 128.6 (CH), 117.0 (CH), 113.6 (C), 66.6 (CH$_2$), 52.7 (CH$_3$); HRMS-ESI (m/z): [M+Na]$^+$ calcd for C$_9$H$_8$BrNNaO$_5$: 311.94781; found: 311.94834 (−0.5 mDa, −1.7 ppm).

[Synthesis of Compound E3]

Compound E2 (13.1 g, 68.8 mmol, 1 Eq) was dissolved in acetic acid (50 mL), and placed on an ice bath. Iron powder (15.0 g, 271 mmol, 6 Eq) was added divided over five times over 20 minutes. The reaction system was stirred for another 20 minutes at room temperature, then fresh acetic acid (50 mL) was added, and it was stirred for three hours while heating and refluxing. After the reaction had been completed, the reaction system was returned to room temperature, and the iron powder was filtered out under reduced pressure, and the filtrate was distilled off under reduced pressure. A small amount of methanol was added to the residue obtained, and the solid obtained was filtered under reduced pressure. The filtered material was washed with water and methanol, and the target compound E3 (9.02 g, 88%) was obtained as light brown acicular crystals.

$^1$H NMR (DMSO-d$_6$): δ 10.8 (s, 1H), 7.07 (dd, J=2.4 Hz, 8.5 Hz, 1H), 7.02 (d, J=2.4 Hz, 1H), 6.91 (d, J=8.5 Hz, 1H), 4.59 (s, 2H); $^{13}$C NMR (DMSO-d$_6$): δ 164.7 (C), 142.6 (C), 129.1 (C), 125.3 (CH), 118.1 (CH), 118.0 (CH), 113.3 (C), 66.6 (CH$_2$).

[Synthesis of Compound E4]

Compound E3 (1.0 g, 4.4 mmol, 1 Eq) was dissolved in THF (20 mL) in an argon atmosphere, and placed on an ice bath. A THF solution of 1 M borane-THF complex (7.0 mL, 7.0 mmol, 1.6 Eq) was added and the combination was stirred overnight while heating and refluxing. The reaction system was returned to room temperature, methanol was added in small amounts, and the solvent was removed under reduced pressure. The reaction system was then diluted by ethyl acetate, and the organic layer was washed by saturated sodium hydrogen carbonate aqueous solution and saturated saline, dried by anhydrous sodium sulfate, and the solvent was removed under reduced pressure. The residue obtained was purified by medium-pressure silica gel chromatography (eluent: dichloromethane/methanol=98/2), and the target compound E4 (817 mg, 87%) was obtained as a colorless liquid.

$^1$H NMR (CDCl$_3$): δ 6.71 (dd, J=2.3 Hz, 8.4 Hz, 1H), 6.68 (d, J=2.3 Hz, 1H), 6.62 (d, J=8.4 Hz, 1H), 4.20 (t, J=4.4 Hz, 2H), 3.80 (br s, 1H), 3.38 (t, J=4.4 Hz, 2H); $^{13}$C NMR (CDCl$_3$): δ 143.1 (C), 135.2 (C), 121.2 (CH), 118.1 (CH), 117.7 (CH), 113.2 (C), 65.1 (CH$_2$), 40.6 (CH$_2$); HRMS-ESI (m/z): [M+H]$^+$ calcd for C$_8$H$_9$BrNO: 213.98620; found: 213.98626 (−0.1 mDa, −0.3 ppm).

[Synthesis of Compound E5]

Compound E4 (1.90 g, 8.88 mmol, 1 Eq) was dissolved in acetonitrile (20 mL) in an argon atmosphere, and potassium carbonate (1.98 g, 14.3 mmol, 1.6 Eq) and methyl iodide (3.0 mL, 47.5 mmol, 5 Eq) were added and the combination was stirred overnight at 50° C. After returning the reaction system to room temperature and distilling off the solvent under reduced pressure, the reaction system was diluted by ethyl acetate, the insoluble matter was distilled off by filtration under reduced pressure, and the filtrate was removed under reduced pressure. The residue obtained was purified by medium-pressure silica gel chromatography (eluent: n-hexane/ethyl acetate=98/2 to 90/10), and the target compound E5 (1.77 g, 87%) was obtained as a pale yellow solid.

$^1$H NMR (CDCl$_3$): δ 6.73-6.70 (m, 2H), 6.61 (d, J=8.0 Hz, 1H), 4.25 (t, J=4.4 Hz, 2H), 3.26 (t, J=4.4 Hz, 2H), 2.86 (s, 3H); $^{13}$C NMR (CDCl$_3$): δ 143.3 (C), 137.9 (C), 120.5 (CH), 117.2 (CH), 114.9 (CH), 113.8 (C), 64.8 (CH$_2$), 48.8 (CH$_2$), 38.7 (CH$_3$); HRMS-ESI (m/z): [M+H]$^+$ calcd for C$_9$H$_{11}$BrNO: 228.00185; found: 228.00185; found: 228.00168 (0.2 mDa, 0.8 ppm).

[Synthesis of Compound E6]

Compound E5 (360 mg, 1.58 mmol, 2 Eq) was dissolved in acetic acid (1 mL), and 37% formaldehyde aqueous solution (320 µL, 3.96 mmol, 5 Eq) was added and heated and the combination was stirred for 40 minutes at 90° C. The reaction system was returned to room temperature, and the reaction solution was neutralized by adding saturated sodium hydrogen carbonate aqueous solution in small increments. It was then extracted twice by adding ethyl acetate. The organic layer obtained was washed by water and saturated saline, dried by anhydrous sodium sulfate, and the solvent was removed under reduced pressure. The residue obtained was purified by medium-pressure silica gel chromatography (eluent: n-hexane/ethyl acetate=85/15 to 70/30), and the target compound E6 (280 mg, 76%) was obtained as a white solid.

$^1$H NMR (CDCl$_3$): δ 6.81 (s, 2H), 6.43 (s, 2H), 4.23 (t, J=4.4 Hz, 4H), 3.88 (s, 2H), 3.21 (t, J=4.4 Hz, 4H), 2.84 (s, 6H); $^{13}$C NMR (CDCl$_3$): δ 143.7 (C), 136.2 (C), 128.7 (C), 117.7 (CH), 115.9 (CH), 115.7 (C), 65.0 (CH$_2$), 48.9 (CH$_2$), 40.3 (CH$_2$), 38.8 (CH$_3$).

[Synthesis of Compound E7]

Compound E6 (253 mg, 540 mmol, 1 Eq) was dissolved in THF (20 mL) in an argon atmosphere, and the solution was stirred for 10 minutes at –78° C. 1 M sec-butyllithium cyclohexane/n-hexane solution (1.2 mL, 1.32 mmol, 2.4 Eq) was added slowly and stirred for 30 minutes. Next, dichlorodimethylsilane (80 µL, 0.651 mmol, 1.2 Eq) was added diluted by THF (5 mL). The reaction system was gradually returned to room temperature and stirred for two hours. It was acidified by adding 1N hydrochloric acid, then saturated sodium hydrogen carbonate aqueous solution was added, and the THF was distilled off under reduced pressure. The water layer obtained was extracted by ethyl acetate, then the organic layer was washed by water and saturated saline, dried by anhydrous sodium sulfate, and the solvent was removed under reduced pressure. The residue obtained was purified by medium-pressure silica gel chromatography (eluent: n-hexane/ethyl acetate=95/5 to 80/20), and the target compound E7 (123 mg, 62%) was obtained as a pale yellow solid.

$^1$H NMR (CDCl$_3$): δ 6.85 (s, 2H), 6.72 (s, 2H), 4.29 (t, J=4.4 Hz, 4H), 3.86 (s, 2H), 3.21 (t, J=4.4 Hz, 4H), 2.89 (s, 6H), 0.41 (s, 6H); $^{13}$C NMR (CDCl$_3$): δ 145.3 (C), 137.3 (C), 1354.7 (C), 127.3 (C), 117.3 (CH), 115.8 (CH), 65.2 (CH$_2$), 49.7 (CH$_2$), 39.39 (CH$_2$), 39.2 (CH$_3$), –2.0 (CH$_3$); HRMS-ESI (m/z): [M+H]$^+$ calcd for C$_{21}$H$_{27}$N$_2$O$_2$Si: 367.18363; found: 367.18354 (0.1 mDa, 0.3 ppm).

[Synthesis of Compound E8]

Compound E7 (75.0 mg, 0.205 mmol, 1 Eq) was dissolved in acetone (2 mL), and stirred for 10 minutes at –15° C. Potassium permanganate (70.0 mg, 0.443 mmol, 2.0 Eq) was added divided over two times over 10 minutes, and completion of the reaction was confirmed by TLC. The reaction system was filtered by Celite, washed by dichloromethane, and the filtrate was distilled off under reduced pressure. The residue obtained was purified by medium-pressure silica gel chromatography (eluent: dichloromethane/ethyl acetate=95/5), and the target compound E8 (49.5 mg, 64%) was obtained as a yellow solid.

$^1$H NMR (CDCl$_3$): δ 7.88 (s, 2H), 6.72 (s, 2H), 4.27 (t, J=4.5 Hz, 4H), 3.39 (t, J=4.5 Hz, 4H), 3.03 (s, 6H), 0.42 (s, 6H); $^{13}$C NMR (CDCl$_3$): δ 184.8 (C), 145.2 (C), 139.5 (C), 133.0 (C), 131.9 (C), 117.0 (CH), 114.4 (CH), 64.3 (CH$_2$), 49.0 (CH$_2$), 38.4 (CH$_3$), –0.7 (CH$_3$); HRMS-ESI (m/z): [M+H]$^+$ calcd for C$_{21}$H$_{25}$N$_2$O$_3$Si: 380.16290; found: 381.16209 (0.8 mDa, 2.1 ppm).

[Synthesis of Compound 6]

2-Bromoanisole (compound E9, 40 µL, 0.318 mmol, 11 Eq) was dissolved in THF (5 mL), and stirred for 10 minutes at –78° C. in an argon atmosphere. 1 M sec-butyllithium cyclohexane/n-hexane solution (250 µL, 0.250 mmol, 8.6 Eq) was added slowly and stirred for 10 minutes. Compound E8 (11.0 mg, 0.029 mmol, 1 Eq) was added upon being dissolved in THF (5 mL), and the reaction system was stirred for two hours while gradually returning to room temperature. The reaction system was acidified by adding 1N hydrochloric acid, then saturated sodium hydrogen carbonate aqueous solution was added. The reaction system was extracted three times by dichloromethane, and the organic phase obtained was washed by saturated saline, dried by anhydrous sodium sulfate, and the solvent was removed under reduced pressure. The residue obtained was purified by HPLC (A/B=90/10 to 10/90, 25 min), and the target compound 6 (13.4 mg, 79%) was obtained as a bluish-green solid.

$^1$H NMR (CD$_3$CN): δ 7.55 (ddd, J=8.4 Hz, 7.4 Hz, 1H), 7.22 (s, 2H), 7.17 (d, J=8.4 Hz, 1H), 7.13 (dt, J=7.4 Hz, 0.9 Hz, 1H), 7.08 (dd, J=7.4 Hz, 1.8 Hz, 1H), 6.44 (s, 2H), 4.13 (m, 4H), 3.67 (s, 3H), 3.64 (t, J=4.6 Hz, 4H), 3.30 (s, 6H), 0.55 (s, 3H), 0.53 (s, 3H); $^{13}$C NMR (CD$_3$CN): δ 167.9 (C), 157.3 (C), 145.5 (C), 144.64 (C), 144.56 (C), 131.6 (CH), 130.9 (CH), 130.4 (C), 128.9 (C), 123.6 (CH), 121.3 (CH), 121.0 (CH), 112.4 (CH), 64.0 (CH$_2$), 56.4 (CH$_3$), 50.4 (CH$_2$), 39.6 (CH$_3$), –1.0 (CH$_3$), –1.2 (CH$_3$); HRMS-ESI (m/z): [M]$^+$ calcd for C$_{28}$H$_{31}$N$_2$O$_3$Si: 471.20985; found: 471.20985; found: 471.20890 (0.9 mDa, 2.0 ppm).

Synthesis of Compound 7 (2OH OxaSiR diMe)

Compound 7 (2OH OxaSiR diMe), which is a fluorescent probe of the present invention, was synthesized according to scheme 7 below.

Scheme 7

[Chemical formula 21]

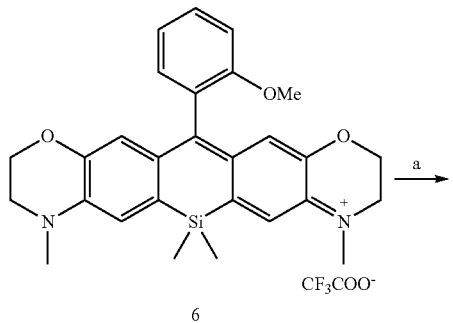

6

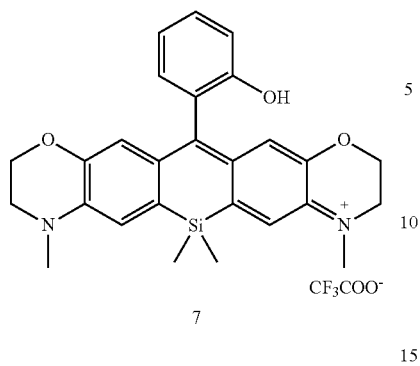

a) BBr₃, CH₂Cl₂, −78° C. to rt.

Compound 6 (4.0 mg, 6.85 μmol, 1 Eq) was dissolved⁺ in dichloromethane (2 mL), and stirred at −78° C. in an argon atmosphere. Boron trifluoride (2 drops) was added slowly and stirred at −78° C. The reaction system was gradually returned to room temperature and stirred overnight. Saturated sodium hydrogen carbonate aqueous solution was added, and the reaction system was extracted twice by dichloromethane. The organic phase obtained was washed by saturated saline, dried by anhydrous sodium sulfate, and the solvent was removed under reduced pressure. The residue obtained was purified by HPLC (A/B=90/10 to 10/90, 25 min), and compound 7 (3.2 mg, 82%) was obtained as a bluish-green solid.

$^1$H NMR (CD₃CN): δ 7.40 (m, 1H), 7.21 (s, 2H), 7.07-7.02 (m, 3H), 6.51 (s, 2H), 4.14 (m, 4H), 3.64 (t, J=4.6 Hz, 4H), 3.30 (s, 6H), 0.55 (s, 3H), 0.52 (s, 3H); $^{13}$C NMR (CH₃OD): δ 169.9 (C), 155.5 (C), 145.8 (C), 145.5 (C), 145.1 (C), 131.5 (CH), 131.32 (CH), 131.20 (C), 127.8 (C). 124.9 (CH), 120.7 (CH), 120.3 (CH), 116.7 (CH), 64.3 (CH₂). 50.7 (CH₂), 39.0 (CH₃). −1.0 (CH₃), −1.4 (CH₃); HRMS-ESI (m/z): [M]⁺ calcd for C₂₇H₂₉N₂O₃Si: 457.19420; found: 457.19403 (0.2 mDa, 0.4 ppm).

Synthesis of Compound 8 (2Me SiR600-TMR)

Compound 8 (2Me SiR600-TMR), which is a fluorescent probe of the present invention, was synthesized according to scheme 8 below. Furthermore, the synthesis of compounds F1 and F5 is disclosed in Alfons Smeets et al., Macromolecules, 2011, 44, 6017-6025 and Karine Caron et al., Org. Biomol. Chem., 2011, 9, 185-197, respectively, and synthesis was conducted based on these publications.

Scheme 8

[Chemical formula 22]

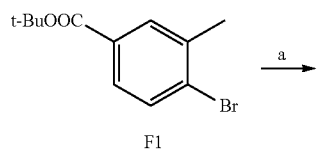

F1

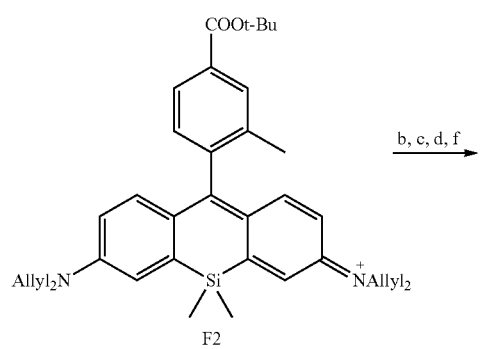

F2

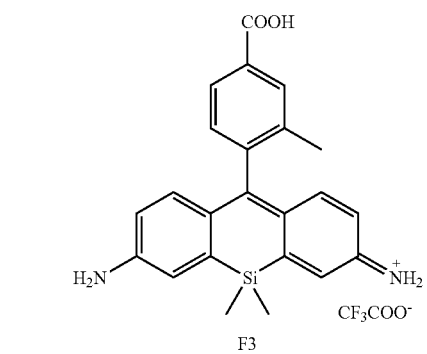

F3

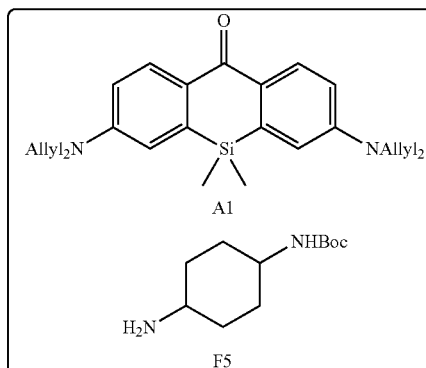

A1

F5

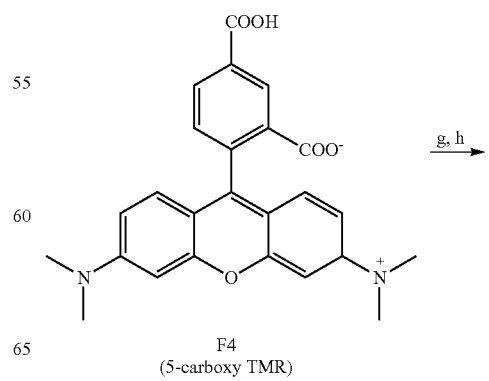

F4
(5-carboxy TMR)

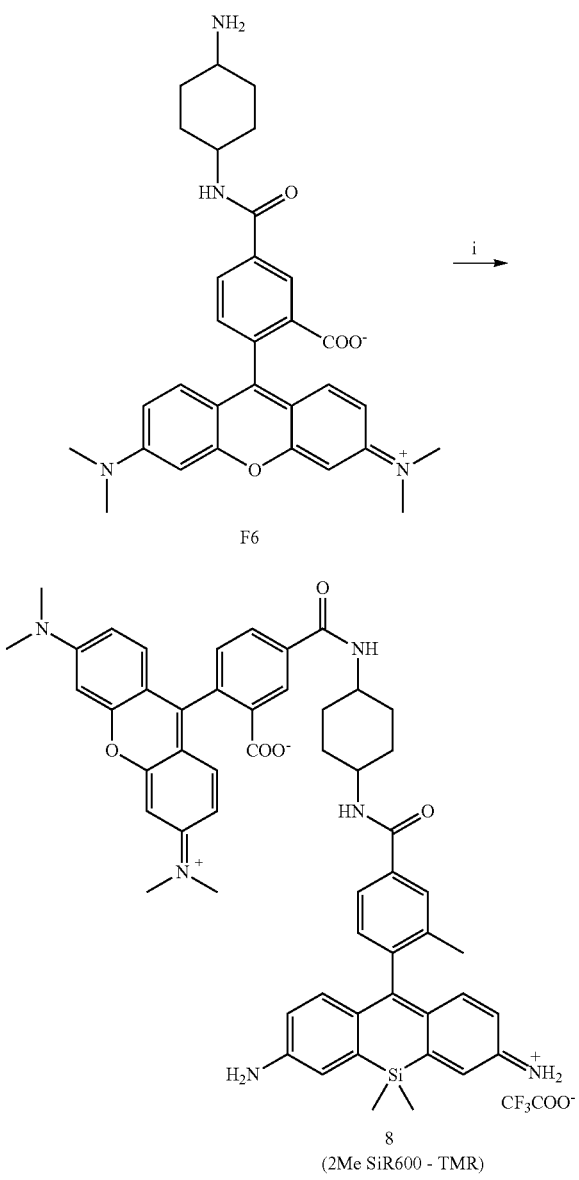

(2Me SiR600 - TMR)

a) i) sec-BuLi, THF, -78° C., ii) compound A1, THF, -78° C. to rt., iii) 1N HClaq.;
b) NaBH₄, MeOH, 0° C.,
c) 1,3-dimethylbarbituric acid, Pd(PPh₃)₄, CH₂Cl₂, 35° C.;
d) chloranil, CH₂Cl₂, rt.;
e) TFA, CH₂Cl₂, rt.;
f) compound F5, TSTU, DIEA, DMF, rt.;
g) TFA, CH₂Cl₂, rt.;
i) compound F3, TSTU, DIEA, DMSO, rt.

[Synthesis of Compound F3]

4-Bromo-3-methyl tert-butylbenzoic acid (compound F1, 54.2 mg, 0.2 mmol, 10 Eq) was dissolved in THF (5 mL), and stirred for 10 minutes at −78° C. in an argon atmosphere. 1 M sec-butyllithium cyclohexane/n-hexane solution (0.2 mL, 0.2 mmol, 10 Eq) was added slowly and stirred for 10 minutes. Compound A1 (8.6 mg, 0.02 mmol, 1 Eq) was added upon being dissolved in THF (3 mL), and stirred for one hour at −78° C. and for two hours at room temperature. The reaction system was acidified by adding 1N hydrochloric acid. Saturated sodium hydrogen carbonate aqueous solution was then added, and the reaction system was extracted twice by dichloromethane. The organic phase obtained was washed by saturated saline, dried by anhydrous sodium sulfate, and the solvent was removed under reduced pressure. The residue obtained was purified by HPLC (A/B=90/10 to 10/90, 25 min), and compound F2 (5.1 mg, 42.4%) was obtained as a blue solid. Next, compound F2 (29.3 mg, 0.049 mmol, 1 Eq) was dissolved in methanol (10 mL) and placed on an ice bath. Sodium borohydride was then added gradually, and the reaction was completed by adding water when the dark blue solution turned colorless. The solution was extracted by adding dichloromethane, and the organic phase was washed by water and saturated saline and dried by anhydrous sodium sulfate. The solvent was removed under reduced pressure, and the residue was vacuum dried. The residue obtained was dissolved in deoxygenated dichloromethane (7 mL) in an argon atmosphere, added to a test tube containing 1,3-dimethylbarbituric acid (187.4 mg, 1.20 mmol, 24 Eq) and tetrakis(triphenylphosphine)palladium (40.1 mg, 0.034 mmol, 0.7 Eq), and stirred for 60 minutes at 35° C. in an argon atmosphere. Chloranil (14.3 mg, 0.058 mmol, 1.2 Eq) was added and stirred for 60 minutes at room temperature. The dark blue reaction solution was separated by silica gel column chromatography (eluent: dichloromethane/methanol=100/0 to 80/20). The blue fraction was recovered, and the solvent was distilled off under reduced pressure. The residue was dissolved in dichloromethane (5 mL), and trifluoroacetic acid (5 mL) was added and stirred for two hours at room temperature. After distilling off the solvent under reduced pressure, the residue was purified by HPLC (A/B=90/10 to 10/90, 25 min), and the target compound F3 (8.5 mg, 45%) was obtained as a bluish-green solid.

$^1$H NMR (MeOD): δ 8.06-8.02 (m, 2H), 7.26 (d, J=7.8 Hz, 1H), 7.20 (d, J=2.4 Hz, 2H), 6.97 (d, J=9.3 Hz, 2H), 6.58 (dd, J=2.4 Hz, 9.3 Hz, 2H), 2.12 (s, 3H), 0.56 (s, 3H), 0.54 (s, 3H); $^{13}$C NMR (MeOD) δ 170.2, 169.2, 158.6, 150.4, 144.8, 143.5, 137.6, 132.6, 132.5, 130.5, 128.1, 127.9, 124.6, 117.1, 19.4, −1.5, −1.7 ppm. HRMS-ESI (m/z): [M+H]⁺ calcd for $C_{23}H_{23}N_2O_2Si$: 387.15233; found: 387.15225 (0.1 mDa, 0.2 ppm).

[Synthesis of Compound F6]

5-Carboxyl TMR (compound F4, 5.0 mg, 0.012 mmol, 1 Eq) was dissolved in DMF (2 mL), and N,N-diisopropylethylamine (4.5 mg, 0.036 mmol, 3 Eq) and N,N,N',N'-tetramethyl-0-(N-succinimidyl)uronium tetrafluoroborate (TSTU) (5.25 mg, 0.018 mmol, 1.5 Eq) were added. After stirring, trans-N-Boc-1,4-cyclohexanediamine (compound F5, 3.8 mg, 0.018 mmol, 1.5 Eq) was added and the combination was stirred for one hour at room temperature in an argon atmosphere. After distilling off the solvent under reduce pressure and vacuum drying, the residue was dissolved in dichloromethane (5 mL), and trifluoroacetic acid (5 mL) was added and the combination was stirred for two hours at room temperature. The solvent was removed under reduced pressure, and the residue obtained was purified by HPLC (A/B=90/10 to 10/90, 40 min), and compound F6 (4.5 mg, 71.0%) was obtained as a dark red solid.

$^1$H NMR (MeOD): δ 8.76 (d, J=1.8 Hz, 1H), 8.26 (dd, J=1.8 Hz, 8.0 Hz, 1H), 7.53 (d, J=8.0 Hz, 1H), 7.13 (d, J=9.5 Hz, 2H), 7.06 (dd, J=2.4 Hz, 9.5 Hz, 2H), 7.00 (d, J=2.4 Hz, 2H), 3.99-3.98 (m, 1H), 3.31 (s, 12H), 3.18-3.13 (m, 1H), 2.18-2.16 (m, 4H), 1.65-1.55 (m, 4H). HRMS-ESI (m/z): [M+H]⁺ calcd for $C_{31}H_{35}N_4O_4$: 527.26528; found: 527.26265 (2.6 mDa, 5.0 ppm).

[Synthesis of Compound 8 (2Me SiR600-TMR)]

Compound F6 (0.45 mg, 0.0011 mmol, 1.5 Eq) was dissolved in DMSO (0.3 mL), and N,N-diisopropylethylamine (0.12 mg, 0.0009 mmol, 1.2 Eq) and N,N,N',N'-tetramethyl-O-(N-succinimidyl)uronium tetrafluoroborate (TSTU) (0.3 mg, 0.0009 mmol, 1.2 Eq) were added. After stirring, compound F3 (0.4 mg, 0.00076 mmol, 1 Eq) was added and stirred for 24 hours at room temperature in an argon atmosphere. The reaction solution was purified by HPLC (A/B=90/10 to 10/90, 40 min), and compound 8 (0.24 mg, 35.2%) was obtained as a violet solid.

HRMS-ESI (m/z): [M+H]$^+$ calcd for $C_{54}H_{55}N_6O_5Si$: 895.39977; found: 895.39688 (2.9 mDa, 3.2 ppm).

Synthesis of Compound 9 (2Me SiR600-TMR(Me))

Compound 9 (2Me SiR600-TMR(Me)), which is a fluorescent probe of the present invention, was synthesized according to scheme 9 below.

Scheme 9

[Chemical formula 23]

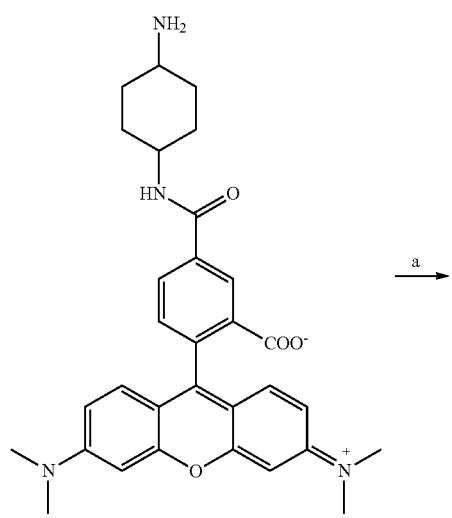

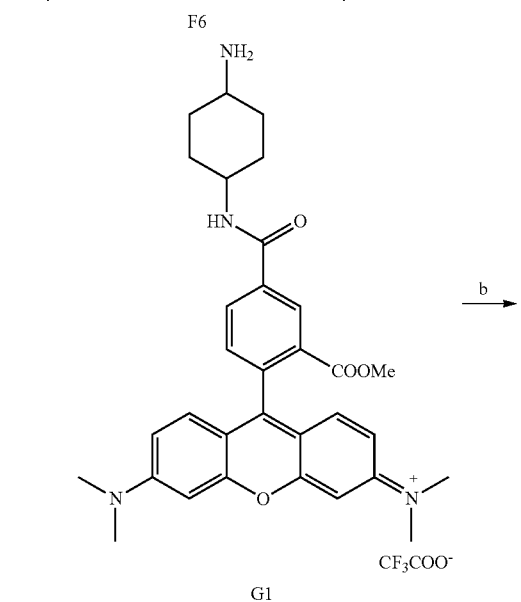

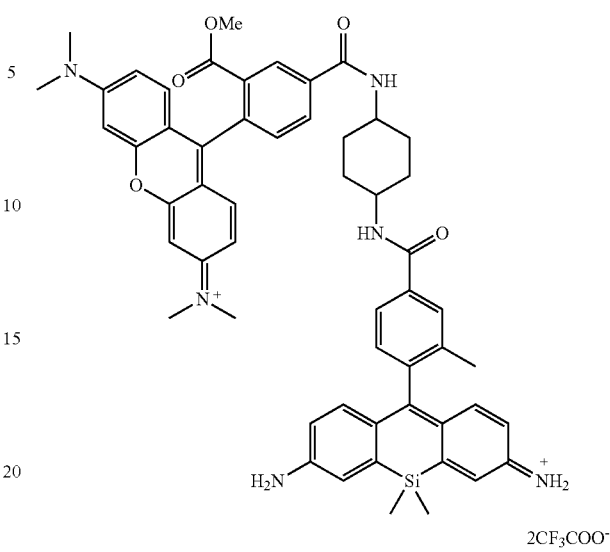

a) $H_2SO_4$, MeOH, reflux;
b) compound F3, TSTU, DIEA, DMSO, rt.

[Synthesis of Compound G1]

Compound F6 (3.0 mg, 0.006 mmol, 1 Eq) was dissolved in methanol (5 mL), one drop of concentrated sulfuric acid was added, and the solution was stirred overnight while heating and refluxing. The reaction system was returned to room temperature, and the solvent was distilled off under reduced pressure. The residue obtained was purified by HPLC (A/B=90/10 to 10/90, 40 min), and compound G1 (2.8 mg, 86.2%) was obtained as a dark red solid.

HRMS-ESI (m/z): [M+H]$^+$ calcd for $C_{32}H_{37}N_4O_4$: 541.28093; found: 541.28234 (−1.4 mDa, −2.6 ppm).

[Synthesis of Compound 9]

Compound G1 (0.23 mg, 0.0006 mmol, 1.1 Eq) was dissolved in DMSO (0.3 mL), and N,N-diisopropylethylamine (0.107 mg, 0.00082 mmol, 1.5 Eq) and N,N,N',N'-tetramethyl-0-(N-succinimidyl)uronium tetrafluoroborate (TSTU) (0.25 mg, 0.00082 mmol, 1.5 Eq) were added. After stirring, compound 6 (0.3 mg, 0.00055 mmol, 1 Eq) was added upon being dissolved in DMSO (0.2 mL), and stirred for 24 hours at room temperature in an argon atmosphere. The reaction solution was purified by HPLC (A/B=90/10 to 10/90, 40 min), and compound 9 (0.3 mg, 55.3%) was obtained as a violet solid.

HRMS-ESI (m/z): [M+2H]$^{2+}$ calcd for $C_{55}H_{58}N_6O_5Si$: 455.21135; found: 455.21238 (−1.0 mDa, −2.3 ppm).

Synthesis of Compound 10 (2Me SiR600-F1 (diAc))

Compound 10 (2Me SiR600-F1 (diAc)), which is a fluorescent probe of the present invention, was synthesized according to scheme 10 below.

Scheme 10

[Chemical formula 24]

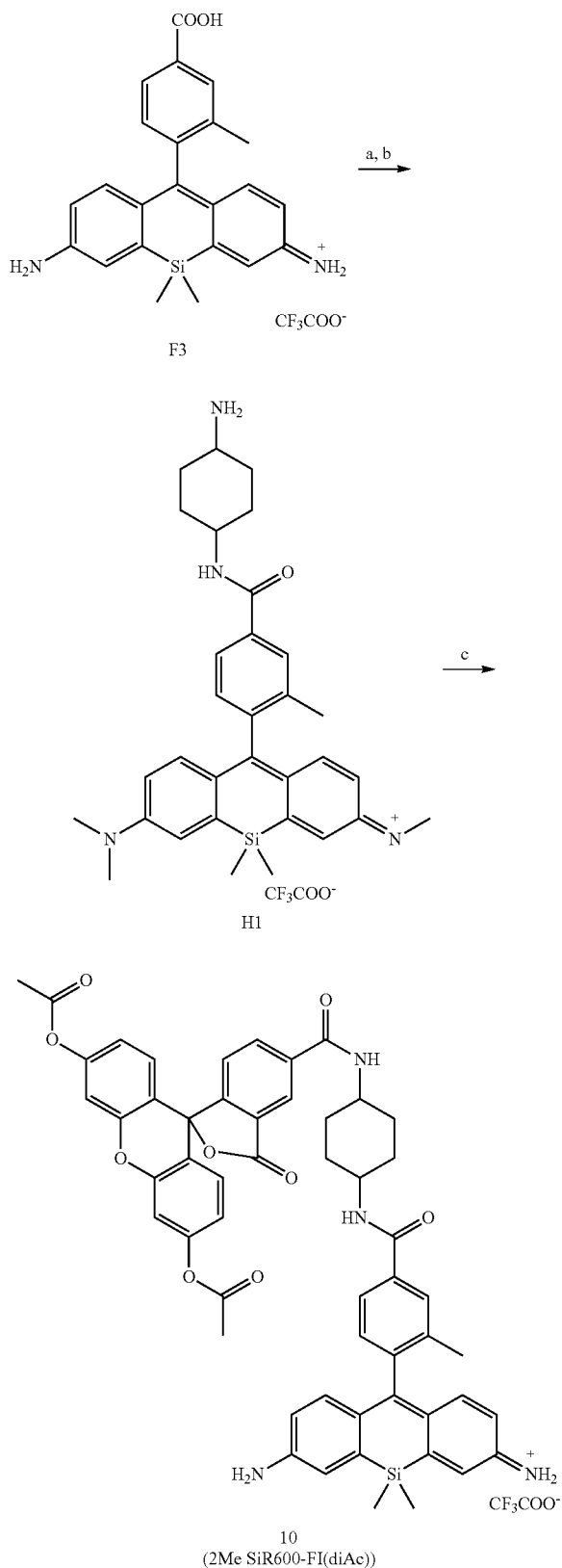

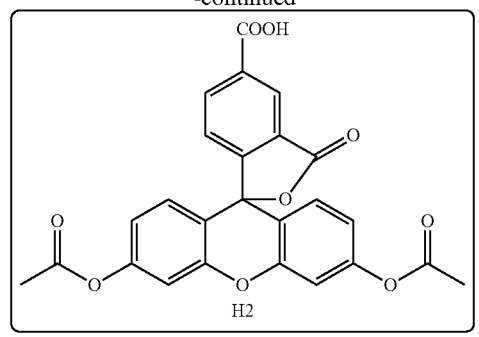

a) compound F5, TSTU, DIEA, DMF, rt.; b) TFA, CH$_2$Cl$_2$, rt.; i) compound H2, TSTU, DIEA, DMSO, rt.

[Synthesis of Compound H1]

Compound F3 (3.1 mg, 0.008 mmol, 1 Eq) was dissolved in DMF (2 mL), and N,N-diisopropylethylamine (1.55 mg, 0.024 mmol, 3 Eq) and N,N,N',N'-tetramethyl-0-(N-succinimidyl)uronium tetrafluoroborate (TSTU) (3.6 mg, 0.012 mmol, 1.5 Eq) were added. After stirring, trans-N-Boc-1,4-cyclohexanediamine (2.6 mg, 0.012 mmol, 1.5 Eq) was added and stirred for one hour at room temperature in an argon atmosphere. After distilling off the solvent under reduced pressure and vacuum drying, the residue was dissolved in dichloromethane (2 mL). Trifluoroacetic acid (2 mL) was added, and stirred for two hours at room temperature. After neutralizing the solution by adding saturated sodium bicarbonate, it was removed under reduced pressure, and the reaction system was vacuum dried. The residue obtained was dissolved in methanol, and the filtrate was removed under reduced pressure after filtering the salt. This was purified by HPLC (A/B=90/10 to 10/90, 40 min), and compound H1 (2.9 mg, 74%) was obtained as a bluish-violet solid.

$^1$H NMR (MeOD): δ 8.48 (d, J=7.8 Hz, 1H), 7.85-7.80 (m, 2H), 7.24 (d, J=7.9 Hz, 1H), 7.20 (d, J=2.4 Hz, 2H), 6.97 (D, J=9.3 Hz, 2H), 6.57 (dd, J=2.4 Hz, 9.3 Hz, 2H), 2.16-2.14 (m, 4H), 2.11 (s, 3H), 1.60-1.55 (m, 4H), 0.55 (s, 3H), 0.54 (s, 3H).

HRMS-ESI (m/z): [M+H]$^+$ calcd for C$_{29}$H$_{35}$N$_4$OSi: 483.25746; found: 483.25559 (1.9 mDa, 3.9 ppm).

[Synthesis of Compound 10 (2Me SiR600-F1 (diAc))]

Compound H1 (0.45 mg, 0.0009 mmol, 1 Eq) was dissolved in DMSO (0.3 mL), and N,N-diisopropylethylamine (0.22 mg, 0.0016 mmol, 1.8 Eq) and N,N,N',N'-tetramethyl-0-(N-succinimidyl)uronium tetrafluoroborate (TSTU) (0.56 mg, 0.0018 mmol, 2 Eq) were added. After stirring, 5-carboxy-fluorescein diacetate (compound H2, 0.64 mg, 0.0014 mmol, 1.5 Eq) was added and stirred for 24 hours at room temperature in an argon atmosphere. The reaction solution was purified by HPLC (A/B=90/10 to 10/90, 40 min), and compound 10 (0.1 mg, 12%) was obtained as a violet solid.

MS-ESI (m/z): [M+H]$^+$ calcd for C$_{54}$H$_{49}$N$_4$O$_9$Si: 925.32633; found: 925.32230 (4.0 mDa, 4.4 ppm).

[Synthesis of Compound 11]

Compound 11, which is a fluorescent probe of the present invention, was synthesized according to scheme 11 below.

Scheme 11

[Chemical formula 25]

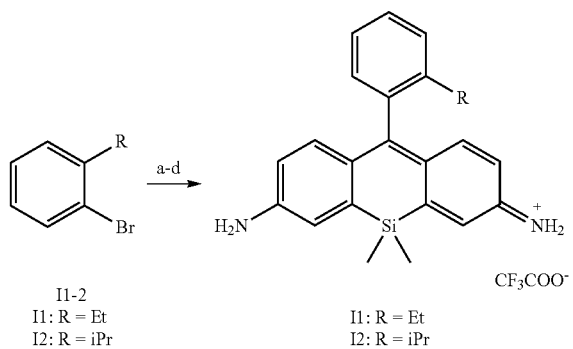

I1: R = Et
I2: R = iPr

I1-2
I1: R = Et
I2: R = iPr a) i) sec-BuLi, -78° C., THF, ii) compound A2 in THF, -78° C. to rt., iii) 1N HClaq.,
b) NaBH₄, MeOH, c) 1,3-dimethylbarbituric acid, Pd(PPh₃)₄, CH₂Cl₂, d) p-chloranil, CH₂Cl₂.

1-Bromo-2-ethylbenzene (compound I1, 100 μL, 0.728 mmol, 15.5 Eq) was dissolved in THF (5 mL), and stirred for 10 minutes at −78° C. in an argon atmosphere. 1.1 M sec-butyllithium cyclohexane/n-hexane solution (250 μL, 0.275 mmol, 5.9 Eq) was added slowly and stirred for 10 minutes. Compound A2 (20 mg, 0.047 mmol, 1 Eq) was added upon being dissolved in THF (5 mL), and stirred for one hour at −78° C. and for two hours at room temperature. The reaction system was acidified by adding 1N hydrochloric acid, then saturated sodium hydrogen carbonate aqueous solution was added, and the reaction system was extracted twice by dichloromethane. The organic phase obtained was washed by saturated saline, dried by anhydrous sodium sulfate, and the solvent was removed under reduced pressure. The compound obtained was dissolved in methanol (2 mL), and sodium borohydride was added until the color of the solution became pale yellow. The reaction was stopped by adding water, and the reaction system was extracted by ethyl acetate. The organic layer obtained was washed by saturated saline, dried by anhydrous sodium sulfate, and the solvent was removed under reduced pressure. The compound obtained was dissolved in deoxygenated dichloromethane (5 mL), and 1,3-dimethylbarbituric acid (185 mg, 1.17 mmol, 25 Eq) and tetrakis(triphenylphosphine)palladium (8.0 mg, 6 μmol, 0.1 Eq) were added and stirred for 90 minutes at 40° C. After cooling to room temperature, chloranil (15.1 mg, 0.062 mmol, 1.3 Eq) was added and stirred for 10 minutes at room temperature. The dark bluish-violet reaction solution was separated by silica gel column chromatography (eluent: dichloromethane/methanol=100/0 to 50/50). The bluish-violet fraction was recovered, and the solvent was distilled off under reduced pressure. The residue obtained was purified by HPLC (A/B=90/10 to 10/90, 25 min), and the target compound 11 (14.4 mg, 66%) was obtained as a blue solid.

$^1$H NMR (CD$_3$OD): δ 7.53-7.34 (m, 2H), 7.51 (dt, J=1.4 Hz, 7.3 Hz, 1H), 7.19 (d, J=2.5 Hz, 2H), 7.08 (dd, J=7.5 Hz, 1.0 Hz, 1H), 7.04 (d, (J=9.3 Hz, 2H), 6.56 (dd, J=9.3 Hz, 2.5 Hz, 2H), 2.37 (q, J=7.6 Hz, 2H), 1.04 (t, J=7.6 Hz, 3H), 0.55 (s, 3H), 0.53 (s, 3H); $^{13}$C NMR (CD$_3$OD): δ 172.0 (C), 158.5 (C), 150.4 (C), 144.2 (CH), 142.9 (C), 139.4 (C), 130.27 (CH), 130.16 (CH), 129.7 (CH), 128.9 (C), 126.6 (CH), 124.4 (CH), 116.7 (CH), 27.1 (CH$_2$), 15.2 (CH$_3$), −1.4 (CH$_3$), −1.9 (CH$_3$); HRMS-ESI (m/z): [M]$_+$ calcd for C$_{23}$H$_{24}$N$_2$Si: 357.17815; found: 357.17900 (−0.8 mDa, −2.4 ppm).

[Synthesis of Compound 12]

Synthesis was conducted in the same way according to scheme I1 above, and the target compound 12 (16.7 mg, 74%) was obtained as a blue solid.

$^1$H NMR (CD$_3$OD): δ 7.56-7.54 (m, 2H), 7.36-7.32 (m, 1H), 7.19 (d, J=2.5 Hz, 2H), 7.08-7.07 (m, 1H), 7.06 (d, J=9.3 Hz, 2H), 6.57 (dd, J=9.3 Hz, 2.5 Hz, 2H), 2.62 (sept, J=6.8 Hz, 1H), 1.08 (d, J=6.8 Hz, 6H), 0.548 (s, 3H), 0.540 (s, 3H); $^{13}$C NMR (CD$_3$OD): δ 172.2 (C), 158.5 (C), 150.3 (C), 147.7 (C), 144.2 (CH), 138.6 (C), 130.5 (CH), 129.9 (CH), 129.1 (C), 127.1 (CH). 126.6 (CH), 124.4 (CH), 116.5 (CH), 32.3 (CH$_3$), 24.2 (CH$_3$), −1.5 (CH$_3$), −1.7 (CH$_3$); HRMS-ESI (m/z): [M]$^+$ calcd for C$_{24}$H$_{27}$N$_2$Si: 371.19380; found: 371.19394 (−0.1 mDa, −0.4 ppm).

[Synthesis of Compounds 13-15]

Compounds 13-15, which are fluorescent probes of the present invention, were synthesized according to scheme 12 below.

Scheme 12

[Chemical formula 26]

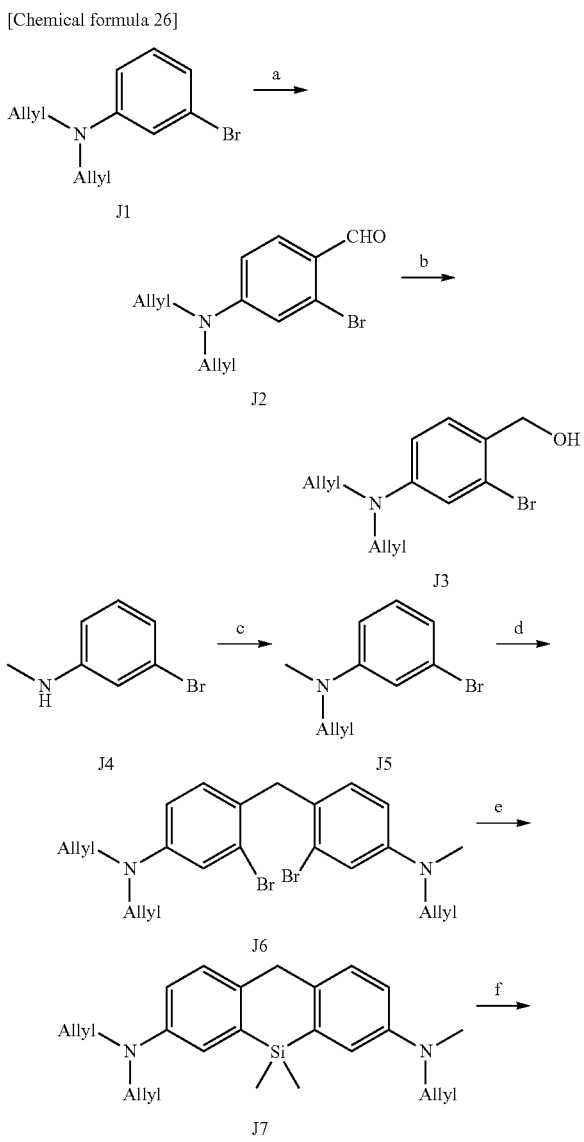

-continued

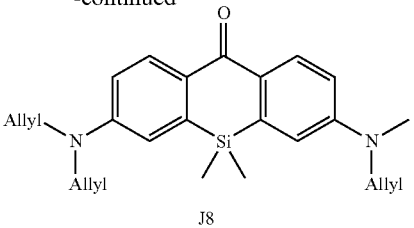

J8

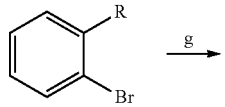

A1, C1, J11
A1: R = Me
C1: R = OMe
J11: R = OCH₂OCH₃

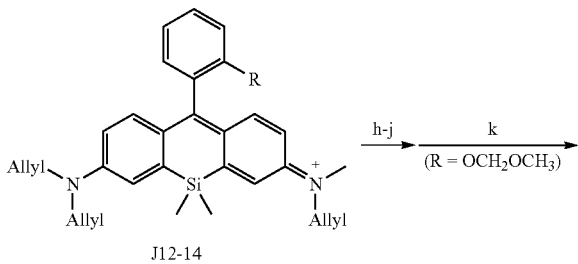

J12-14

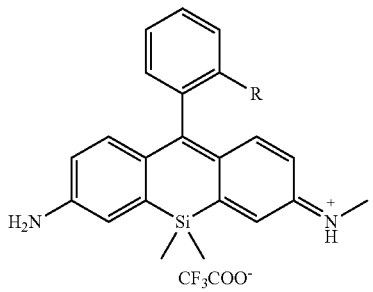

13: R = Me
14: R = OMe
15: R = OH a) i) DMF, POCl₃, (CH₂Cl)₂, reflux, ii) 1N NaOHaq., b) NaBH₄, CH₂Cl₂/MeOH, rt,
c) AllylBr, K₂CO₃, THF, reflux, d) compound J3, BF₃·OEt₂ complex, CH₂Cl₂, reflux,
e) i) sec-BuLi, THF, -78° C., ii) SiCl₂Me₂, THF, -78° C. to rt., iii) 1N HClaq. f) KMnO₄, acetone, -15° C., g) i) sec-BuLi, THF, -78° C., ii) compound J8, THF, -78° C. to rt., iii) 1N HClaq., h) NaBH₄, MeOH, i) 1,3-dimethylbarbituric acid, Pd(PPh₃)₄, CH₂Cl₂, j) p-chloranil, CH₂Cl₂, k) TFA, rt.

N,N-dimethylformamide (4.5 mL, 584. mmol, 4.4 Eq) was dissolved in 1,2-dichloroethane (10 mL), and stirred on an ice bath. Next, phosphoryl chloride (2.5 mL, 26.7 mmol, 2 Eq) was added and stirred for another 15 minutes. Compound J1 (3.35 g, 13.3 mmol, 1 Eq) was dissolved in 1,2-dichloroethane (10 mL), added to the reaction solution, and heated and refluxed for three hours. After cooling to room temperature, 1N sodium hydroxide aqueous solution was added on an ice bath. The reaction system was extracted twice by a mixed solvent of ethyl acetate/diethyl ether. The organic phase obtained was washed by saturated saline, dried by anhydrous sodium sulfate, and the solvent was removed under reduced pressure. The compound obtained was dissolved in dichloromethane/methanol mixed solvent (10 mL/10 mL), and stirred on an ice bath. Sodium borohydride (785 mg, 20.0 mmol, 1.5 Eq) was added and stirred for 30 minutes at room temperature. The reaction was stopped by adding water, and the reaction system was extracted by ethyl acetate. The organic phase obtained was washed by saturated saline, dried by anhydrous sodium sulfate, and the solvent was removed under reduced pressure. The residue obtained was separated and purified by silica gel column chromatography (eluent: hexane/ethyl acetate=90/10 to 70/30), and compound J3 (3.13 g, 84%) was obtained as a colorless, transparent liquid.

$^1$H NMR (CHCl₃): δ 7.20 (d, J=8.5 Hz, 1H), 6.86 (d, J=2.6 Hz, 1H), 6.60 (dd, J=8.5 Hz, 2.6 Hz, 1H), 5.82 (ddt, J=15.2 Hz, 10.4 Hz, 4.8 Hz, 2H), 5.19-5.13 (m, (4H), 4.62 (s, 2H), 3.90-3.89 (m, 4H), 1.86 (s, 1H); $^{13}$C NMR (CDCl₃): δ 149.5 (C), 133.2 (CH), 130.6 (CH), 127.1 (C), 124.6 (C), 116.5 (CH₂), 116.0 (CH), 111.5 (CH), 65.2 (CH₂), 52.9 (CH₂); HRMS-ESI (m/z): [M+Na]⁺ calcd for C₁₃H₁₆NBrNNaO: 304.03075; found: 304.03036 (0.4 mDa, 1.3 ppm).

[Synthesis of Compound J5]

Compound J4 (5.00 g, 26.9 mmol, 1 Eq) was dissolved in tetrahydrofuran (50 mL). Next, sodium carbonate (7.85 g, 56.9 mmol, 2.1 Eq) and allyl bromide (3.5 mL, 40.3 mmol, 1.5 Eq) were added and heated and refluxed overnight. More allyl bromide (3.5 mL, 40.3 mmol, 1.5 Eq) was added and heated and refluxed for two days. After air-cooling, the reaction solution was separated by filtration, and the filtrate was concentrated. The residue obtained was separated and purified by silica gel column chromatography (eluent: hexane/ethyl acetate=100/0 to 90/10), and compound J5 (5.53 g, 72%) was obtained as a colorless, transparent liquid.

$^1$H NMR (CDCl₃): δ 7.05 (t, J=8.1 Hz, 1H), 6.83-6.79 (m, 2H), 6.61 (dd, J=8.4 Hz, 2.2 Hz, 1H), 5.81 (ddt, J=17.0 Hz, 10.4 Hz, 4.9 Hz, 1H), 5.16 (dq, J=10.4 Hz, 1.6 Hz, 1H), 5.14 (dq, J=17.0 Hz, 1.6 Hz, 1H), 3.90 (dt, J=4.9 Hz, 1.6 Hz, 2H), 2.93 (s, 3H); $^{13}$C NMR (CDCl₃): δ 150.7 (C), 133.1 (CH), 130.4 (CH), 123.5 (C), 119.1 (CH), 116.5 (CH₂), 115.1 (CH), 111.0 (CH), 55.1 (CH₂), 38.2 (CH₂); HRMS-ESI (m/z): [M+H]⁺ calcd for C₁₀H₁₃NBrN: 226.02259; found: 226.02478 (−2.2 mDa, −9.7 ppm).

[Synthesis of Compound J6]

Compound J3 (1.00 g, 3.54 mmol, 1 Eq) and compound J5 (0.800 g, 3.54 mmol, 1 Eq) were dissolved in dichloromethane (20 mL), and stirred on an ice bath. A boron trifluoride-diethyl ether complex (650 μL, 5.46 mmol, 1.5 Eq) was added, and the reaction solution was heated and refluxed overnight. After air-cooling, saturated sodium carbonate aqueous solution was added, and the reaction system was extracted by dichloromethane. The organic phase obtained was washed by saturated saline, dried by anhydrous sodium sulfate, and the solvent was removed under reduced pressure. The residue obtained was separated and purified by silica gel column chromatography (eluent: hexane/ethyl acetate=85/15 to 70/30), and compound J6 (1.58 g, 91%) was obtained as a colorless, transparent liquid.

$^1$H NMR (CDCl₃): δ 6.92 (d, J=2.7 Hz, 1H), 6.90 (d, J=2.7 Hz, 1H), 6.84 (d, J=8.6 Hz, 1H), 6.80 (d, J=8.6 Hz, 1H), 6.56 (dd, J=8.6 Hz, 2.7 Hz, 1H), 6.54 (dd, J=8.6 Hz, 2.7 Hz, 1H), 5.87-5.76 (m, 3H), 5.19-5.12 (m, 6H), 3.70 (s, 2H), 3.88-3.87 (m, 6H), 2.90 (s, 3H); $^{13}$C NMR (CDCl₃): δ 149.1 (C), 148.3 (C), 133.7 (CH), 133.5 (CH), 130.99 (CH), 130.89 (CH), 127.10 (C), 127.07 (C), 125.78 (C), 125.68 (C), 116.52 (CH₂), 116.41 (CH₂), 116.20 (CH), 116.13 (CH), 111.87 (CH), 111.79 (CH), 55.3 (CH₂), 52.9 (CH₂), 39.9 (CH₂), 38.2 (CH₃); HRMS-ESI (m/z): [M+H]⁺ calcd for C₂₃H₂₇Br₂N₂: 489.05355; found: 489.05309 (0.5 mDa, 0.9 ppm).

[Synthesis of Compound J8]

Compound J6 (765 mg, 1.56 mmol, 1 Eq) was dissolved in THF (20 mL) in an argon atmosphere, and stirred for 10 minutes at −78° C. 1 M sec-butyllithium cyclohexane/n-hexane solution (3.5 mL, 3.5 mmol, 2.2 Eq) was added slowly and stirred for 10 minutes. Next, the reaction system was returned gradually to room temperature by adding dichlorodimethylsilane (250 μL, 2.05 mmol, 1.3 Eq) diluted by THF (5 mL), and stirred for 2.5 hours. It was acidified by adding 1N hydrochloric acid. Next, saturated sodium hydrogen carbonate aqueous solution was added, and the THF was distilled off under reduced pressure. The water layer obtained was extracted by ethyl acetate. Next, the organic phase was washed by water and saturated saline, dried by anhydrous sodium sulfate, and the solvent was removed under reduced pressure. The residue obtained was purified by medium-pressure silica gel chromatography (eluent: n-hexane/ethyl acetate=100/0 to 90/10). The compound obtained was dissolved in acetone (15 mL), and stirred for 10 minutes at −15° C. Potassium permanganate (400 mg, 2.53 mmol, 1.6 Eq) was added divided over four times over 10 minutes, and completion of the reaction was confirmed by TLC. The reaction system was filtered by Celite, washed by dichloromethane, and the filtrate was distilled off under reduced pressure. The residue obtained was purified by silica gel chromatography (eluent: hexane/dichloromethane=40/60 to 0/100), and the target compound J8 (78.1 mg, 12%) was obtained as a yellow solid.

$^1$H NMR (CDCl$_3$): δ 8.39-8.35 (m, 2H), 6.85-6.80 (m, 4H), 5.93-5.82 (m, 3H), 5.23-5.16 (m, 6H), 4.04-4.02 (m, 6H), 3.08 (s, 3H), 0.44 (s, 6H); $^{13}$C NMR (CDCl$_3$): δ 185.1 (C), 150.7 (C), 150.2 (C), 140.52 (C), 140.47 (C), 133.1 (CH), 132.8 (CH), 131.70 (CH), 131.67 (CH), 130.0 (C), 129.8 (C), 116.6 (CH$_2$), 114.8 (CH), 114.5 (CH), 113.5 (CH), 113.3 (CH), 54.7 (CH$_2$), 52.7 (CH$_2$), 38.1 (CH$_3$), −1.1 (CH$_3$); HRMS-ESI (m/z): [M+H]$^+$ calcd for C$_{25}$H$_{31}$N$_2$OSi: 403.22002; found: 403.21907 (0.9 mDa, 2.3 ppm).

[Synthesis of Compound 13]

2-Bromotoluene (compound A1, 50 μL, 0.417 mmol, 12 Eq) was dissolved in THF (5 mL), and stirred for 10 minutes at −78° C. in an argon atmosphere. 1 M sec-butyllithium cyclohexane/n-hexane solution (200 μL, 0.200 mmol, 5.7 Eq) was added slowly and stirred for 10 minutes. Compound J8 (14 mg, 0.035 mmol, 1 Eq) was added upon being dissolved in THF (5 mL), and stirred for one hour at −78° C. and for two hours at room temperature. The reaction system was acidified by adding 1N hydrochloric acid. Next, saturated sodium hydrogen carbonate aqueous solution was added, and the reaction system was extracted twice by dichloromethane. The organic phase obtained was washed by saturated saline, dried by anhydrous sodium sulfate, and the solvent was removed under reduced pressure. The compound obtained was dissolved in methanol (3 mL), and sodium borohydride was added until the color of the solution became pale yellow. The reaction was stopped by adding water, and the reaction system was extracted twice by ethyl acetate. The organic layer obtained was washed by saturated saline, dried by anhydrous sodium sulfate, and the solvent was removed under reduced pressure. The compound obtained was dissolved in deoxygenated dichloromethane (3 mL), and 1,3-dimethylbarbituric acid (108 mg, 0.697 mmol, 20 Eq) and tetrakis(triphenylphosphine)palladium (4.5 mg, 4 μmol, 0.1 Eq) were added and stirred for four hours at 40° C. Chloranil (11.0 mg, 0.045 mmol, 1.2 Eq) was added and stirred for 10 minutes at room temperature. The dark bluish-violet reaction solution was separated by silica gel column chromatography (eluent: dichloromethane/methanol=100/0 to 60/40). The bluish-violet fraction was recovered, and the solvent was distilled off under reduced pressure. The residue obtained was purified by HPLC (A/B=90/10 to 10/90, 25 min), and the target compound 13 (5.9 mg, 36%) was obtained as a bluish-violet solid.

$^1$H NMR (CD$_3$OD): δ 7.48-7.35 (m, 3H), 7.20 (d, J=2.4 Hz, 1H), 7.18 (d, J=2.5 Hz, 1H), 7.12-6.80 (m, 2H), 7.00 (d, J=9.3 Hz, 1H), 6.60 (dd, J=9.3 Hz, 2.4 Hz, 1H), 6.56 (dd, J=9.3 Hz, 2.5 Hz, 1H), 3.06 (s, 3H), 2.04 (s, 3H), 0.56 (s, 3H), 0.54 (s, 3H); $^{13}$C NMR (CD$_3$OD): δ 171.6 (C), 158.3 (C), 157.5 (C), 150.1 (C), 143.5 (CH), 140.1 (C), 136.9 (C), 131.3 (CH), 130.10 (CH), 130.04 (CH), 128.63 (C), 128.57 (C), 126.8 (CH), 124.2 (CH), 116.8 (CH), 30.0 (CH$_3$), 19.4 (CH$_3$), −1.4 (CH$_3$). −1.6 (CH$_3$); HRMS-ESI (m/z): [M]$^+$ calcd for C$_{23}$H$_{25}$N$_2$Si: 357.17815; found: 357.17925 (−1.1 mDa, −3.1 ppm).

[Synthesis of Compound 14]

2-Bromoanisole (compound C1, 50 μL, 0.408 mmol, 16 Eq) was dissolved in THF (5 mL), and stirred for 10 minutes at −78° C. in an argon atmosphere. 1.1 M sec-butyllithium cyclohexane/n-hexane solution (200 μL, 0.220 mmol, 9 Eq) was added slowly and stirred for 10 minutes. Compound J8 (10 mg, 0.025 mmol, 1 Eq) was added upon being dissolved in THF (5 mL), and stirred for one hour at −78° C. and for two hours at room temperature. The reaction system was acidified by adding 1N hydrochloric acid. Next, saturated sodium hydrogen carbonate aqueous solution was added, and the reaction system was extracted twice by dichloromethane. The organic phase obtained was washed by saturated saline, dried by anhydrous sodium sulfate, and the solvent was removed under reduced pressure. The compound obtained was dissolved in methanol (2 mL), and sodium borohydride was added until the color of the solution became pale yellow. The reaction was stopped by adding water, and the reaction system was extracted by ethyl acetate. The organic layer obtained was washed by saturated saline, dried by anhydrous sodium sulfate, and the solvent was removed under reduced pressure. The compound obtained was dissolved in deoxygenated dichloromethane (2 mL), and 1,3-dimethylbarbituric acid (78.0 mg, 0.500 mmol, 20 Eq) and tetrakis(triphenylphosphine)palladium (2.0 mg, 2 μmol, 0.1 Eq) were added and stirred overnight at room temperature. Chloranil (10.1 mg, 0.042 mmol, 1.7 Eq) was added and stirred for 10 minutes at room temperature. The dark bluish-violet reaction solution was separated by silica gel column chromatography (eluent: dichloromethane/methanol=100/0 to 60/40). The bluish-violet fraction was recovered, and the solvent was distilled off under reduced pressure. The residue obtained was purified by HPLC (A/B=90/10 to 10/90, 25 min), and the target compound 14 (4.5 mg, 37%) was obtained as a bluish-violet solid.

$^1$H NMR (CD$_3$OD): δ 7.56 (ddd, J=8.5 Hz, 7.4 Hz, 1.8 Hz, 1H), 7.20 (d, J=8.4 Hz, 1H), 7.17-7.07 (m, 6H), 6.59 (dd, J=9.3 Hz, 2.0 Hz, 1H), 6.54 (dd, J=9.3 Hz, 2.5 Hz, 1H), 3.73 (s, 3H), 3.05 (s, 3H), 0.55 (s, 3H), 0.52 (s, 3H); $^{13}$C NMR (CD$_3$OD): δ 170.1 (C), 158.16 (C), 158.06 (C), 157.4 (C), 149.9 (C), 143.8 (CH), 131.7 (CH), 131.4 (CH), 129.22 (C), 129.17 (C), 129.13 (C), 123.9 (CH), 121.4 (CH), 116.5 (CH), 112.3 (CH), 56.2 (CH$_3$), 30.0 (CH$_3$), −1.3 (CH$_3$), −1.7 (CH$_3$); HRMS-ESI (m/z): [M]$^+$ calcd for C$_{23}$H$_{25}$N$_2$OSi: 373.17307; found: 373.17276 (0.3 mDa, 0.8 ppm).

[Synthesis of Compound 15]

1-Bromo-2-(methoxymethoxy)benzene (compound J11, 86 mg, 0.398 mmol, 16 Eq) was dissolved in THF (5 mL), and stirred for 10 minutes at −78° C. in an argon atmosphere. 1.1 M sec-butyllithium cyclohexane/n-hexane solution (200 μL, 0.220 mmol, 9 Eq) was added slowly and stirred for 10 minutes. Compound J8 (10 mg, 0.025 mmol, 1 Eq) was added upon being dissolved in THF (5 mL), and stirred for one hour at −78° C. and for two hours at room temperature.

The reaction system was acidified by adding 1N hydrochloric acid. Next, saturated sodium hydrogen carbonate aqueous solution was added, and the reaction system was extracted twice by dichloromethane. The organic phase obtained was washed by saturated saline, dried by anhydrous sodium sulfate, and the solvent was removed under reduced pressure. The compound obtained was dissolved in methanol (2 mL), and sodium borohydride was added until the color of the solution became pale yellow. The reaction was stopped by adding water, and the reaction system was extracted by ethyl acetate. The organic layer obtained was washed by saturated saline, dried by anhydrous sodium sulfate, and the solvent was removed under reduced pressure. The compound obtained was dissolved in deoxygenated dichloromethane (2 mL), and 1,3-dimethylbarbituric acid (72.8 mg, 0.468 mmol, 19 Eq) and tetrakis(triphenylphosphine)palladium (3.5 mg, 2 μmol, 0.1 Eq) were added and stirred overnight at room temperature. Chloranil (11.3 mg, 0.046 mmol, 1.8 Eq) was added and stirred for 10 minutes at room temperature. The dark bluish-violet reaction solution was separated by silica gel column chromatography (eluent: dichloromethane/methanol=100/0 to 60/40). The bluish-violet fraction was recovered, and the solvent was distilled off under reduced pressure. The compound obtained was dissolved in trifluoroacetic acid (2 mL) and water (200 μL), and stirred for one hour at room temperature. After concentrating the solvent, the residue obtained was purified by HPLC (A/B=90/10 to 10/90, 25 min), and the target compound 15 (0.5 mg, 4%) was obtained as a bluish-violet solid.

$^1$H NMR (CD$_3$OD): δ 7.42-7.37 (m, 1H), 7.27 (br s, 1H), 7.18 (d, J=9.3 Hz, 1H), 7.16 (d, J=2.0 Hz, 1H), 7.15 (d, J=2.5 Hz, 1H), 7.04-7.02 (m, 2H), 6.98 (d, J=8.2 Hz, 1H), 6.61 (dd, J=9.6 Hz, 2.0 Hz, 1H), 6.56 (dd, J=9.3 Hz, 2.5 Hz, 1H), 3.06 (s, 3H), 2.04 (s, 3H), 0.56 (s, 3H), 0.52 (s, 3H); $^{13}$C NMR (CD$_3$OD): δ 170.1 (C), 158.2 (C), 157.4 (C), 155.6 (C), 144.0 (C), 131.51 (CH), 131.44 (CH), 129.35 (C), 129.30 (C), 127.5 (C), 123.9 (CH), 120.3 (CH), 116.6 (CH), 116.5 (CH), 30.0 (CH$_3$), −1.2 (CH$_3$), −1.7 (CH$_3$); HRMS-ESI (m/z): [M]$^+$ calcd for C$_{22}$H$_{23}$N$_2$OSi: 359.15742; found: 359.15767 (−0.3 mDa, −0.7 ppm).

[Synthesis of Compounds 16 and 17]

Compounds 16 and 17, which are fluorescent probes of the present invention, were synthesized according to scheme 13 below.

Scheme 13

[Chemical formula 27]

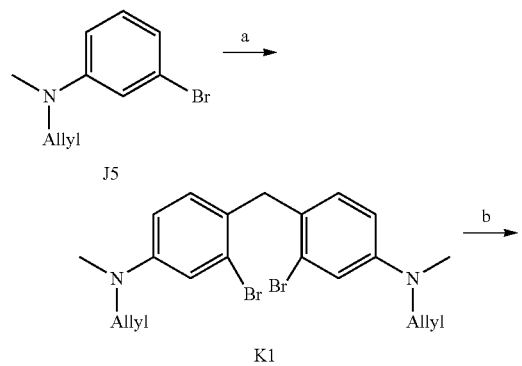

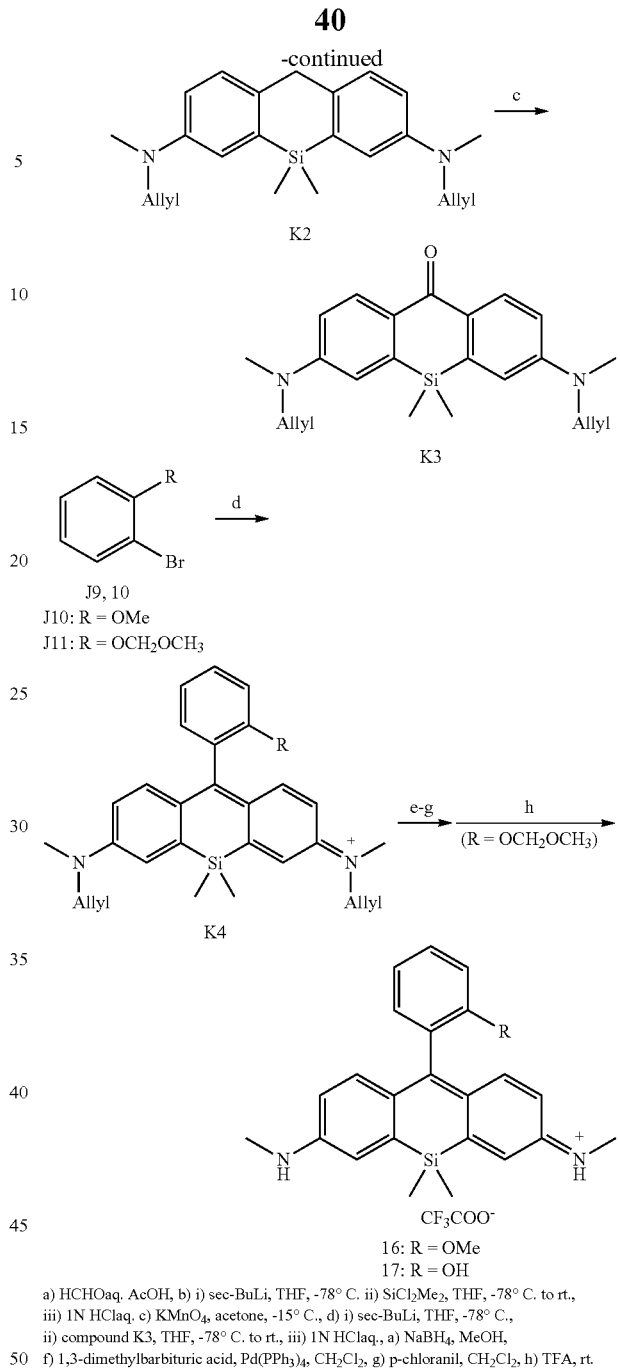

a) HCHOaq. AcOH, b) i) sec-BuLi, THF, -78° C. ii) SiCl$_2$Me$_2$, THF, -78° C. to rt., iii) 1N HClaq. c) KMnO$_4$, acetone, -15° C., d) i) sec-BuLi, THF, -78° C., ii) compound K3, THF, -78° C. to rt., iii) 1N HClaq, a) NaBH$_4$, MeOH, f) 1,3-dimethylbarbituric acid, Pd(PPh$_3$)$_4$, CH$_2$Cl$_2$, g) p-chloranil, CH$_2$Cl$_2$, h) TFA, rt.

[Synthesis of Compound K1]

Compound J5 (3.00 g, 13.3 mmol, 1 Eq) was dissolved in acetic acid (12 mL), and 37% formaldehyde aqueous solution (1.81 g, 66.3 mmol, 5 Eq) was added, and heated and the combination was stirred for one hour at 80° C. The reaction system was returned to room temperature, and the solvent was distilled off under reduced pressure. The reaction system was neutralized by adding saturated sodium hydrogen carbonate aqueous solution in small increments, then extracted three times by adding dichloromethane. The organic layer obtained was washed by water and saturated saline, dried by anhydrous sodium sulfate, and the solvent was removed under reduced pressure. The residue obtained was purified by medium-pressure silica gel chromatography (eluent: n-hexane/ethyl acetate=100/0 to 80/20), and the target compound K1 (1.85 g, 60%) was obtained as a pale yellow liquid.

$^1$H NMR (CDCl$_3$): δ 2.92 (s, 6H), 3.89 (d, 4H, J=5.0 Hz), 4.01 (s, 2H,), 5.15-5.19 (m, 4H), 5.83 (ddt, 2H, J=5.0 9.8, 17.6 Hz), 6.59 (dd, 2H, J=2.7, 8.6 Hz), 6.86 (d, 2H, J=8.6 Hz), 6.95 (d, 2H, J=2.7 Hz); $^{13}$C NMR (100 MHz, CDCl$_3$): δ 38.1, 39.9, 55.2, 111.8, 116.1, 116.5, 125.7, 127.0, 130.9, 133.4, 149.0; HRMS-ESI: Calcd for [M+H]$^+$, 463.03790, Found, 463.03830 (+0.4 mDa).

[Synthesis of Compound K3]

Compound K1 (1.01 g, 2.18 mmol, 1 Eq) was dissolved in THF (60 mL) in an argon atmosphere, and stirred for 10 minutes at −78° C. 1 M sec-butyllithium cyclohexane/n-hexane solution (6.53 mL, 6.53 mmol, 3 Eq) was added slowly and stirred for 20 minutes. Next, the reaction system was returned to room temperature gradually by adding dichlorodimethylsilane (400 μL, 4.35 mmol, 2 Eq) diluted by THF (10 mL), and stirred for two hours. The reaction system was acidified by adding 1N hydrochloric acid. Next, saturated sodium hydrogen carbonate aqueous solution was added, and the THF was distilled off under reduced pressure. The water layer obtained was extracted by ethyl acetate. Next, the organic phase was washed by water and saturated saline, dried by anhydrous sodium sulfate, and the solvent was removed under reduced pressure. The residue obtained was purified by medium-pressure silica gel chromatography (eluent: n-hexane/ethyl acetate-100/0 to 88/12). The compound obtained was dissolved in acetone (20 mL), and stirred for 10 minutes at 0° C. Potassium permanganate (1.00 g, 6.10 mmol, 2.8 Eq) was added divided over four times over 10 minutes, and completion of the reaction was confirmed by TLC. The reaction system was filtered by Celite, washed by dichloromethane, and the filtrate was distilled off under reduced pressure. The residue obtained was purified by silica gel chromatography (eluent: hexane/ethyl acetate=80/20 to 60/40), and the target compound K3 (93.9 mg, 11%) was obtained as a yellow solid.

$^1$H NMR (CDCl$_3$): δ 0.44 (m, 6H), 3.08 (s, 6H), 4.03-4.04 (m, 4H), 5.16-5.21 (m, 4H), 5.86 (ddt, 2H, J=4.9, 10.5, 16.9 Hz), 6.79 (d, 2H, J=2.8 Hz), 6.83 (dd, 2H, J=2.8, 9.0 Hz), 8.37 (d, 2H, J=9.0 Hz); $^{13}$C NMR (CDCl$_3$): δ −0.95, 38.1, 54.8, 113.4, 114.6, 116.7, 130.0, 131.8, 132.9, 140.6, 150.8, 185.3; HRMS-ESI: Calcd for [M+H]$^+$, 377.20437, Found, 377.20544 (+1.1 mDa).

[Synthesis of compound 16]

2-Bromoanisole (compound J9, 50 μL, 0.408 mmol, 16 Eq) was dissolved in THF (5 mL), and stirred for 10 minutes at −78° C. in an argon atmosphere. 1 M sec-butyllithium cyclohexane/n-hexane solution (200 μL, 0.200 mmol, 5.7 Eq) was added slowly and stirred for 10 minutes. Compound K3 (15 mg, 0.040 mmol, 1 Eq) was added upon being dissolved in THF (5 mL), and stirred for one hour at −78° C. and for two hours at room temperature. The reaction system was acidified by adding 1N hydrochloric acid. Next, saturated sodium hydrogen carbonate aqueous solution was added, and the reaction system was extracted twice by dichloromethane. The organic phase obtained was washed by saturated saline, dried by anhydrous sodium sulfate, and the solvent was removed under reduced pressure. The compound obtained was dissolved in methanol (2 mL), and sodium borohydride was added until the color of the solution became pale yellow. The reaction was stopped by adding water, and the reaction system was extracted by ethyl acetate. The organic layer obtained was washed by saturated saline, dried by anhydrous sodium sulfate, and the solvent was removed under reduced pressure. The compound obtained was dissolved in deoxygenated dichloromethane (3 mL), and 1,3-dimethylbarbituric acid (78.9 mg, 0.508 mmol, 13 Eq) and tetrakis(triphenylphosphine)palladium (6.4 mg, 5 μmol, 0.1 Eq) were added, and stirred for 1.5 hour at 40° C. Chloranil (13.1 mg, 0.053 mmol, 1.3 Eq) was added, and stirred for 10 minutes at room temperature. The dark blue reaction solution was separated by silica gel column chromatography (eluent: dichloromethane/methanol-100/0 to 60/40). The blue fraction was recovered, and the solvent was distilled off under reduced pressure. The residue obtained was purified by HPLC (A/B=90/10 to 10/90, 25 min), and the target compound 16 (12.5 mg, 63%) was obtained as a blue solid.

$^1$H NMR (CD$_3$OD): δ 7.55 (dt, J=1.5 Hz, 7.5 Hz, 1H), 7.22-7.07 (m, 5H), 7.16 (d, J=2.4 Hz, 2H), 6.58 (dd, J=9.4 Hz, 2.4 Hz, 2H), 3.72 (s, 3H), 3.05 (s, 6H), 0.56 (s, 3H), 0.53 (s, 3H); $^{13}$C NMR (CD$_3$OD): δ 169.7 (C), 158.1 (C), 157.2 (C), 143.7 (C), 131.7 (CH), 131.4 (CH), 129.26 (C), 129.16 (C), 121.4 (CH), 112.3 (CH), 56.2 (CH$_3$), 29.9 (CH$_3$), −1.2 (CH$_3$), −1.6 (CH$_3$); HRMS-ESI (m/z): [M]$^+$ calcd for C$_{24}$H$_{27}$N$_2$OSi: 387.18872; found: 387.18804 (0.7 mDa, 1.7 ppm).

[Synthesis of Compound 17]

1-Bromo-2-(methoxymethoxy)benzene (compound J10, 100 mg, 0.462 mmol, 12 Eq) was dissolved in THF (5 mL), and stirred for 10 minutes at −78° C. in an argon atmosphere. 1.1 M sec-butyllithium cyclohexane/n-hexane solution (250 μL, 0.275 mmol, 7 Eq) was added slowly and stirred for 10 minutes. Compound K3 (15 mg, 0.040 mmol, 1 Eq) was dissolved in THF (5 mL), and stirred for one hour at −78° C. and for two hours at room temperature. The reaction system was acidified by adding 1N hydrochloric acid. Next, saturated sodium hydrogen carbonate aqueous solution was added, and the reaction system was extracted twice by dichloromethane. The organic phase obtained was washed by saturated saline, dried by anhydrous sodium sulfate, and the solvent was removed under reduced pressure. The compound obtained was dissolved in methanol (2 mL), and sodium borohydride was added until the color of the solution became pale yellow. The reaction was stopped by adding water, and the reaction system was extracted by ethyl acetate. The organic layer obtained was washed by saturated saline, dried by anhydrous sodium sulfate, and the solvent was removed under reduced pressure. The compound obtained was dissolved in deoxygenated dichloromethane (3 mL), and 1,3-dimethylbarbituric acid (80.4 mg, 0.517 mmol, 13 Eq) and tetrakis(Triphenylphosphine)palladium (5.0 mg, 4 μmol, 0.1 Eq) were added and stirred for 10 minutes at room temperature. The dark blue reaction solution was separated by silica gel column chromatography (eluent: dichloromethane/methanol=100/0 to 60/40). The blue fraction was recovered, and the solvent was distilled off under reduced pressure. The compound obtained was dissolved in trifluoroacetic acid (2 mL) and water (200 μL), and stirred for one hour at room temperature. After concentrating the solvent, the residue obtained was purified by HPLC (A/B=90/10 to 10/90, 25 min), and the target compound 17 (12.7 mg, 66%) was obtained as a blue solid.

$^1$H NMR (CD$_3$OD): δ 7.40-7.37 (m, 1H), 7.25 (d, J=8.8 Hz, 2H), 7.16 (d, J=2.5 Hz, 2H), 7.02-6.98 (m, 3H), 6.59 (dd, J=9.4 Hz, 2.4 Hz, 2H), 3.04 (s, 6H), 0.56 (s, 3H), 0.53 (s, 3H); $^{13}$C NMR (CD$_3$OD): δ 170.3 (C), 157.2 (C), 155.6 (C), 131.52 (CH), 131.39 (CH), 129.4 (C), 127.5 (C), 120.2 (CH), 116.6 (CH), 29.9 (CH$_3$), −1.1 (CH$_3$), −1.6 (CH$_3$); HRMS-ESI (m/z): [M]$^+$ calcd for C$_{23}$H$_{25}$N$_2$OSi: 373.17307; found: 373.17252 (0.5 mDa, 1.5 ppm).

Synthesis of Compounds 18-22

Compounds 18-22, which are fluorescent probes of the present invention, were synthesized according to scheme 14 below.

Scheme 14

[Chemical formula 28]

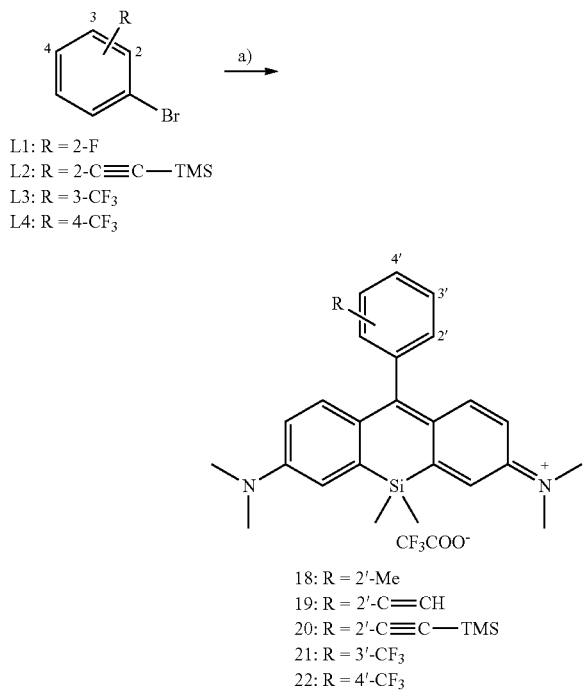

L1: R = 2-F
L2: R = 2-C≡C—TMS
L3: R = 3-CF₃
L4: R = 4-CF₃

18: R = 2'-Me
19: R = 2'-C≡CH
20: R = 2'-C≡C—TMS
21: R = 3'-CF₃
22: R = 4'-CF₃ a) i) sec-BuLi, THF, -78° C., ii) compound B1, THF, -78° C. to rt., iii) 1N HClaq.

[Synthesis of Compound 18]

1-Bromo-2-fluorobenzene (compound L1, 100 μL, 0.925 mmol, 15 Eq) was dissolved in THF (5 mL), and stirred for 10 minutes at −78° C. in an argon atmosphere. 1.9 M phenyllithium dibutyl ether solution (200 μL, 0.380 mmol, 6.1 Eq) was added slowly, and stirred for 10 minutes. Compound B1 (20 mg, 0.062 mmol, 1 Eq) was added upon being dissolved in THF (5 mL), and stirred for 10 minutes at −78° C. and for four hours at room temperature. The reaction system was acidified by adding 1N hydrochloric acid. Next, saturated sodium hydrogen carbonate aqueous solution was added, and the reaction system was extracted twice by dichloromethane. The organic phase obtained was washed by saturated saline, dried by anhydrous sodium sulfate, and the solvent was removed under reduced pressure. The residue obtained was purified by HPLC (A/B=90/10 to 10/90, 25 min), and the target compound 18 (23.8 mg, 75%) was obtained as a blue solid.

$^1$H NMR (CD$_3$OD): δ 7.66-7.60 (m, 1H), 7.40 (dt, J=7.5 Hz (t) $^4J_{H\text{-}F}$=1.0 Hz (d), 1H), 7.37 (d, J=2.8 Hz, 2H), 7.33 (ddd, J=8.3 Hz, 0.8 Hz, $^4J_{H\text{-}F}$=8.6 Hz, 1H), 7.28 (ddd, J=7.4 Hz, 1.7 Hz, $^3J_{H\text{-}F}$=9.2 Hz, 1H), 7.15 (dd, J=9.6 Hz, $^6J_{H\text{-}F}$=0.9 Hz, 2H), 6.80 (dd, J=9.6 Hz, 2.9 Hz, 2H), 3.36 (s, 12H), 0.614 (s, 3H), 0.602 (s, 3H); $^{13}$C NMR (CD$_3$OD): δ 164.0 (C), 160.7 (d, $^1J_{C\text{-}F}$=245 Hz, C), 155.8 (C), 149.4 (C), 142.2 (CH), 132.53 (d, $^4J_{C\text{-}F}$=2.5 Hz, CH), 132.48 (d, $^3J_{C\text{-}F}$=2.9 Hz, CH) 128.8 (C), 127.8 (d, $^2J_{C\text{-}F}$=17.0 Hz, C), 125.5 (d, $^3J_{C\text{-}F}$=3.6 Hz, CH), 122.4 (CH), 116.8 (d, $^2J_{C\text{-}F}$=21.7 Hz, CH), 115.3 (CH), 40.9 (CH$_3$), −1.10 (CH$_3$), −1.22 (CH$_3$); $^{19}$F{$^1$H} NMR (CD$_3$OD): δ −114.1; HRMS-ESI (m/z): [M]$^+$ calcd for C$_{25}$H$_{28}$FN$_2$Si: 403.20003; found: 403.20007 (0.0 mDa, −0.1 ppm).

[Synthesis of Compounds 19 and 20]

Compound L2 (100 μL, 0.470 mmol, 5 Eq) was dissolved in THF (5 mL), and stirred for 10 minutes at −78° C. in an argon atmosphere. 1.1 M sec-butyllithium cyclohexane/n-hexane solution (400 μL, 0.440 mmol, 4.8 Eq) was added slowly, and stirred for 10 minutes. Compound B1 (30 mg, 0.092 mmol, 1 Eq) was added upon being dissolved in THF (5 mL), and stirred for one hour at −78° C. and for one hour at room temperature. The reaction system was acidified by adding 1N hydrochloric acid. Next, saturated sodium hydrogen carbonate aqueous solution was added, and the reaction system was extracted twice by dichloromethane. The organic phase obtained was washed by saturated saline, dried by anhydrous sodium sulfate, and the solvent was removed under reduced pressure. The residue obtained was purified by HPLC (A/B=90/10 to 10/90, 25 min), and compound 19 (4.3 mg, 9%) and compound 20 (48.1 mg, 87%) were each obtained as blue solids.

Compound 19: $^1$H NMR (CD$_3$OD): δ 7.70-7.68 (m, 1H), 7.61-7.55 (m, 2H), 7.35 (d, J=2.9 Hz, 2H), 7.30-7.28 (m, 1H), 7.05 (d, J=9.6 Hz, 2H), 6.77 (dd, J=9.6 Hz, 2.9 Hz, 2H), 3.40 (s, 1H), 3.35 (s, 12H), 0.63 (s, 3H), 0.57 (s, 3H); $^{13}$C NMR (CD$_3$OD): δ 169.3 (C), 155.7 (C), 149.6 (C), 143.5 (C), 142.5 (CH), 133.9 (CH), 130.6 (CH), 129.9 (CH), 129.6 (CH), 128.9 (C), 123.6 (C), 122.1 (CH), 115.1 (CH), 83.4 (CH), 82.0 (C), 40.9 (CH$_3$), −0.8 (CH$_3$), −1.7 (CH$_3$); HRMS-ESI (m/z): [M]$^+$ calcd for C$_{27}$H$_{29}$N$_2$Si: 409.20945; found: 409.20922 (0.2 mDa, 0.6 ppm).

Compound 20: $^1$H NMR (CD$_3$OD): δ 7.63-7.61 (m, 1H), 7.57-7.54 (m, 2H), 7.37 (d, J=2.8 Hz, 2H), 7.30-7.27 (m, 1H), 7.07 (d, J=9.6 Hz, 2H), 6.78 (dd, J=9.6 Hz, 2.8 Hz, 2H), 3.35 (s, 12H), 0.620 (s, 3H), 0.604 (s, 3H), −0.12 (s, 9H); $^{13}$C NMR (CD$_3$OD): δ 169.6 (C), 155.7 (C), 149.5 (C), 143.6 (C), 142.7 (CH), 133.1 (CH), 130.6 (CH), 130.0 (CH), 129.5 (CH), 128.9 (C), 124.4 (C), 122.0 (CH), 115.0 (CH), 104.0 (C), 100.2 (C), 40.9 (CH$_3$), −0.3 (CH$_3$), −0.93 (CH$_3$), −0.99 (CH$_3$); HRMS-ESI (m/z): [M]$^+$ calcd for C$_{30}$H$_{37}$N$_2$Si$_2$: 481.24898; found: 481.24886 (0.1 mDa, 0.2 ppm).

[Synthesis of Compound 21]

1-Bromo-3-(trifluoromethyl)benzene (compound L3, 100 μL, 0.470 mmol, 5 Eq) was dissolved in THF (5 mL), and stirred for 10 minutes at −78° C. in an argon atmosphere. 1.1 M sec-butyllithium cyclohexane/n-hexane solution (500 μL, 0.550 mmol, 9 Eq) was added slowly, and stirred for 10 minutes. Compound B1 (20 mg, 0.062 mmol, 1 Eq) was added upon being dissolved in THF (5 mL), and stirred for 10 minutes at −78° C. and for one hour at room temperature. The reaction system was acidified by adding 1N hydrochloric acid. Next, saturated sodium hydrogen carbonate aqueous solution was added, and the reaction system was extracted twice by dichloromethane. The organic phase obtained was washed by saturated saline, dried by anhydrous sodium sulfate, and the solvent was removed under reduced pressure. The residue obtained was purified by HPLC (A/B=90/10 to 10/90, 25 min), and compound 21 (13.8 mg, 40%) was obtained as a blue solid.

$^1$H NMR (CD$_3$OD): δ 7.90 (d, J=7.9 Hz, 1H), 7.80 (t, J=7.8 Hz, 1H), 7.59 (s, 1H), 7.57 (d, J=7.7 Hz, 1H), 7.38 (d, J=2.8 Hz, 2H), 7.02 (d, J=9.7 Hz, 2H), 6.80 (dd, J=9.7 Hz, 2.9 Hz, 2H), 3.36 (s, 12H), 0.617 (s, 3H), 0.613 (s, 3H); $^{13}$C NMR (CD$_3$OD): δ 168.0 (C), 155.7 (C), 149.6 (C), 142.7 (CH), 141.7 (C), 134.2 (CH), 132.1 (q, $^2J_{C\text{-}F}$=36 Hz, C), 130.5 (CH), 128.7 (C), 127.0 (q, $^3J_{C-F}$=3.7 Hz, CH), 126.6 (q, $^3H_{C-F}$=4.1 Hz, CH), 122.5 (CH), 115.2 (CH), 40.9 (CH$_3$), −1.2 (CH$_3$); $^{19}$F NMR (CD$_3$OD): δ −61.7; HRMS-ESI (m/z): [M]$^+$ calcd for C$_{26}$H$_{28}$F$_3$N$_2$Si: 453.19684; found: 453.19603 (0.8 mDa, 1.8 ppm).

[Synthesis of Compound 22]

1-Bromo-4-(trifluoromethyl)benzene (compound L4, 100 μL, 0.470 mmol, 5 Eq) was dissolved in THF (5 mL), and stirred for 10 minutes at −78° C. in an argon atmosphere. 1.1 M sec-butyllithium cyclohexane/n-hexane solution (500 μL, 0.550 mmol, 9 Eq) was added slowly, and stirred for 10 minutes. Compound B1 (20 mg, 0.062 mmol, 1 Eq) was added upon being dissolved in THF (5 mL), and stirred for 10 minutes at −78° C. and for one hour at room temperature. The reaction system was acidified by adding 1N hydrochloric acid. Next, saturated sodium hydrogen carbonate aqueous solution was added, and the reaction system was extracted twice by dichloromethane. The organic phase obtained was washed by saturated saline, dried by anhydrous sodium sulfate, and the solvent was removed under reduced pressure. The residue obtained by purified by HPLC (A/B=90/10 to 10/90, 25 min), and compound 22 (10.0 mg, 29%) was obtained as a blue solid.

$^1$H NMR (CD$_3$OD): δ 7.89 (d, J=8.0 Hz, 2H), 7.51 (d, J=8.0 Hz, 2H), 7.38 (d, J=2.9 Hz, 2H), 7.04 (d, J=9.7 Hz, 2H), 6.79 (dd, J=9.7 Hz, 2.9 Hz, 2H), 3.35 (s, 12H), 0.61 (s, 6H); $^{13}$C NMR (CD$_3$OD): δ 168.4 (C), 155.7 (C), 149.6 (C), 144.8 (C), 142.7 (CH), 131.8 (q, $^2J_{C-F}$=33 Hz, C), 131.3 (CH), 126.4 (q, $^3J_{C-F}$=3.7 Hz, CH), 125.5 (q, $^1J_{C-F}$=273 Hz, C), 122.5 (CH), 115.2 (CH), 40.9 (CH$_3$), −1.1 (CH$_3$); $^{19}$F {$^1$H} NMR (CD$_3$OD): δ −61.7; HRMS-ESI (m/z): [M]$^+$ calcd for C$_{26}$H$_{28}$F$_3$N$_2$Si: 453.19684; found: 453.19653 (0.3 mDa, 0.7 ppm).

Synthesis of Compounds 23-25

Compounds 23-25, which are fluorescent probes of the present invention, were synthesized according to scheme 15 below.

Scheme 15

[Chemical formula 29]

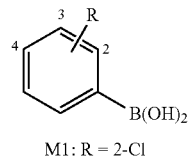

M1: R = 2-Cl
M2: R = 3-CN
M3: R = 4-CN

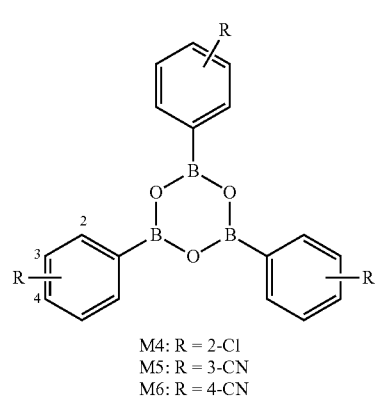

M4: R = 2-Cl
M5: R = 3-CN
M6: R = 4-CN

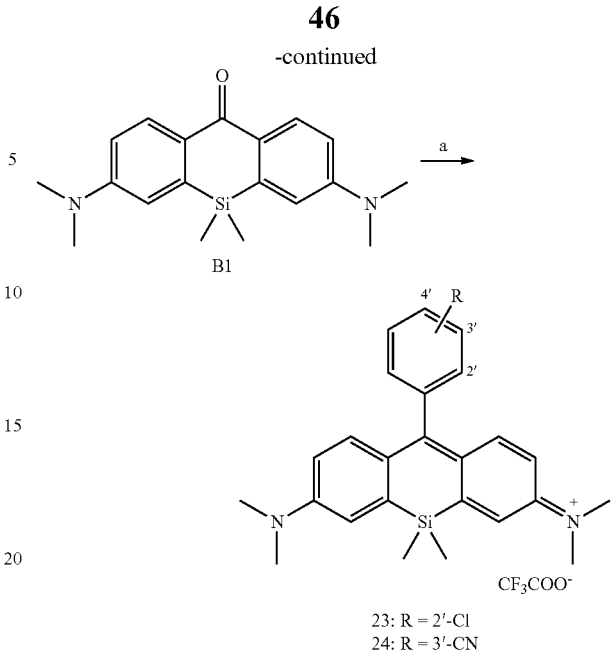

23: R = 2'-Cl
24: R = 3'-CN
25: R = 4'-CN a) 110° C., b) i) Tf$_2$O, MeCN, rt. ii) compound M4-6, PdCl$_2$(PPh$_3$)$_2$, Na$_2$CO$_3$, MeCN

[Synthesis of Compound 23]

2-Chlorophenylboronic acid (compound M1) was dried under reduced pressure for six hours at 110° C., and compound M4 was obtained as a white solid. Compound M4 was used as it was in the next reaction without separation or purification.

Compound B1 (30 mg, 0.092 mmol, 1 Eq) was dissolved in deoxygenated acetonitrile (10 mL), and stirred at room temperature in an argon atmosphere. Trifluoromethanesulfonic anhydride (20 μL, 0.112 mmol, 1.2 Eq) was added slowly. After stirring for another 15 minutes at room temperature, compound M4 (61.1 mg, 0.144 mmol, 1.6 Eq), bis(triphenylphosphine)palladium(II) dichloride (13.1 mg, 0.018 mmol, 0.2 Eq), and sodium carbonate (62.3 mg, 0.587 mmol, 6.2 Eq) were added, and stirred overnight at 70° C. The reaction solution was returned to room temperature, and water was added. The solution was extracted twice by dichloromethane. The organic phase obtained was washed by saturated saline, dried by anhydrous sodium sulfate, and the solvent was removed under reduced pressure. The residue obtained was purified by silica gel column chromatography (eluent: dichloromethane/methanol=100/0 to 90/10) and HPLC (A/B=90/10 to 10/90, 25 min), and the target compound 23 (3.0 mg, 6%) was obtained as a blue solid.

$^1$H NMR (CD$_3$OD): δ 7.65 (dd, J=8.0 Hz, 1.4 Hz, 1H), 7.59 (ddd, J=8.0 Hz, 7.3 Hz, 1.8 Hz, 1H), 7.53 (dt, J=1.4 Hz, 7.3 Hz, 1H), 7.37 (d, J=2.8 Hz, 2H), 7.32 (dd, J=7.3 Hz, 1.8 Hz, 1H), 7.04 (d, J=9.6 Hz, 2H), 6.80 (dd, J=9.6 Hz, 2.8 Hz, 2H), 3.36 (s, 12H), 0.613 (s, 3H), 0.598 (s, 3H); $^{13}$C NMR (CD$_3$OD): δ 167.0 (C), 155.8 (C), 149.5 (C), 142.0 (CH), 139.3 (C), 134.1 (C), 132.2 (CH), 131.7 (CH), 130.9 (CH), 128.4 (C), 128.1 (CH), 122.3 (CH), 115.3 (CH), 40.9 (CH$_3$), −1.1 (CH$_3$), −1.4 (CH$_3$); HRMS-ESI (m/z): [M]$^+$ calcd for C$_{25}$H$_{28}$ClN$_2$Si: 419.17048; found: 419.16962 (0.9 mDa, 2.0 ppm).

[Synthesis of Compound 24]

Compound 24 was also synthesized in the same way in accordance with scheme 15, and the target compound 24 (11.1 mg, 23%) was obtained as a blue solid.

$^1$H NMR (CD$_3$OD): δ 7.95 (ddd, J=7.6 Hz, 1.6 Hz, 1.2 Hz, 1H), 7.77 (dt, J=0.5 Hz, 7.8 Hz, 1H), 7.70 (dt, J=0.5 Hz, 1.6 Hz, 1H), 7.60 (ddd, J=7.8 Hz, 1.6 Hz, 1.2 Hz, 1H), 7.38 (d, J=2.9 Hz, 2H), 7.02 (d, J=9.7 Hz, 2H), 6.80 (dd, J=9.7 Hz, 2.9 Hz, 2H), 3.36 (s, 12H), 0.610 (s, 3H), 0.605 (s, 3H); $^{13}$C NMR (CD$_3$OD): δ 167.1 (C), 155.7 (C), 149.6 (C), 142.7 (CH), 142.0 (C), 135.0 (CH), 133.8 (CH), 133.5 (CH), 130.7 (CH), 128.6 (C), 122.6 (CH), 119.1 (C), 115.2 (CH), 113.9 (C), 40.9 (CH$_3$), −1.10 (CH$_3$), −1.15 (CH$_3$); HRMS-ESI (m/z): [M]$^+$ calcd for C$_{26}$H$_{28}$N$_3$Si: 410.20470; found: 410.20416 (0.5 mDa, 1.3 ppm).

[Synthesis of Compound 25]

Compound 25 was also synthesized in the same way in accordance with scheme 15, and the target compound 25 (9.2 mg, 19%) was obtained as a blue solid.

$^1$H NMR (CD$_3$OD): δ 7.95 (d, J=8.4 Hz, 2H), 7.49 (d, J=8.4 Hz, 2H), 7.38 (d, J=2.9 Hz, 2H), 7.02 (d, J=9.7 Hz, 2H), 6.79 (dd, J=9.7 Hz, 2.9 Hz, 2H), 3.36 (s, 12H), 0.61 (s, 3H); $^{13}$C NMR (CD$_3$OD): δ 167.7 (C), 155.7 (C), 149.6 (C), 145.6 (C), 142.6 (CH), 133.3 (CH), 131.6 (CH), 128.3 (C), 122.6 (CH), 119.1 (C), 115.2 (CH), 113.8 (C), 40.9 (CH$_3$), −1.1 (CH$_3$); HRMS-ESI (m/z): [M]$^+$ calcd for C$_{26}$H$_{28}$N$_3$Si: 410.20470; found: 410.20464 (0.1 mDa, 0.2 ppm).

[Synthesis of Compound 26]

Compound 26, which is a fluorescent probe of the present invention, was synthesized according to scheme 16 below.

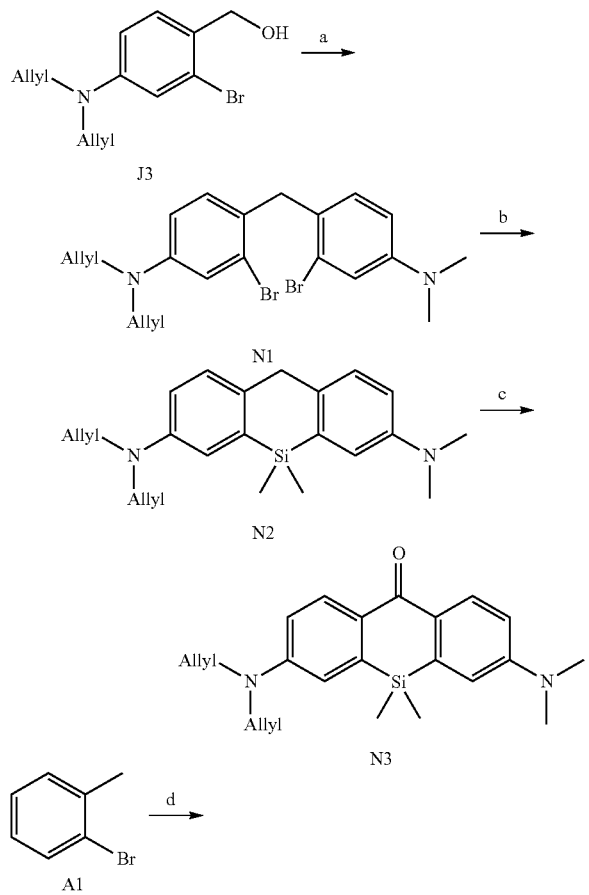

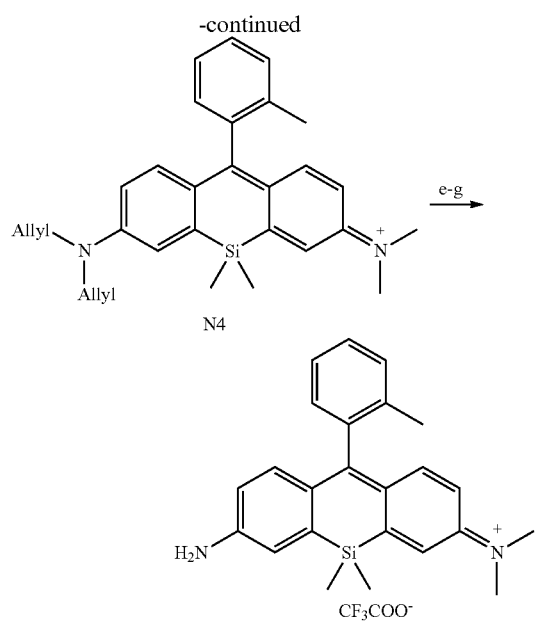

a) 3-bromo-N,N-dimethylaniline, BF$_3$·OEt$_2$ complex, CH$_2$Cl$_2$, reflux, b) i) sec-BuLi, THF, −78° C., ii) SiCl$_2$Me$_2$, THF, −78° C. to rt., iii) 1N HClaq. c) KMnO$_4$, acetone, −15° C., d) i) sec-BuLi, THF, −78° C., ii) compound N3, THF, −78° C. to rt., iii) 1N HClaq., e) NaBH$_4$, MeOH, f) 1,3-dimethylbarbituric acid, Pd(PPh$_3$)$_4$, CH$_2$Cl$_2$, g) p-chloranil, CH$_2$Cl$_2$.

[Synthesis of Compound N1]

Compound J3 (1.00 g, 3.54 mmol, 1 Eq) and 3-bromo-N,N-dimethylaniline (0.540 μL, 3.72 mmol, 1.05 Eq) were dissolved in dichloromethane (15 mL), and stirred on an ice bath. Boron trifluoride-diethyl ether complex (650 μL, 5.46 mmol, 1.5 Eq) was added, and the reaction solution was heated and refluxed overnight. After air-cooling, saturated sodium carbonate aqueous solution was added, and the reaction system was extracted by dichloromethane. The organic phase obtained was washed by saturated saline, dried by anhydrous sodium sulfate, and the solvent was removed under reduced pressure. The residue obtained was separated and purified by silica gel column chromatography (eluent: hexane/ethyl acetate=100/0 to 50/50), and compound N1 (1.39 g, 85%) was obtained as a colorless, transparent liquid.

$^1$H NMR (CDCl$_3$): δ 6.93 (d, J=2.7 Hz, 1H), 6.90 (d, J=2.7 Hz, 1H), 6.86 (d, J=8.6 Hz, 1H), 6.80 (d, J=8.6 Hz, 1H), 6.59 (dd, J=8.6 Hz, 2.7 Hz, 1H), 6.54 (dd, J=8.6 Hz, 2.7 Hz, 1H), 5.83 (ddt, J=17.5 Hz, 10.0 Hz, 4.9 Hz, 2H), 5.18-5.14 (m, 4H), 3.98 (s, 2H), 3.88-3.87 (m, 4H), 2.91 (s, 6H); $^{13}$C NMR (CDCl$_3$): δ 150.2 (C), 148.3 (C), 133.7 (CH), 130.96 (CH), 130.86 (CH), 127.25 (C), 127.06 (C), 125.75 (C), 125.67 (C), 116.41 (CH$_2$), 116.39 (CH), 116.1 (CH), 112.0 (CH), 111.8 (CH), 52.9 (CH$_2$), 40.7 (CH$_3$), 39.9 (CH$_2$); HRMS-ESI (m/z): [M+H]$^+$ calcd for C$_{21}$H$_{25}$Br$_2$N$_2$: 463.03790; found: 463.03667 (1.2 mDa, 2.7 ppm).

[Synthesis of Compound N3]

Compound J6 (1.05 g, 2.26 mmol, 1 Eq) was dissolved in THF (30 mL) in an argon atmosphere, and stirred for 10 minutes at −78° C. 1 M sec-butyllithium cyclohexane/n-hexane solution (5.0 mL, 5.0 mmol, 2.2 Eq) was added slowly, and the combination was stirred for 10 minutes. Next, the reaction system was returned to room temperature gradually by adding dichlorodimethylsilane (350 μL, 2.88 mmol, 1.3 Eq) diluted by THF (5 mL), and stirred for 2.5 hours. The reaction system was acidified by adding 1N hydrochloric acid. Next, saturated sodium hydrogen carbonate aqueous solution was added, and the THF was distilled off under reduced pressure. The water layer obtained was extracted by ethyl acetate. Next, the organic phase was washed by water and saturated saline, dried by anhydrous sodium sulfate, and the solvent was removed under reduced pressure. The residue obtained was purified by medium-pressure silica gel chromatography (eluent: n-hexane/ethyl acetate=100/0 to 90/10). The compound obtained was dissolved in acetone (15 mL), and stirred for 10 minutes at −15° C. Potassium permanganate (450 mg, 2.85 mmol, 1.3 Eq) was added divided over three times over 10 minutes, and completion of the reaction was confirmed by TLC. The reaction system was filtered by Celite, washed by dichloromethane, and the filtrate was distilled off under reduced pressure. The residue obtained was purified by silica gel chromatography (eluent: hexane/dichloromethane=40/60 to 0/100), and the target compound N3 (123 mg, 14%) was obtained as a yellow solid.

$^1$H NMR (CDCl$_3$): δ 8.38 (d, J=9.0 Hz, 1H), 8.35 (d, J=8.8 Hz, 1H), 6.83 (dd, J=9.0 Hz, 2.9 Hz, 1H), 6.83-6.80 (m, 2H), 6.78 (d, J=2.8 Hz, 1H), 5.88 (ddt, J=17.2 Hz, 9.8 Hz, 4.8 Hz, 2H), 5.23-5.18 (m, 4H), 4.03-4.02 (m, 4H), 3.09 (s, 6H), 0.44 (s, 6H); $^{13}$C NMR (CDCl$_3$): δ 185.1 (C), 151.4 (C), 150.1 (C), 140.5 (C), 133.0 (CH), 131.6 (CH), 129.9 (C), 129.6 (0), 116.6 (CH$_2$), 144.8 (CH), 144.3 (CH), 113.4 (CH), 113.1 (CH), 52.7 (CH$_2$), 40.0 (CH$_3$), −1.0 (CH$_3$); HRMS-ESI (m/z): [M+H]$^+$ calcd for C$_{23}$H$_{29}$N$_2$OSi: 377.20437; found: 377.20398 (0.4 mDa, 1.0 ppm).

[Synthesis of Compound 26]

2-Bromotoluene (compound A1, 50 μL, 0.420 mmol, 12 Eq) was dissolved in THF (5 mL), and stirred for 10 minutes at −78° C. in an argon atmosphere. 1 M sec-butyllithium cyclohexane/n-hexane solution (200 μL, 0.200 mmol, 5.7 Eq) was added slowly, and stirred for 10 minutes. Compound N3 (13.2 mg, 0.035 mmol, 1 Eq) was added upon being dissolved in THF (5 mL), and stirred for one hour at −78° C. and for two hours at room temperature. The reaction system was acidified by adding 1N hydrochloric acid. Next, saturated sodium hydrogen carbonate aqueous solution was added, and the reaction system was extracted twice by dichloromethane. The organic phase obtained was washed by saturated saline, dried by anhydrous sodium sulfate, and the solvent was removed under reduced pressure. The compound obtained was dissolved in methanol (2 mL), and sodium borohydride was added until the color of the solution became pale yellow. The reaction was stopped by adding water, and the reaction system was extracted by ethyl acetate. The organic layer obtained was washed by saturated saline, dried by anhydrous sodium sulfate, and the solvent was removed under reduced pressure. The compound obtained was dissolved in deoxygenated dichloromethane (3 mL), and 1,3-dimethylbarbituric acid (68.1 mg, 0.436 mmol, 12 Eq) and tetrakis(triphenylphosphine)palladium (4.2 mg, 4 μmol, 0.1 Eq) were added, and stirred for 1.5 hour at 40° C. Chloranil (10.5 mg, 0.042 mmol, 1.2 Eq) was added, and stirred for 10 minutes at room temperature. The dark blue reaction solution was separated by silica gel column chromatography (eluent: dichloromethane/methanol=100/0 to 60/40). The blue fraction was recovered, and the solvent was distilled off under reduced pressure. The residue obtained was purified by HPLC (A/B=90/10 to 10/90, 25 min), and the target compound 26 (12.0 mg, 71%) was obtained as a bluish-violet solid.

$^1$H NMR (CD$_3$OD): δ 7.47-7.37 (m, 3H), 7.35 (d, J=2.8 Hz, 1H), 7.21 (m, 1H), 7.11 (d, J=8.5 Hz, 1H), 7.09 (d, J=9.7 Hz, 1H), 7.02 (d, J=9.3 Hz, 1H), 6.76 (dd, J=9.7 Hz, 2.8 Hz, 1H), 6.57 (dd, J=9.3 Hz, 2.5 Hz, 1H), 3.34 (s, 6H), 2.04 (s, 3H), 0.581 (s, 3H), 0.565 (s, 3H); $^{13}$C NMR (CD$_3$OD): δ 171.4 (C), 158.5 (C), 155.8 (C), 150.7 (C), 149.3 (C), 143.6 (CH), 142.6 (CH), 140.1 (C), 136.9 (C), 131.3 (CH), 130.09 (CH), 130.04 (CH), 128.7 (C), 128.3 (C), 126.8 (CH), 124.4 (CH), 122.1 (CH), 116.9 (CH), 115.1 (CH), 40.9 (CH$_3$), 19.4 (CH$_3$), −1.3 (CH$_3$), −1.5 (CH$_3$); HRMS-ESI (m/z): [M]$^+$ calcd for C$_{24}$H$_{27}$N$_2$Si: 371.19380; found: 371.19406 (−0.3 mDa, −0.7 ppm).

[Synthesis of Compound 27]

Compound 27, which is a fluorescent probe of the present invention, was synthesized according to scheme 17 below.

Scheme 17

[Chemical formula 31]

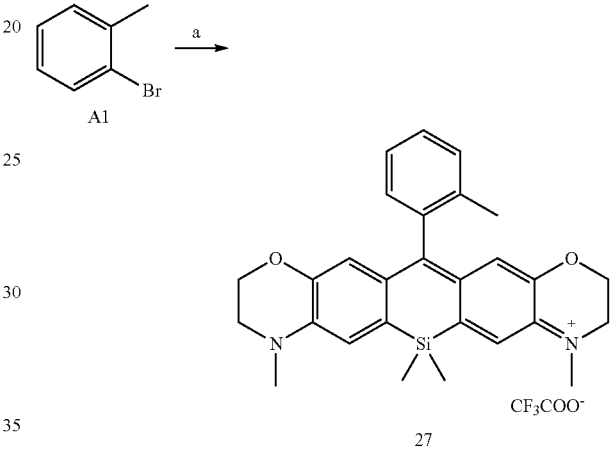

a) i) sec-BuLi, THF, −78° C., ii) compound E8, THF, −78° C. to rt., iii) 1N HClaq.

[Synthesis of Compound 27]

2-Bromotoluene (compound A1, 20 μL, 0.180 mmol, 6 Eq) was dissolved in THF (5 mL), and stirred for 10 minutes at −78° C. in an argon atmosphere. 1 M sec-butyllithium cyclohexane/n-hexane solution (100 μL, 0.100 mmol, 3.3 Eq) was added slowly, and stirred for 10 minutes. Compound E8 (11.5 mg, 0.030 mmol, 1 Eq) was added upon being dissolved in THF (5 mL), and stirred for two hours while gradually returning to room temperature. The reaction system was acidified by adding 1N hydrochloric acid. Next, saturated sodium hydrogen carbonate aqueous solution was added, and the reaction system was extracted three times by dichloromethane. The organic phase obtained was washed by saturated saline, dried by anhydrous sodium sulfate, and the solvent was removed under reduced pressure. The residue obtained was purified by HPLC (A/B=90/10 to 10/90, 25 min), and the target compound 27 (9.8 mg, 57%) was obtained as a bluish-green solid.

$^1$H NMR (CD$_3$CN): δ 7.48-7.44 (m, 1H), 7.41-7.35 (m, 2H), 7.23 (s, 2H), 7.10 (d, J=7.4 Hz, 1H), 6.34 (s, 2H), 4.12 (t, J=4.6 Hz, 4H), 3.64 (t, J=4.6 Hz, 4H), 3.31 (s, 6H), 2.01 (s, 3H), 0.56 (s, 3H), 0.54 (s, 3H); $^{13}$C NMR (CD$_3$CN): δ 169.6 (C), 145.5 (C), 145.0 (C), 144.7 (C), 140.1 (C), 136.5 (C), 131.2 (CH), 129.91 (C), 129.88 (CH), 129.6 (CH), 126.6 (CH), 123.3 (CH), 121.1 (CH), 64.0 (CH$_2$), 50.4 (CH$_2$), 39.6 (CH$_3$), 19.5 (CH$_3$), −1.1 (CH$_3$), −1.2 (CH$_3$). HRMS-ESI (m/z): [M]$^+$ calcd for C$_{28}$H$_{31}$N$_2$O$_2$Si: 455.21493; found: 455.21407 (0.9 mDa, 1.9 ppm).

[Synthesis of Compound 28]

Compound 28, which is a fluorescent probe of the present invention, was synthesized according to scheme 18 below.

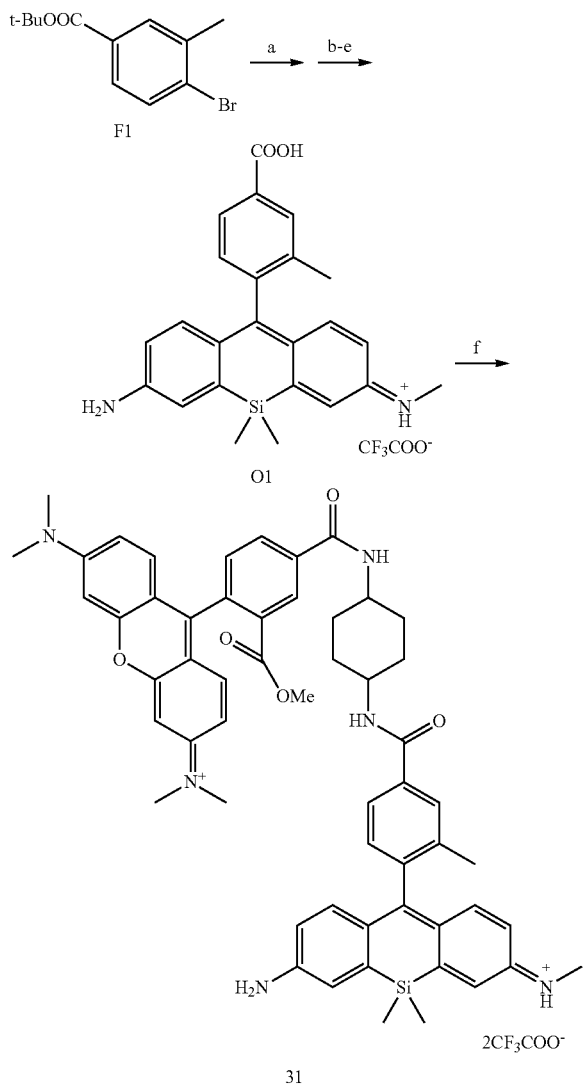

Scheme 18

[Chemical formula 32]

a) i) sec-BuLi, THF, -78° C., ii) compound J8, THF, -78° C. to rt., iii) 1N HClaq.;
b) NaBH₄, MeOH, 0° C., c) 1,3-dimethylbarbituric acid, Pd(PPh₃)₄, CH₂Cl₂;
d) p-chloranil, CH₂Cl₂, rt.; e) TFA, CH₂Cl₂, rt.; f) compound G1, PyBOP, DIEA, DMF, rt.

[Synthesis of Compound O1]

Compound F1 (150 mg, 0.550 mmol, 12 Eq) was dissolved in THF (5 mL), and stirred for 10 minutes at −78° C. in an argon atmosphere. 1.6 M tert-butyllithium pentane solution (300 μL, 0.472 mmol, 10 Eq) was added slowly, and stirred for 10 minutes. Compound J8 (19 mg, 0.047 mmol, 1 Eq) was added upon being dissolved in THF (5 mL), and stirred for one hour at −78° C. and for two hours at room temperature. The reaction system was acidified by adding 1N hydrochloric acid. Next, saturated sodium hydrogen carbonate aqueous solution was added, and the reaction system was extracted twice by dichloromethane. The organic phase obtained was washed by saturated saline, dried by anhydrous sodium sulfate, and the solvent was removed under reduced pressure. The compound obtained was dissolved in methanol (2 mL), and sodium borohydride was added until the color of the solution became pale yellow. The reaction was stopped by adding water, and the reaction system was extracted by ethyl acetate. The organic layer obtained was washed by saturated saline, dried by anhydrous sodium sulfate, and the solvent was removed under reduced pressure. The compound obtained was dissolved in deoxygenated dichloromethane (2 mL), and 1,3-dimethyl-barbituric acid (145 mg, 0.922 mmol, 20 Eq) and tetrakis (triphenylphosphine)palladium (6.0 mg, 5 μmol, 0.1 Eq) were added, and stirred for one hour at 40° C. Chloranil (15.1 mg, 0.061 mmol, 1.3 Eq) was added, and stirred for 10 minutes at room temperature. The dark blue reaction solution was separated by silica gel column chromatography (eluent: dichloromethane/methanol=100/0 to 60/40, 0.5% TFA). The blue fraction was recovered, and the solvent was distilled off under reduced pressure. The compound obtained was dissolved in trifluoroacetic acid (1 mL) and water (200 μL), and stirred for 30 minutes at room temperature. The solvent was distilled off under reduced pressure. The residue obtained was purified by HPLC (first time: A/B=90/10 to 10/90, 25 min; second time: 70/30 to 30/70), and the target compound 01 (16.2 mg, 67%) was obtained as a bluish-violet solid.

$^1$H NMR (CD₃OD): δ 8.06 (s, 1H), 8.02 (d, J=7.9 Hz, 1H), 7.25 (d, J=7.8 Hz, 1H), 7.22 (d, J=2.2 Hz, 1H), 7.20 (d, J=2.5 Hz, 1H), 7.02 (br s, 1H), 6.94 (d, J=9.3 Hz, 1H), 6.62 (dd, J=9.4 Hz, 1.8 Hz, 1H), 6.58 (dd, J=9.3 Hz, 2.5 Hz, 1H), 3.07 (s, 3H), 2.11 (s, 3H), 0.562 (s, 3H), 0.549 (s, 3H); $^{13}$C NMR (CD₃OD): δ 169.8 (C), 169.2 (C), 158.4 (C), 157.5 (C), 150.0 (C), 144.9 (C), 143.1 (CH), 137.6 (C), 132.57 (C), 132.47 (CH), 130.5 (C), 128.08 (CH), 128.04 (C), 127.97 (C), 124.5 (CH), 117.0 (CH), 30.1 (CH₃), 19.4 (CH₃), −1.4 (CH₃), −1.6 (CH₃); HRMS-ESI (m/z): [M]⁺ calcd for C₂₄H₂₅N₂O₂Si: 401.16798; found: 401.16723 (0.8 mDa, 1.9 ppm).

[Synthesis of Compound 28]

Compound G1 (2.9 mg, 3.8 μL, 1 Eq), compound 01 (2.4 mg, 4.5 μmol, 1.2 Eq), and (benzotriazol-1-yloxy) tripyrrolidinophosphonium hexafluorophosphate (4.0 mg, 7.6 μmol, 2.0 Eq) were dissolved in DMF (200 μL), and stirred at room temperature. N,N-diisopropylethylamine (10 μL, 56 μmol, 15 Eq) was added, and stirred for another 1.5 hour at room temperature. The solvent was distilled off under reduced pressure. The residue obtained was separated and purified by HPLC (first time: A/B=90/10 to 10/90, 25 min/second time: C/B=90/10 to 10/90, 25 min), and the target compound 28 (2.3 mg, 53%) was obtained as a dark violet solid.

$^1$H NMR (CD₃OD): δ 8.79-8.77 (m, 1H, NH), 8.77 (d, J=1.5 Hz, 1H), 8.50 (d, J=7.9 Hz, 1H, NH), 8.31 (dd, J=7.9 Hz 1.5 Hz, 1H), 7.89 (s, 1H), 7.85 (d, J=7.8 Hz, 1H), 7.57 (d, J=7.9 Hz, 1H), 7.26 (d, J=7.8 Hz, 1H), 7.22 (brs, 1H), 7.21 (d, J=2.4 Hz, 1H), 7.13 (d, J=9.4 Hz, 2H), 7.07 (dd, J=9.5 Hz, 2.3 Hz, 2H), 7.03 (d, J=2.3 Hz, 2H), 7.09-7.02 (m, 1H), 6.97 (d, J=9.3 Hz, 1H), 6.62 (d, J=8.4 Hz, 1H), 6.57 (dd, J=9.3 Hz, 2.4 Hz), 4.03 (m, 2H), 3.66 (s, 3H), 3.33 (s, 12H), 3.08 (s, 3H), 2.18-2.16 (m, 4H), 2.13 (s, 3H), 1.72-1.61 (m, 4H), 0.571 (s, 3H), 0.558 (s, 3H); $^{13}$C NMR (CD₃OD) δ 170.0 (C), 169.0 (C), 167.5 (C), 166.4 (C), 165.5 (C), 159.9 (C), 159.09 (C), 159.06 (C), 158.4 (C), 150.2 (C), 143.4 (C), 143.2 (CH), 138.01 (C), 137.93 (C), 137.6 (C), 136.5 (C), 132.7 (CH), 132.08 (CH), 131.94 (CH), 131.84 (CH), 131.1 (CH), 130.5 (CH), 130.2 (CH), 128.19 (C), 128.12 (CH), 125.8 (CH), 124.4 (CH), 116.9 (CH), 115.7 (CH), 114.7 (C), 97.6 (CH), 53.1 (CH₃), 50.2 (CH), 49.9

(CH), 41.0 (CH$_3$), 32.35 (CH$_2$), 32.32 (CH$_2$), 30.1 (CH$_3$), 19.5 (CH$_3$), −1.44 (CH$_3$), −1.63 (CH$_3$); HRMS-ESI (m/z): [M]$^{2+}$/2 calcd for C$_{56}$H$_{60}$N$_6$O$_5$Si: 462.21917; found: 462.21878 (0.4 mDa, 0.9 ppm).

[Synthesis of Compound 29]

Compound 29, which is a fluorescent probe of the present invention, was synthesized according to scheme 19 below.

Scheme 33

[Chemical formula 33]

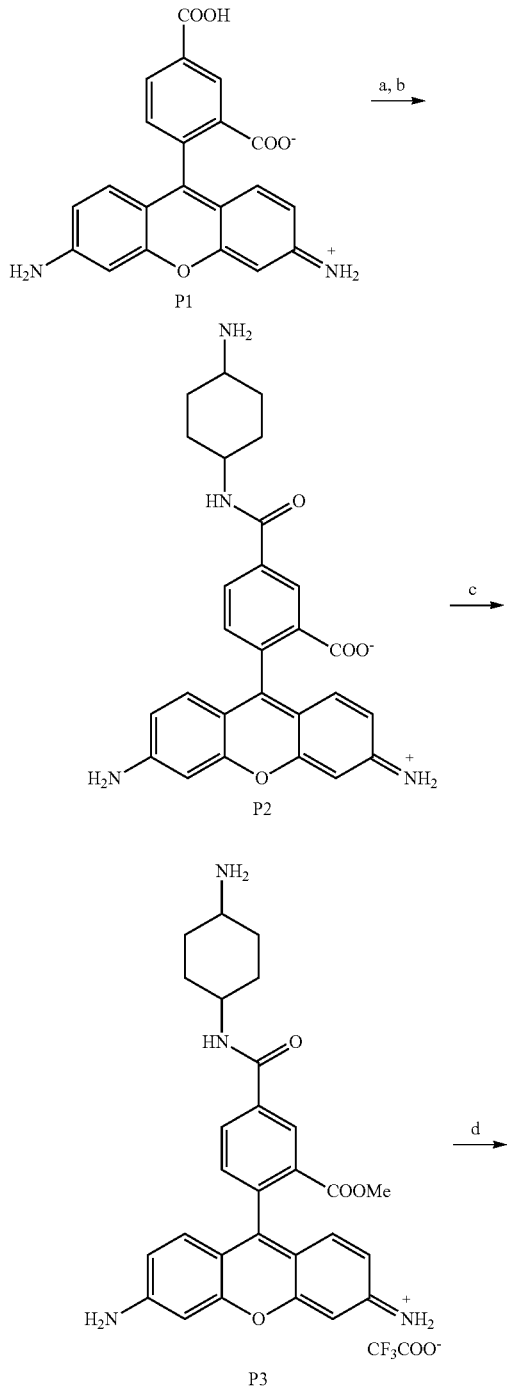

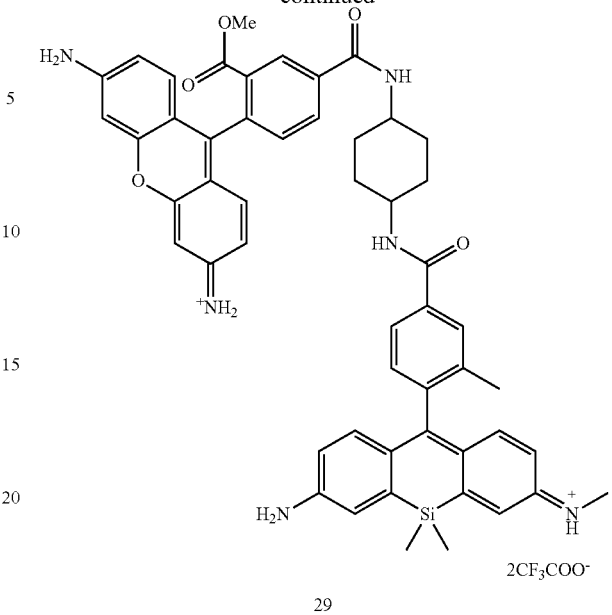

a) compound F5, PyBOP, DIEA, DMA, b) TFA, rt., c) conc. H$_2$SO$_4$, MeOH, reflux, d) compound O1, PyBOP, DIEA, DMF, rt.

[Synthesis of Compound P2]

Compound P1 (15.0 mg, 31 µmol, 1 Eq), compound F5 (10.5 mg, 49 µmol, 1.6 Eq), and hexafluorophosphoric acid (benzotriazol-1-yloxy)tripyrrolidinophosphonium (26.0 mg, 50 µmol, 1.5 Eq) were dissolved in DMF (500 µL), and stirred at room temperature. N,N-diisopropylethylamine (40 µL, 230 µmol, 7.5 Eq) was added, and stirred for another hour at room temperature. The solvent was distilled off under reduced pressure. The residue obtained was separated and purified by HPLC (first time: A/B=90/10 to 10/90, 25 min; second time: C/B=90/10 to 10/90, 25 min), and the target compound P2 (5.0 mg, 23%) was obtained as an orange solid.

$^1$H NMR (CD$_3$OD): δ 8.74 (d, J=1.7 Hz, 1H), 8.74 (d, J=7.4 Hz, 1H, CONH), 8.24 (dd, J=8.0 Hz, 1.8 Hz, 1H), 7.51 (d, J=8.0 Hz, 1H), 7.03 (d, J=8.9 Hz, 2H), 6.83 (d, J=2.1 Hz, 2H), 6.81 (dd, J=8.9 Hz, 2.1 Hz, 2H), 3.98 (m, 1H), 3.16 (m, 1H), 2.18-2.15 (m, 4H), 1.65-1.54 (m, 4H); $^{13}$C NMR (CD$_3$OD): δ 167.8 (C), 167.4 (C), 161.3 (C), 161.1 (C), 160.0 (C), 138.2 (C), 137.7 (C), 132.77 (C), 132.69 (CH), 132.4 (CH), 131.9 (CH), 131.3 (CH), 117.9 (CH), 114.7 (C), 98.4 (CH), 50.6 (CH), 49.5 (CH), 31.1 (CH$_2$), 30.7 (CH$_2$); HRMS-ESI (m/z): [M]$^+$ calcd for C$_{27}$H$_{27}$N$_4$O$_4$: 471.20268; found: 471.20113 (1.6 mDa, 3.3 ppm).

[Synthesis of Compound P3]

Compound P2 (5.0 mg, 7 µmol, 1 Eq) was dissolved in methanol (2 mL). Three drops of concentrated sulfuric acid were added, and the reaction system was stirred overnight while heating and refluxing. The reaction system was returned to room temperature, and the solvent was distilled off under reduced pressure. The residue obtained was purified by HPLC (A/B=90/10 to 10/90, 25 min), and compound P3 (4.6 mg, 90%) was obtained as an orange solid.

$^1$H NMR (CD$_3$OD): δ 8.75 (d, J=7.9 Hz, 1H, CONH), 8.73 (d, J=1.7 Hz, 1H), 8.26 (dd, J=8.0 Hz, 1.8 Hz, 1H), 7.54 (d, J=8.0 Hz, 1H), 7.01 (d, J=9.1 Hz, 2H), 6.84 (d, J=2.1 Hz, 2H), 6.81 (dd, J=9.1 Hz, 2.1 Hz, 2H), 3.98 (m, 1H), 3.67 (s, 3H), 3.17 (m, $^1$H), 2.18-2.16 (m, 4H), 1.65-1.55 (m, 4H); $^{13}$C NMR (CD$_3$OD): δ 167.6 (C), 166.3 (C), 161.4 (C), 160.3 (C), 159.7 (C), 138.0 (C), 137.8 (C), 132.63 (CH), 132.61 (CH), 132.02 (CH), 131.85 (C), 131.1 (CH), 118.0 (CH), 114.6 (C), 98.5 (CH), 53.1 (CH$_3$), 50.6 (CH), 49.5 (CH), 31.1 (CH$_2$), 30.7 (CH$_2$); HRMS-ESI (m/z): [M]$^+$ calcd for C$_{28}$H$_{29}$N$_4$O$_4$: 485.21833; found: 485.21863 (−0.3 mDa, −0.6 ppm).

[Synthesis of Compound 29]

Compound P3 (2.6 mg, 3.7 μmol, 1 Eq), compound 01 (2.3 mg, 4.4 μmol, 1.2 Eq), and (benzotriazol-1-yloxy)tripyrrolidinophosphonium hexafluorophosphate (3.3 mg, 6.3 μmol, 1.7 Eq) were dissolved in DMF (200 μL), and stirred at room temperature. N,N-diisopropylethylamine (5 μL, 27 μmol, 7.5 Eq) was added, and stirred for another hour at room temperature. The solvent was distilled off under reduced pressure. The residue obtained was separated by purified by HPLC (A/B=90/10 to 10/90, 25 min), and the target compound 29 (3.0 mg, 75%) was obtained as a dark orange solid.

$^1$H NMR (CD$_3$OD): δ 8.76 (d, J=7.4 Hz, 1H, —CONH—), 8.76 (d, J=1.8 Hz, 1H), 8.50 (d, J=8.0 Hz, 1H, —CONH—), 8.29 (dd, J=8.0 Hz, 1.8 Hz, 1H), 7.89 (d, J=1.5 Hz, 1H), 7.85 (dd, J=7.9 Hz, 1.5 Hz, 1H), 7.55 (d, J=7.9 Hz, 1H), 7.26 (d, J=7.9 Hz, 1H), 7.22 (br s, 1H), 7.20 (d, J=2.5 Hz), 7.03 (d, J=9.1 Hz, 2H), 7.03 (m, 1H)*, 6.98 (d, J=9.3 Hz, 1H), 6.85 (d, J=2.1 Hz, 2H), 6.82 (dd, J=9.1 Hz, 2.1 Hz, 2H), 6.62 (d, J=9.2 Hz, 1H), 6.57 (dd, J=9.3 Hz, 2.5 Hz, 1H), 4.03 (m, 2H), 3.68 (s, 3H), 3.08 (s, 3H), 2.17-2.15 (m, 4H), 2.13 (s, 3H), 1.72-1.60 (m, 4H), 0.570 (s, 3H), 0.558 (s, 3H); HRMS-ESI (m/z): [M]$^{2+}$/2 calcd for C$_{55}$H$_{55}$N$_6$O$_5$Si: 434.18787; found: 434.18723 (0.6 mDa, 1.5 ppm).

[Synthesis of Compounds 30 and 31]

Compounds 30 and 31, which are fluorescent probes of the present invention, were synthesized according to scheme 20 below.

Scheme 20

[Chemical formula 34]

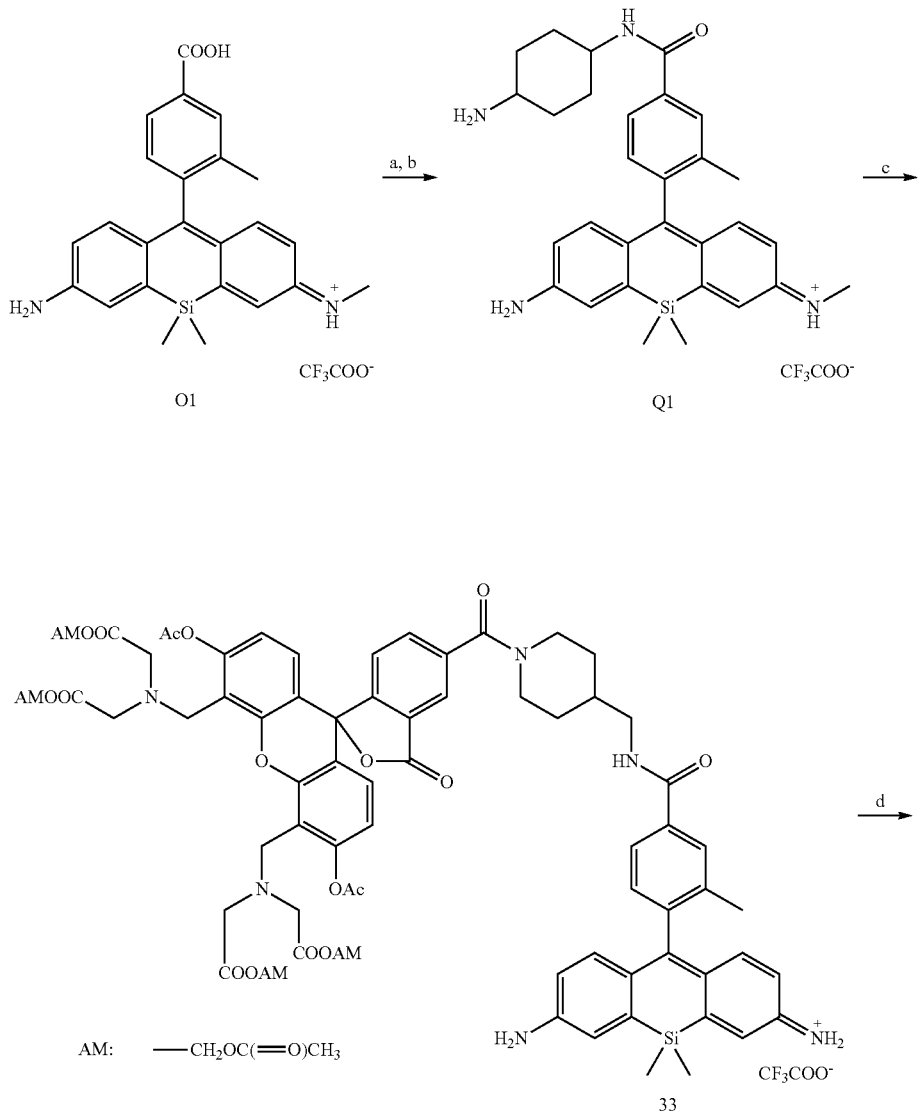

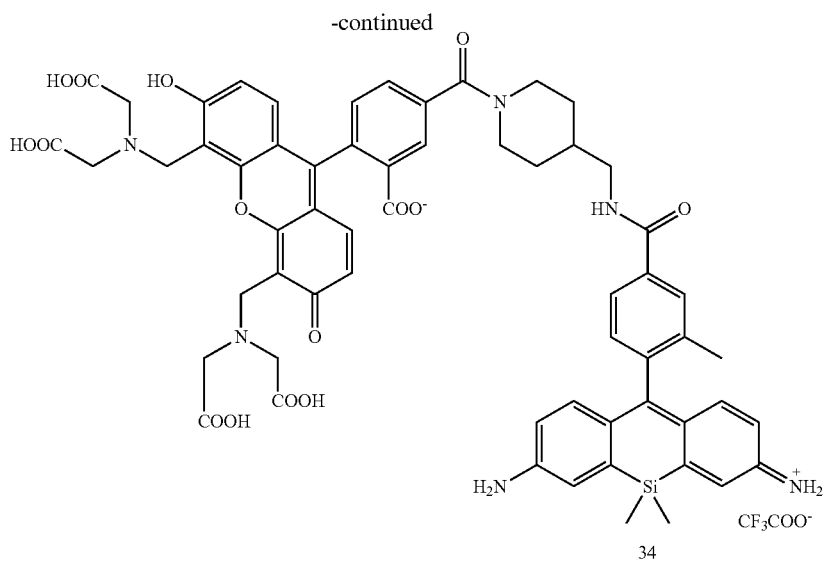

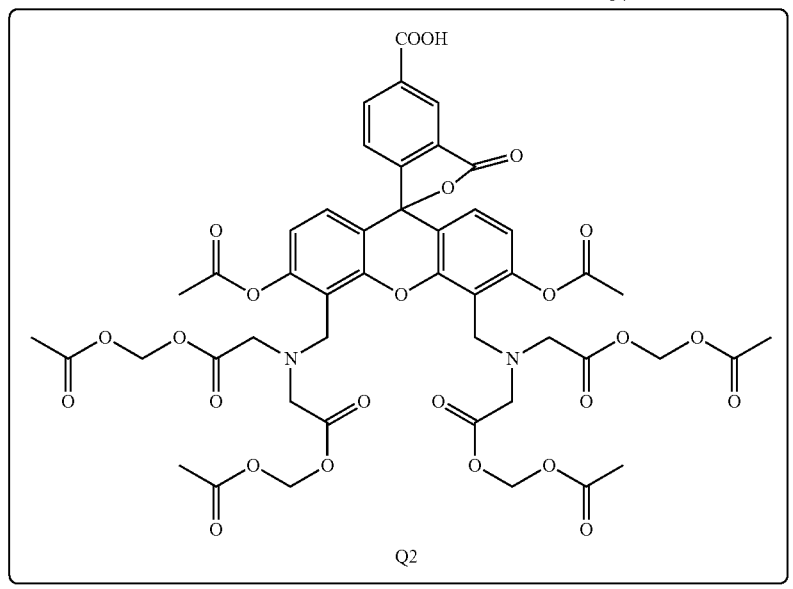

a) compound F5, PyBOP, DIEA, DMF, rt.;
b) TFA, rt.;
c) compound Q2, PyBOP, DIEA, DMF, rt.
d) 1N NaOH, MeOH, rt.

[Synthesis of Compound Q1]

Compound O1 (5.1 mg, 0.010 mmol, 1 Eq), trans-N-Boc-1,4-cyclohexanediamine (compound F5, 4.0 mg, 0.019 mmol, 1.9 Eq), and (benzotriazol-1-yloxy)tripyrrolidinophosphonium hexafluorophosphate (9.1 mg, 0.018 mmol, 1.7 Eq) were dissolved in DMF (400 µL), and stirred at room temperature. N,N-diisopropylethylamine (15 µL, 0.088 mmol, 8.8 Eq) was added, and stirred for another 30 minutes. The solvent was distilled off under reduced pressure. Trifluoroacetic acid (1 mL) and water (100 µL) were added to the residue, and stirred for 30 minutes at room temperature. The solvent was distilled off under reduced pressure. The residue obtained was purified by HPLC (A/B=90/10 to 10/90, 25 min), and compound Q1 (6.8 mg, 95%) was obtained as a bluish-violet solid.

$^1$H NMR (CD$_3$OD): δ 8.48 (d, J=7.8 Hz, 1H, NH), 7.86 (s, 1H), 7.82 (d, J=7.9 Hz, 1H), 7.24 (d, J=7.9 Hz, 1H), 7.21 (s, 1H), 7.20 (d, J=2.4 Hz, 1H), 7.02 (br s, 1H), 6.94 (d, J=9.3 Hz, 1H), 6.61 (d, J=8.8 Hz, 1H), 6.56 (dd, J=9.3 Hz, 2.4 Hz, 1H), 3.95 (m, 1H), 3.15 (m, 1H), 3.07 (s, 3H), 2.14 (d, J=6.9 Hz, 4H), 2.11 (s, 3H), 1.64-1.52 (m, 4H), 0.560 (s, 3H), 0.548 (s, 3H); $^{13}$C NMR (CD$_3$OD): δ 169.9 (C), 169.1 (C), 158.3 (C), 157.5 (C), 150.1 (C), 143.5 (C), 143.1 (CH), 137.6 (C), 136.3 (C), 130.45 (CH), 130.19 (CH), 128.15 (C), 128.07 (C), 125.8 (CH), 124.4 (CH), 116.9 (CH), 50.6 (CH), 31.1 (CH$_2$), 30.7 (CH$_2$), 30.0 (CH$_3$), 19.5 (CH$_3$), −1.46 (CH$_3$), −1.65 (CH$_3$); HRMS-ESI (m/z): [M]$^+$ calcd for C$_{30}$H$_{37}$N$_4$OSi: 497.27311; found: 497.27302 (0.1 mDa, 0.2 ppm).

[Synthesis of Compound 30]

Compound Q1 (3.4 mg, 4.7 µmol, 1 Eq), compound Q2 (7.4 mg, 7.0 µmol, 1.2 Eq), and (benzotriazol-1-yloxy)tripyrrolidinophosphonium hexafluorophosphate (5.8 mg, 11 µmol, 2.2 Eq) were dissolved in DMF (300 µL), and stirred at room temperature. N,N-diisopropylethylamine (8 µL, 70 µmol, 10 Eq) was added, and stirred for another 30 minutes at room temperature. The solvent was distilled off under reduced pressure. The residue obtained was separated and purified by HPLC (A/B=70/30 to 30/70, 25 min), and the target compound 30 (1.8 mg, 24%) was obtained as a bluish-violet solid.

$^1$H NMR (CD$_3$OD): δ 8.68 (d, J=7.9 Hz, 1H, NH), 8.48 (s, 1H), 8.47 (d, J=7.9 Hz, 1H, NH), 8.23 (dd, J=8.0 Hz, 1.4 Hz, 1H), 7.88 (s, 1H), 7.84 (d, J=7.8 Hz, 1H), 7.41 (d, J=8.0 Hz, 1H), 7.25 (d, J=7.9 Hz, 1H), 7.21 (br s, 1H), 7.20 (d, J=2.5 Hz, 1H), 7.05 (br s, 1H), 6.97 (d, J=9.3 Hz, 1H), 6.93 (s, 4H), 6.62 (d, J=8.5 Hz, 1H), 6.57 (dd, J=9.3 Hz, 2.4 Hz, 1H), 5.71 (d, $^2$J$_{H-H}$=7.2 Hz, 4H), 5.70 (d, $^2$J$_{H-H}$=7.2 Hz, 4H), 4.37 (d, $^2$J$_{H-H}$=12.6 Hz, 2H), 4.33 (d, $^2$J$_{H-H}$=12.6 Hz, 2H), 4.00 (m, 2H), 3.74 (s, 8H), 3.08 (s, 3H), 2.35 (s, 6H), 2.15-2.14 (m, 4H), 2.12 (s, 3H), 1.99 (s, 12H), 1.68-1.57 (m, 4H), 0.567 (s, 3H), 0.555 (s, 3H); HRMS-ESI (m/z): [M+Na]$^{2+}$/2 calcd for C$_{77}$H$_{81}$N$_6$NaO$_{25}$Si: 770.24537; found: 770.24500 (0.4 mDa, 0.5 ppm).

[Synthesis of Compound 31]

Compound 30 (0.24 mg, 0.15 μmol, 1 Eq) was dissolved in methanol (40 μL), and stirred at room temperature. 1N sodium hydroxide aqueous solution (10 μL) was added, and stirred for five minutes. The reaction was stopped (*4) by adding methanol (0.1% trifluoroacetic acid). Separation and purification were performed by HPLC (A/B=90/10 to 10/90, 25 min), and the target compound 31 was obtained as a bluish-violet solid.

HRMS-ESI (m/z): [M+H]$^+$ calcd for C$_{61}$H$_{61}$N$_6$O$_{15}$Si: 1145.39587; found: 1145.39346 (2.4 mDa, 2.1 ppm.)

[Synthesis of Compound 32]

Compound 32, which is a fluorescent probe of the present invention, was synthesized according to scheme 21 below.

Scheme 21

[Chemical formula 35]

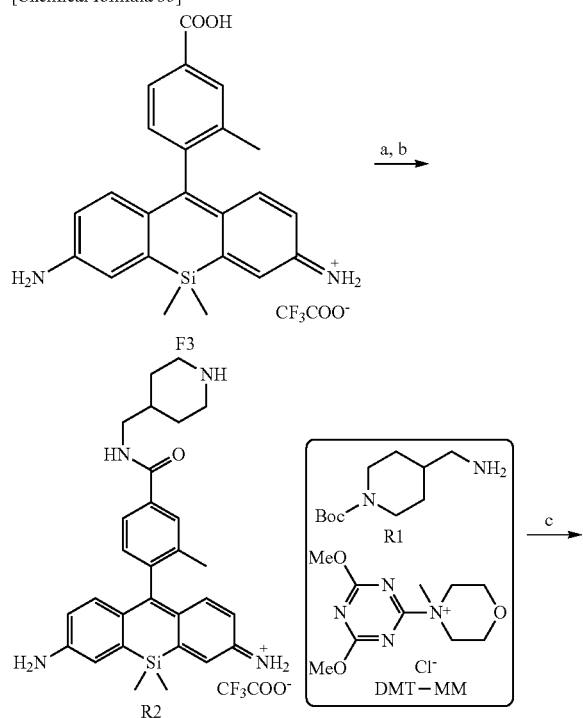

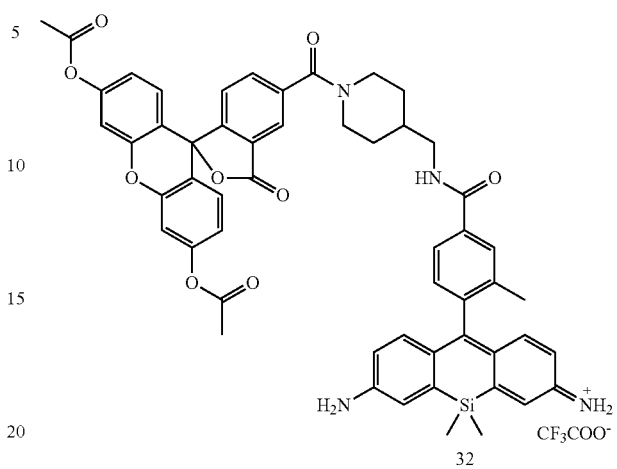

a) compound R1, DMT—MM, DIEA, DMF, rt.;
b) TFA, rt.;
c) compound H2, DMT—MM, DIEA, DMF, rt.

[Synthesis of Compound R2]

Compound F3 (5.9 mg, 15.2 μmol), N-Boc-4-aminomethylpiperidine (compound R1, 6.4 μL, 30.4 μmol), and DMT-MM (9.0 mg, 30.4 μmol) were dissolved in DMF (1.5 mL), and stirred at room temperature. N,N-diisopropylethylamine (5.3 μL) was added, and stirred for another two hours. The solvent was distilled off under reduced pressure. The residue obtained was purified by HPLC (A/B=90/10 to 10/90, 40 min). The compound obtained was dissolved in trifluoroacetic acid (5 mL), and stirred at room temperature until the reaction was completed. The solution was distilled off under reduced pressure. The residue obtained was purified by HPLC (A/B=90/10 to 10/90, 40 min), and compound R2 (5.1 mg, 69%) was obtained as a bluish-violet solid.

HRMSI-ESI (m/z): '[M]$^+$ calcd for C$_{29}$H$_{35}$N$_4$OSi: 483.25746; found: 483.25686 (0.6 mDa, 1.2 ppm).

[Synthesis of Compound 32]

Compound R2 (2.3 mg, 4.8 μmol), compound H2 (2.2 mg, 4.8 μmol), and DMT-MM (10 mg) were dissolved in DMF (3 mL), and stirred at room temperature. N,N-diisopropylethylamine (1.8 μL, 9.6 μmol) was added, and stirred overnight at room temperature. The solvent was distilled off under reduced pressure. The residue obtained was separated and purified by HPLC (A/B=90/10 to 10/90, 40 min), and the target compound 32 (4.9 mg, quant.) was obtained as a bluish-violet solid.

HRMS-ESI (m/z): [M]$^+$ calcd for C$_{54}$H$_{49}$N$_4$O$_9$Si: 925.32633; found: 925.32417 (2.2 mDa, 2.3 ppm).

[Synthesis of compounds 33 and 34]

Compounds 33 and 34, which are fluorescent probes of the present invention, were synthesized according to scheme 22 below.

Scheme 22
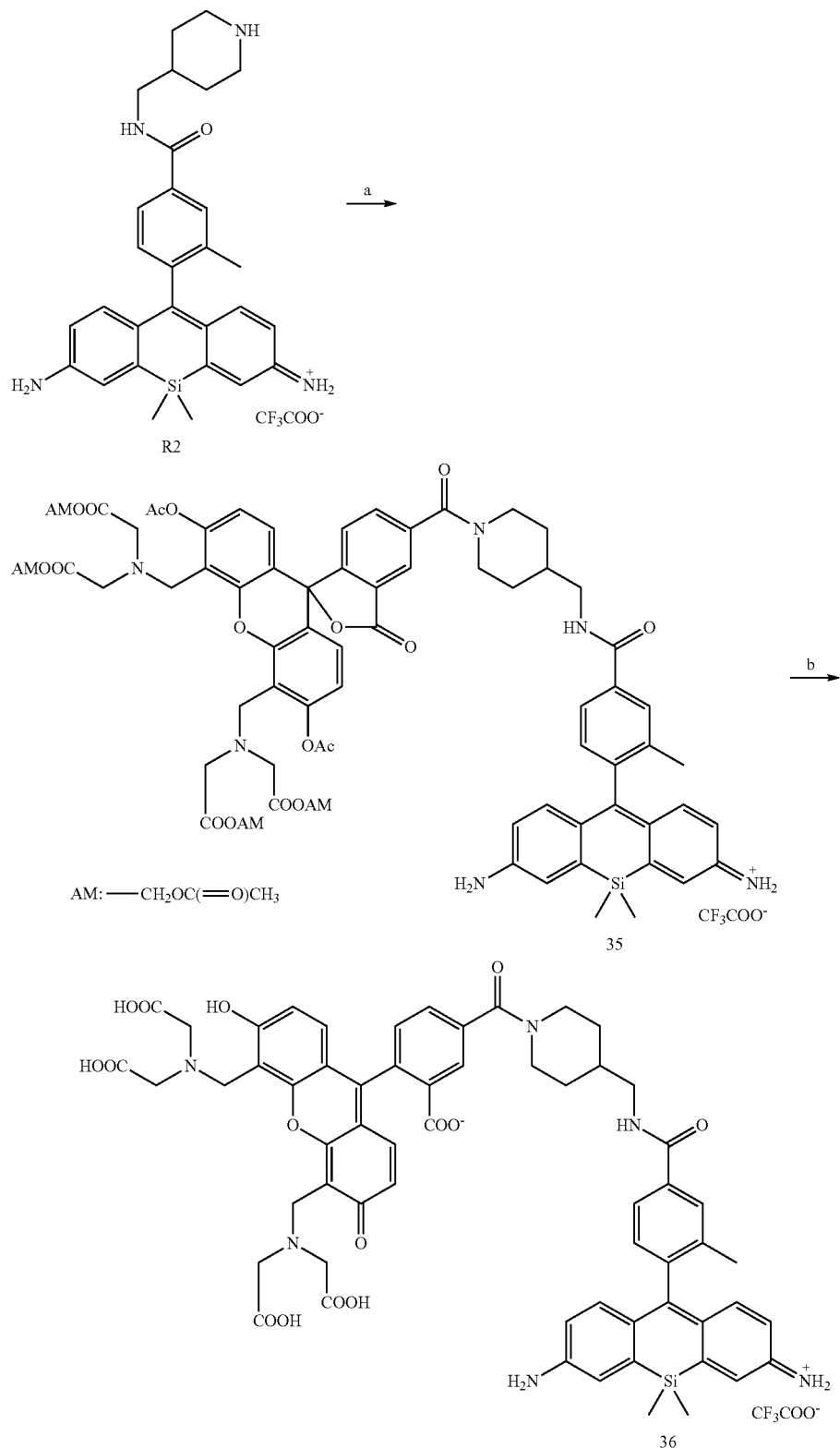
a) compound Q2, DMT—MM, DIEA, DMF, rt.;
b) 1N KOHaq., MeOH, rt.

[Synthesis of Compound 33]

Compound R2 (2.8 mg, 5.9 μmol), compound Q2 (6.1 mg, 5.9 μmol), and DMT-MM (10 mg) were dissolved in DMF (3 mL), and stirred at room temperature. N,N-diisopropylethylamine (2.0 μL, 11.8 μmol) was added, and stirred overnight at room temperature. The solvent was distilled off under reduced pressure. The residue obtained was separated and purified by HPLC (A/B=90/10 to 10/90, 40 min), and the target compound 33 (5.1 mg, 57%) was obtained as a bluish-violet solid.

HRMS-ESI (m/z): [M]$^+$ calcd for $C_{76}H_{79}N_6O_{25}Si$: 1503.4858 found: 1503.4872 (−1.3 mDa, −0.9 ppm).

[Synthesis of Compound 34]

Compound 33 was dissolved in methanol (5 mL) and water (3 mL). 1N potassium hydroxide aqueous solution was added, and stirred at room temperature. The solvent was distilled off under reduced pressure. Separation and purification were performed by HPLC (A/B=90/10 to 10/90, 40 min), and the target compound 34 was obtained as a bluish-violet solid.

Example 2

Fluorescence Assay for Glutathione

Glutathione was reacted with the fluorescent probe 2Me SiR600 (compound 1) synthesized in Example 1, and fluorescence assay was conducted. A Shimadzu UV-2450 (Shimadzu Corporation) and a Hitachi F-7000 (Hitachi, Ltd.) were used in ultraviolet-visible spectroscopy and fluorescence spectroscopy. A fluorescent probe was diluted to a final concentration of 1 μM in 0.2 M sodium phosphate buffer (pH 7.4), containing 0.1-1% DMSO. The absorption spectrum and fluorescence spectrum were measured when various concentration of glutathione was added in the range of 1 μM-100 mM. The excitation wavelength was 590 nm. The results obtained are shown in FIGS. 1 and 2.

Figure 2:
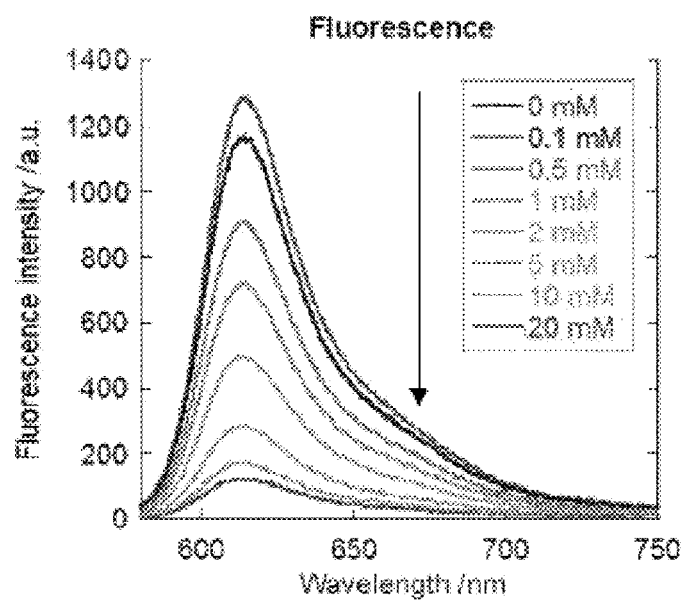
FIG. 2 is a graph showing the changes in the fluorescence spectrum of compound 1 "2Me SiR600," which is a fluorescent probe of the present invention, associated with glutathione addition.

As shown in FIGS. 1 and 2, significant decreases in absorption and fluorescence intensity were found due to glutathione addition. By plotting values at absorption peak wavelength (593 nm) and fluorescence peak wavelength (614 nm) against glutathione concentration, the dissociation constant Kd (mM) was calculated, which were 1.0 mM and 1.1 mM, respectively.

Table 1 shows the results obtained by conducting the same assay under the same conditions using compound 2 "Ph SiR650," compound 3 "2OMe SiR650," compound 4 "2OH SiR650," compound 5 "2CN SiR650," compound 6 "2OMe OxaSiR diMe," and compound 7 "2OH OxaSiR diMe," which are other probes (Kd is the result of calculation based on changes in the fluorescence spectrum).

TABLE 1

Compound 1

2Me SiR600

| | |
|---|---|
| Absorption peak (nm) | 593 |
| Fluorescence peak (nm) | 613 |
| Quantum yield | 0.38 |
| Kd (mM) | 1.1 |

Compound 2

Ph SiR650

| | |
|---|---|
| Absorption peak (nm) | 645 |
| Fluorescence peak (nm) | 668 |
| Quantum yield | 0.14 |
| Kd (mM) | 0.9 |

Compound 3

2OMe SiR650

| | |
|---|---|
| Absorption peak (nm) | 649 |
| Fluorescence peak (nm) | 672 |
| Quantum yield | 0.37 |
| Kd (mM) | 41 |

Compound 4

2OH SiR650

| | |
|---|---|
| Absorption peak (nm) | 648 |
| Fluorescence peak (nm) | 672 |
| Quantum yield | 0.31 |
| Kd (mM) | 43 |

TABLE 1-continued

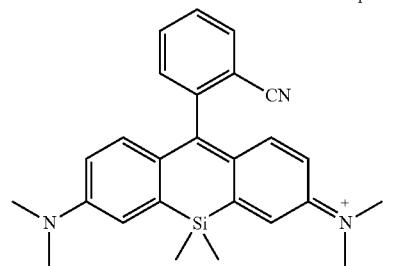

Compound 5

2CN SiR650

| | |
|---|---|
| Absorption peak (nm) | 658 |
| Fluorescence peak (nm) | 683 |
| Quantum yield | 0.25 |
| Kd (mM) | 1.2 |

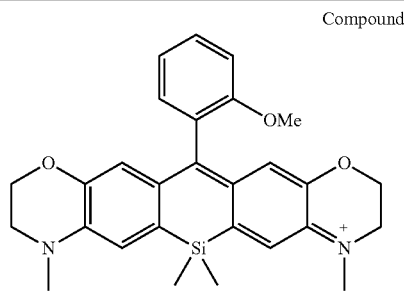

Compound 6

2OMe OxaSiR diMe

| | |
|---|---|
| Absorption peak (nm) | 699 |
| Fluorescence peak (nm) | 740 |
| Quantum yield | 0.08 |
| Kd (mM) | 0.7 |

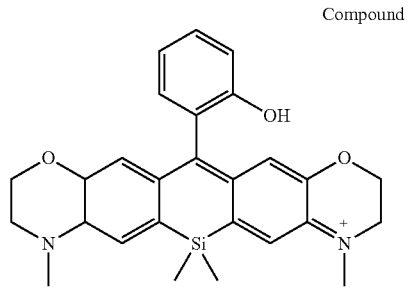

Compound 7

2OH OxaSiR diMe

| | |
|---|---|
| Absorption peak (nm) | 699 |
| Fluorescence peak (nm) | 739 |
| Quantum yield | 0.07 |
| Kd (mM) | 0.9 |

Based on the results in Table 1, the dissociation constant Kd for glutathione was demonstrated to be dependent on the structure of the fluorescent probe. A probe having Kd of about 100 μM-10 mM, which is in the range of intracellular concentration of glutathione, is especially suitable. The fluorescence peak wavelength can be adjusted in the 613-739 nm range, and all quantum yields were also demonstrated to be high. In other words, these fluorescent probes were demonstrated to be useful in the detection of glutathione within cells. Further, the absorption spectra of compound 1 (2-Me SiR600) overlapped well with the fluorescence spectra of existing dyes (fluorescein, rhodamine, and the like), suggesting that it is also suitable for application to a ratiometric fluorescent probe using FRET.

Similarly, compounds 11-27 synthesized in Example 1 were assayed under the same conditions. The results are shown in Table 2. Based on the results in Table 2, these fluorescent probes were also demonstrated to be useful in the detection of glutathione within cells.

TABLE 2

| Compound | Absorption peak [nm] | Fluorescence peak [nm] | Fluorescence quantum yield | $K_d$ [mM] |
|---|---|---|---|---|
| 11 | 592 | 614 | 0.44 | 2.3 |
| 12 | 592 | 614 | 0.46 | 2.3 |
| 13 | 604 | 627 | 0.31 | 8 |
| 14 | 607 | 630 | 0.28 | 2.0 |
| 15 | 607 | 630 | 0.21 | 2.5 |
| 16 | 620 | 643 | 0.34 | 16 |
| 17 | 620 | 643 | 0.22 | 21 |
| 18 | 655 | 677 | 0.19 | 1.3 |
| 19 | 652 | 675 | 0.30 | 23 |
| 20 | 653 | 676 | 0.31 | 12 |
| 21 | 650 | 673 | 0.20 | 0.6 |
| 22 | 650 | 673 | 0.16 | 0.5 |
| 23 | 655 | 676 | 0.30 | 27 |
| 24 | 652 | 674 | 0.15 | 0.4 |
| 25 | 651 | 675 | 0.07 | 0.4 |
| 26 | 620 | 643 | 0.14 | 15 |
| 27 | 695 | 738 | 0.06 | 2.1 |

Example 3

Evaluation of Reversibility of Fluorescence Response

The reversibility of the reaction of the fluorescent probe and glutathione was evaluated by observing the change in absorption when glutathione was added, followed by addition of a thiol scavenger. Measurement was conducted using fluorescent probes of compound 1 "2Me SiR600" and compound 2 "Ph SiR650." The results are shown in FIG. 3.

Figure 3:
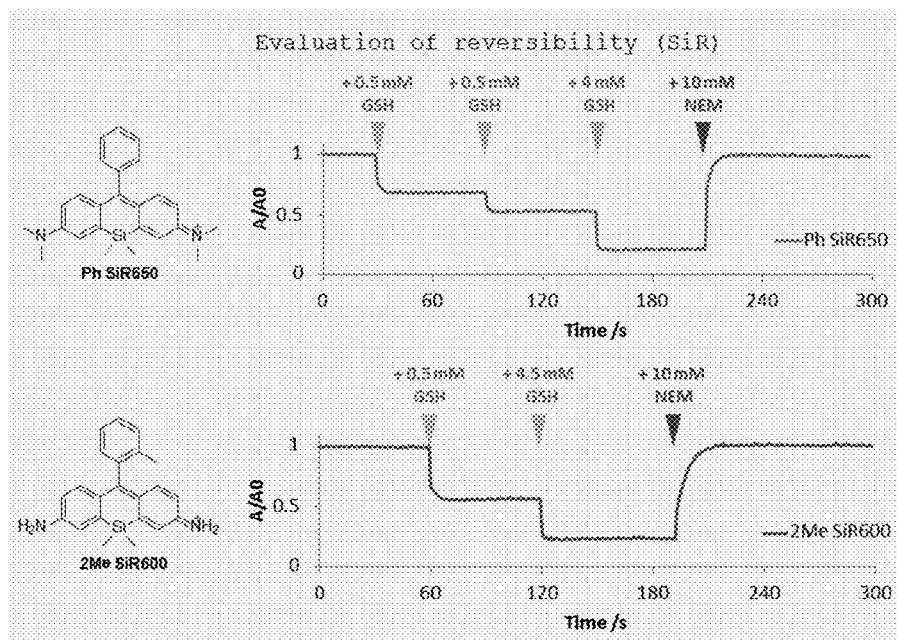
FIG. 3 is a graph showing the time dependence of changes in the absorption spectrum intensity when glutathione was added to fluorescent probe compound 1 and compound 2 of the present invention, and N-ethylmaleimide (NEM) was then added.

Based on the results in FIG. 3, these fluorescent probes were demonstrated to respond rapidly to glutathione (time until reaching equilibrium: 10 seconds or less) and to produce changes in absorption spectrum intensity depending on the glutathione level. The reversibility of the response to glutathione was confirmed by the fact that the absorbance returned to the same value without addition of glutathione when the thiol scavenger N-ethylmaleimide (NEM) was added.

Example 4

Cell Imaging by Compound 1 (2Me SiR600)

Figure 4:
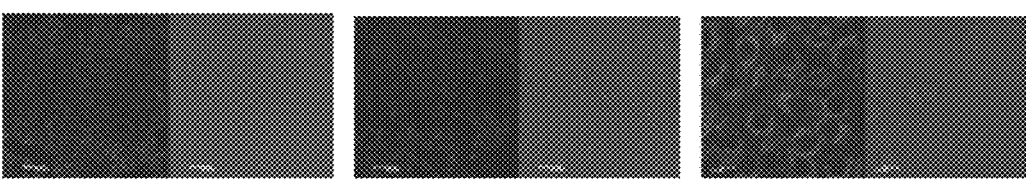
FIG. 4 is an image showing the results of fluorescence imaging in cancer cells cultured using compound 1 "2ME SiR600," which is a fluorescent probe of the present invention.
Figure 4:
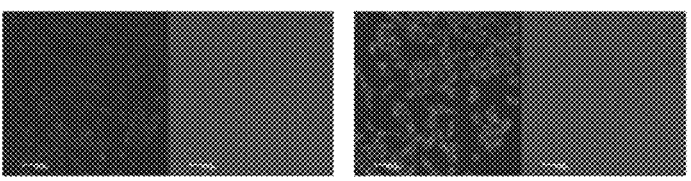

Next, cell imaging in cultured cancer cells was conducted using compound 1 (2Me SiR600) as a fluorescent probe. Measurement was conducted using a confocal microscope. The images obtained are shown in FIG. 4. Fluorescent images were observed soon after administration of the fluorescent probe, and were expected to reflect changes in the intracellular glutathione concentration since an increase in fluorescence intensity was found under conditions of glutathione depletion due to N-ethylmaleimide (NEM) addition.

Example 5

Assay by Fluorescent Probe Using FRET

Figure 5:
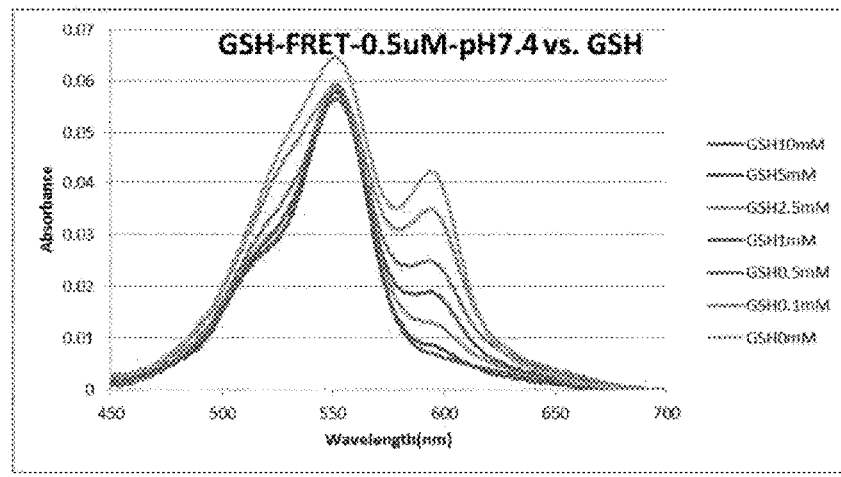
FIG. 5 is a graph showing the changes in the absorption spectrum of compound 8 "2Me SiR600-TMR," which is a fluorescent probe of the present invention, associated with glutathione addition.
Figure 6:
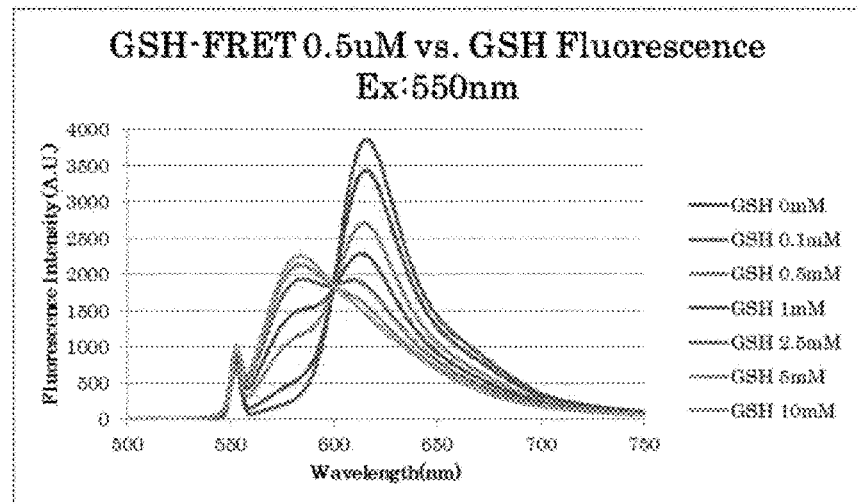
FIG. 6 is a graph showing the changes in the fluorescence spectrum of compound 8 "2Me SiR600-TMR," which is a fluorescent probe of the present invention, associated with glutathione addition.
Figure 7:
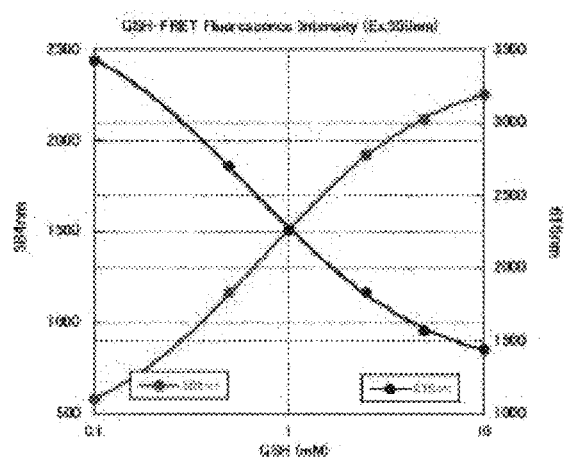
FIG. 7 is a graph plotting the changes in the intensity of the acceptor peak wavelength (615 nm) and donor peak wavelength (584 nm) in the fluorescence spectrum of FIG. 6.

The changes in the absorption and fluorescence spectra associated with glutathione addition were measured in the same way as in Example 2 using the compound 8 (2Me SiR600-TMR) synthesized in Example 1, which is a probe having a donor fluorophore in the molecule. The fluorescent probe was diluted to a final concentration of 0.5 µM in 0.2 M sodium phosphate buffer (pH 7.4), containing 0.1% DMSO. The added glutathione concentration was varied in the 1 µm-10 mM range. The excitation wavelength was 550 nm. The results obtained are shown in FIGS. 5 and 6, respectively. FIG. 7 shows a plot of the changes in the intensity of the acceptor peak wavelength (615 nm) and donor peak wavelength (584 nm) in the fluorescence spectrum of FIG. 6.

As demonstrated in FIGS. 6 and 7, an increase in the fluorescence intensity of the 584 nm peak was obtained together with a decrease in the fluorescence intensity of the 615 nm peak in association with glutathione addition. This result shows that this fluorescent probe (compound 8) achieved the detection of physiological concentrations of glutathione by the ratiometric detection (dual-emission ratio) due to a FRET mechanism rather than the single-emission detection as in Example 2.

Example 6

Cell Imaging by Compound 8 (2Me SiR600-TMR)

Figure 8:
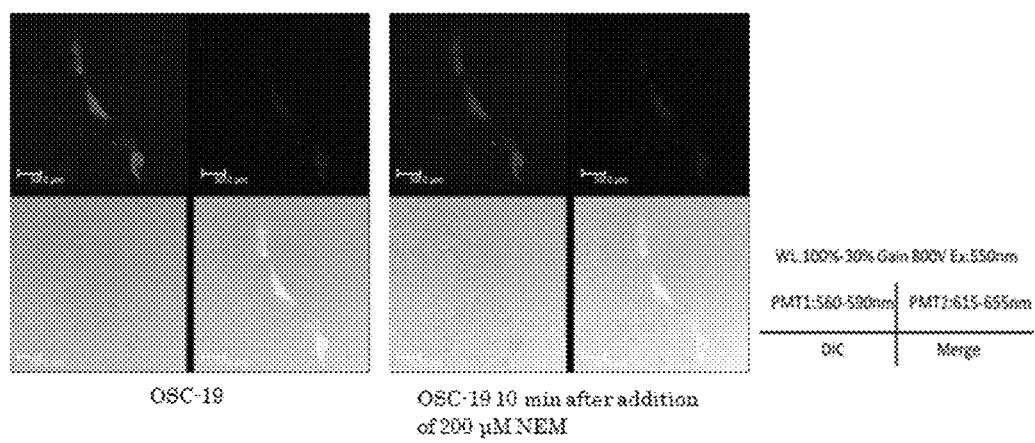
FIG. 8 is an image showing the results of fluorescence imaging in cancer cells cultured using compound 8 "2ME SiR600-TMR," which is a fluorescent probe of the present invention.

Fluorescence imaging in cultured cancer cells was conducted in the same way as in Example 4 using compound 8 (2Me SiR600-TMR) as the fluorescent probe (FIG. 8). The change in fluorescence intensity ratio observed due to NEM addition suggested that this fluorescent probe reacts with intracellular glutathione within the cells.

Figure 9:
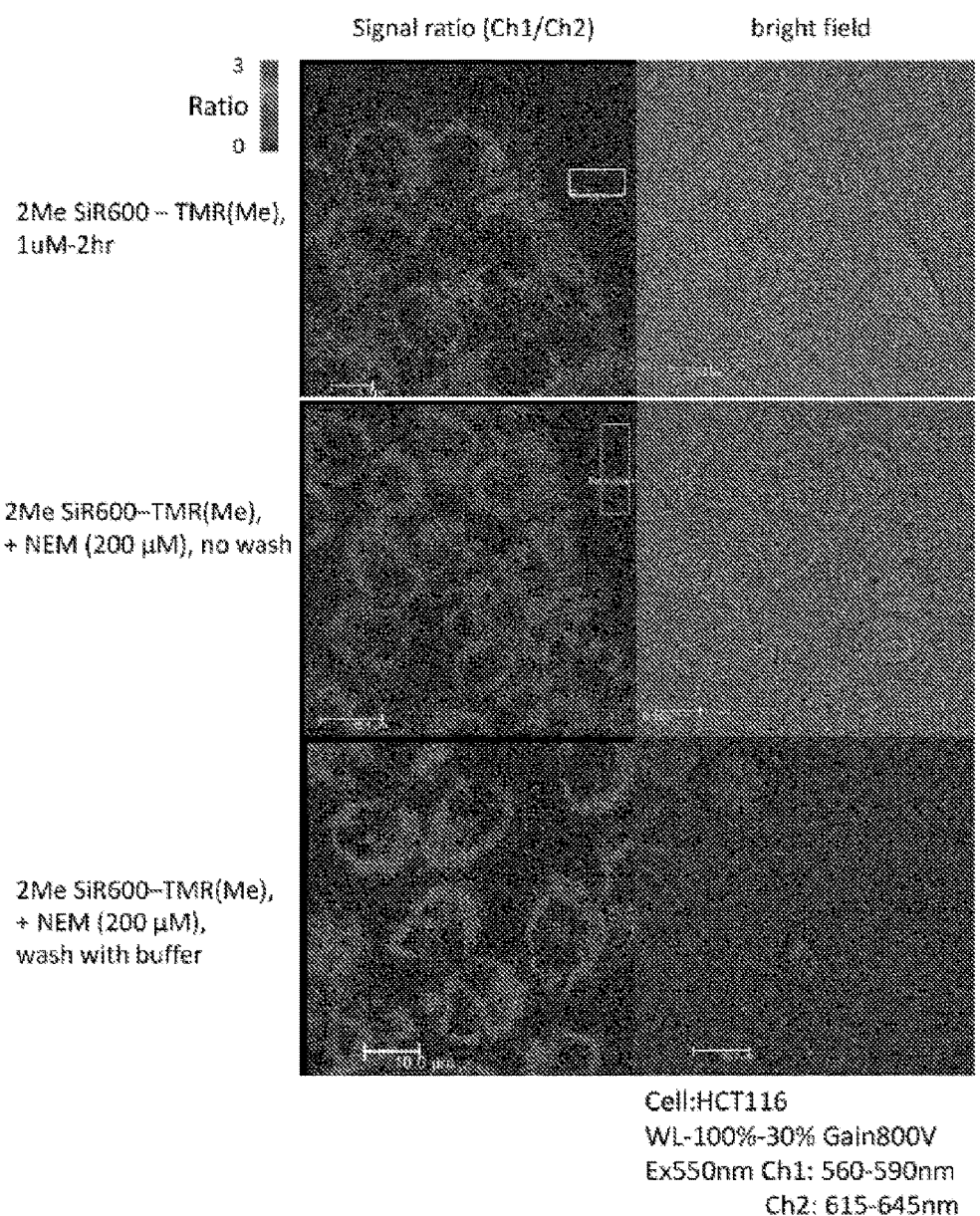
FIG. 9 is an image showing the results of fluorescence imaging in cancer cells cultured using compound 9 "2Me SiR600-TMR(Me)," which is a fluorescent probe of the present invention.

Similarly, a change in fluorescence intensity ratio due to NEM addition was also observed as a result (FIG. 9) of cell imaging using the compound 9 "2Me SiR600-TMR(Me)" synthesized in Example 1.

The invention claimed is:

1. A fluorescent probe for detecting a compound containing an —SH group, wherein the fluorescent probe comprises a compound represented by formula (I) or a salt thereof:

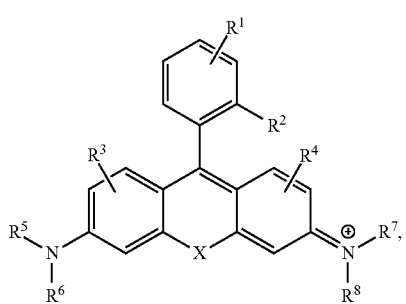

(I)

in which

X represents $Si(R^a)(R^b)$, $Ge(R^a)(R^b)$, $Sn(R^a)(R^b)$, or $C(R^a)(R^b)$, wherein $R^a$ and $R^b$ each independently represents a hydrogen atom;

$R^1$ represents a hydrogen atom, or 1-4 identical or different substituents independently selected from the group consisting of a cyano group, an alkyl group, a carboxyl group, an ester group, an alkoxy group, an amide group, and an azide group, each of which may be optionally substituted;

$R^2$ represents a hydrogen atom, a halogen atom, a hydroxyl group, a cyano group, or an alkyl group, an alkynyl group, an alkoxy group, an aryl, or a heteroaryl, each of which may be optionally substituted;

$R^3$ and $R^4$ each independently represents a hydrogen atom or 1-3 identical or different substituents independently selected from the group consisting of a hydroxyl group, a halogen atom, an alkyl group, a sulfo group, a carboxyl group, an ester group, an amide group, and an azide group, each of which may be optionally substituted;

$R^5$, $R^6$, $R^7$ and $R^8$ each independently represents a hydrogen atom or an alkyl group, wherein, $R^5$ or $R^6$, respectively together with $R^3$, may form a ring structure including the nitrogen atoms bonded thereto, or $R^7$ or $R^8$, respectively together with $R^4$, may form a ring structure including the nitrogen atoms bonded thereto.

2. The fluorescent probe according to claim 1, wherein the compound containing an —SH group is a compound having a cysteine residue.

3. The fluorescent probe according to claim 1, wherein the compound containing an —SH group is glutathione.

4. The fluorescent probe according to claim 1, wherein X is $Si(R^a)(R^b)$.

5. The fluorescent probe according to claim 1, wherein $R^2$ is a hydrogen atom, a hydroxyl group, a cyano group, a $C_1$-$C_4$ alkyl group, a $C_1$-$C_4$ alkoxy group, or a phenyl group, each of which may be optionally substituted;

$R^5$, $R^6$, $R^7$, and $R^8$ is each independently a hydrogen atom or a methyl group.

6. The fluorescent probe according to claim 1, wherein $R^1$ has a fluorophore that serves as a fluorescence resonance energy transfer (FRET) donor.

7. The fluorescent probe according to claim 1, wherein $R^5$, $R^6$, $R^7$, and $R^8$ have a fluorophore that serves as a fluorescence resonance energy transfer (FRET) donor.

8. The fluorescent probe according to claim 6, wherein the fluorophore is a compound having a xanthene skeleton.

9. A method for detecting a compound containing an —SH group comprising a step of contacting the fluorescent probe according to claim 1 with a compound containing an —SH group.

10. The method according to claim 9, wherein the presence of a compound containing an —SH group is detected by observing the fluorescence response or change in absorbance due to a reaction between the compound containing an —SH group and the fluorescent probe.

11. The method according to claim 10, wherein the fluorescence response is a change in fluorescence due to fluorescence resonance energy transfer (FRET).

12. The method according to claim 10, wherein the fluorescence response is visualized using fluorescence imaging means.

13. The method according to claim 9, wherein the compound containing an —SH group is a compound having a cysteine residue.

14. The method according to claim 9, wherein the compound containing an —SH group is glutathione.

15. A kit for detecting a compound containing an —SH group including the fluorescent probe according to claim 1.

16. The kit according to claim 15, wherein the compound containing an —SH group is a compound having a cysteine residue.

17. The kit according to claim 15, wherein the compound containing an —SH group is glutathione.

* * * * *